US011624056B2

(12) United States Patent
Ju et al.

(10) Patent No.: US 11,624,056 B2
(45) Date of Patent: Apr. 11, 2023

(54) METHOD FOR PRODUCING CARTILAGE CELLS INDUCED TO BE DIFFERENTIATED FROM STEM CELLS

(71) Applicant: YiPCELL Inc., Seoul (KR)

(72) Inventors: Ji Hyeon Ju, Seoul (KR); Yoo Jun Nam, Bucheon-si (KR); Yeri Rim, Seoul (KR)

(73) Assignee: YiPCELL Inc., Seoul (KR)

( * ) Notice: Subject to any disclaimer, the term of this patent is extended or adjusted under 35 U.S.C. 154(b) by 697 days.

(21) Appl. No.: 16/479,079

(22) PCT Filed: Jan. 19, 2018

(86) PCT No.: PCT/KR2018/000903
§ 371 (c)(1),
(2) Date: Jul. 18, 2019

(87) PCT Pub. No.: WO2018/135902
PCT Pub. Date: Jul. 26, 2018

(65) Prior Publication Data
US 2019/0390167 A1 Dec. 26, 2019

(30) Foreign Application Priority Data
Jan. 19, 2017 (KR) .................. 10-2017-0009015
Jan. 19, 2017 (KR) .................. 10-2017-0009019

(51) Int. Cl.
*C12N 5/077* (2010.01)
*A61K 35/32* (2015.01)
*C12N 15/85* (2006.01)

(52) U.S. Cl.
CPC ............ *C12N 5/0655* (2013.01); *A61K 35/32* (2013.01); *C12N 15/85* (2013.01); *C12N 2500/50* (2013.01); *C12N 2501/15* (2013.01); *C12N 2501/155* (2013.01); *C12N 2501/998* (2013.01); *C12N 2506/45* (2013.01); *C12N 2533/54* (2013.01)

(58) Field of Classification Search
CPC ............ C12N 5/0655; C12N 15/85; C12N 2500/50; C12N 2501/15; C12N 2501/155; C12N 2501/998; C12N 2506/45; C12N 2533/54; A61K 35/32
See application file for complete search history.

(56) References Cited

U.S. PATENT DOCUMENTS

2011/0229440 A1 9/2011 Dealy et al.
2012/0058562 A1 3/2012 Thomson et al.

OTHER PUBLICATIONS

Li et al ("Reprogramming of blood cells into induced pluripotent stem cells as a new cell source for cartilage repair," Stem Cell Research & Therapy (2016) 7:31).*
Min et al ("Characterization of subpopulated articular chondrocytes separated by percoll density gradient," In Vitro Cell. Dev. Biol.—Animal 38:35M.0, Jan. 2002) (Year: 2002).*
Shen et al ("BMP-2 Enhances TGF-b3-Mediated Chondrogenic Differentiation of Human Bone Marrow Multipotent Mesenchymal Stromal Cells in Alginate Bead Culture,"Tissue Engineering: Part A vol. 15, No. 6, 2009) (Year: 2009).*
Fanganiello et al ("Increased In Vitro Osteopotential in SHED Associated with Higher IGF2 Expression When Compared with hASCs," Stem Cell Rev and Rep (2015) 11:635-644) (Year: 2015).*
Guzzo et al ("Efficient Differentiation of Human iPSC-DerivedMesenchymal Stem Cells to Chondroprogenitor Cells," Journal of Cellular Biochemistry 114:480-490 (2013) (Year: 2013).*
Hu et al ("Efficient generation of transgene-free induced pluripotent stem cells from normal and neoplastic bone marrow and cord blood mononuclear cells," Blood, Apr. 7, 2011 vol. 117, No. 14) (Year: 2011).*
Jang et al ("Centrifugal gravity-induced BMP4 induces chondrogenic differentiation of adipose derived stem cells via SOX9 upregulation," Stem Cell Research & Therapy (2016) 7:184) (Year: 2016).*
Li Yueying et al., "Reprogramming of Blood Cells into Induced Pluripotent Stem Cells as a New Cell Source for Cartilage Repair", Stem Cell Research & Therapy, 2016, vol. 7, Article No. 3, pp. 1-11.
Revazova, E.S. et al., "HLA Homozygous Stem Cell Lines Derived from Human Parthenogenetic Blastocysts", Cloning and Stem Cells, 2008, vol. 10, No. 1, pp. 1-14.
Wei, Yiyong et al., "Chondrogenic: Differentiation of Induced Pluripotent Stem Cells from Osteoarthritic Chondrocytes in Alginate Matrix", European Cells and Materials, 2012. vol. 23, pp. 1-12.
Koyama, Noriaki et al., "Human Induced Pluripotent Stem Cells Differentiated into Chonclrogenic Lineage via Generation of Mesenchymal Progenitor Cells", Stem Cells and Development, 2012. vol. 2. No. 1, pp. 1-12.
Nam, Yoojun et al., "Cord Blood Cell-derived iPSCs as a New Candidate for Chondrogenic Differentiation and Cartilage Regeneration". Stem Cell Research & Therapy, 2017. vol. 8. Article No. 16, inner pp. 1-13.

(Continued)

*Primary Examiner* — Titilayo Moloye
*Assistant Examiner* — Suzanne E Ziska
(74) *Attorney, Agent, or Firm* — Rothwell, Figg, Ernst & Manbeck, P.C.

(57) ABSTRACT

The present invention relates to a method for inducing differentiation, into chondrocytes, of cord blood mononuclear cell-derived induced pluripotent stem cells. In a case where a chondrogenic pellet produced by the method of the present invention is transplanted into a cartilage damage area in vivo, regeneration of cartilage can be effectively exhibited by differentiated chondrocytes. In such a case, an effective cartilage regeneration capacity can be exhibited as compared with a case where chondrocytes produced by differentiation induction with the addition of a recombinant growth factor are transplanted. Thus, the present invention can be usefully used for tissue engineering therapies.

4 Claims, 24 Drawing Sheets

Specification includes a Sequence Listing.

(56) References Cited

OTHER PUBLICATIONS

Bandara et al., "Minicircle DNA-mediatd endothelial nitric oxide synthase gene transfer enhances angiogenic responses of bone marow-deived mesenchymal stem cells", Stem Cell Research & Therapy, (2016), 7:48, 15 pgs.

Barry et al., "Chondrogenic Differentiation of Mesenchymal Stem Cells from Bone Marrow: Differentiation-Dependent Gene Expression of Matrix Components", Experimental Cell Research, 268, (2001), pp. 189-200.

Gill et al., "Progress and Prospects: The design and production of plasmid vectors", Gene Therapy (2009), 16, pp. 165-171.

Mueller et al., "Functional Characterization of Hypertrophy in Chondrogenesis of Human Mesenchymal Stem Cells", Arthritis & Rheumatism, vol. 58, No. 5, May 2008, pp. 1377-1388.

Tsuchiya et al., "Chondrogenesis enhanced by overexpression of sox9 gene in mouse bone marrow-derived mesenchymal stem cells", Biochemcial and Biophysical Research Communications 301 (2003), pp. 338-343.

Tuli et al., "Transforming Growth Factor-B-mediated Chondrogenesis of Human Mesenchymal Progenitor Cells Involves N-cadherin and Mitogen-activated Protein Kinase and Wnt Signaling Cross-Talk", The Journal of Biological Chemistry, vol. 278, No. 42, 2003, pp. 41227-41236.

Shu et al., "BMP2, but not BMP4, is crucial for chondrocyte prolifereation and maturation during endochondral bone development", Journal of Cell Science, 124, (2011) pp. 3428-3440.

Wang et al., "Delivery of the Sox9 gene promotes chrondrogenic differentiation of human umbilical cord blood-derived mesenchymal stem cells in an in vitro model", Brazilian Journal of Medical and Biological Research, (2014) 47(4), pp. 279-286.

Kim et al., "Overexpression of SOX9 in mouse embryoic stem cells directs the immediate chondrogenic commitment", Experimental and Molecular Medicine, vol. 37, No. 4, 2005, pp. 261-268.

Kim et al., "The Generation of Human Induced Pluripotent Stem Cells from Blood Cells: An Efficient Protocol Using Serial Plating of Reprogrammed Cells by Centrifugation", Stem Cells International, vol. 2016, pp. 1-9.

Kim et al., "Overexpression of TGF-B1 enhances chrondrogenic differentiation and proliferation of human synovium-derived stem cells", Biochem Biophys Res Commun, 2014, 450(4), pp. 1593-1599.

Chinese First Office Action issued in 201880007802.1 dated Oct. 31, 2022, 13 pages.

* cited by examiner

METHOD FOR PRODUCING CARTILAGE CELLS INDUCED TO BE DIFFERENTIATED FROM STEM CELLS

CROSS REFERENCE TO RELATED APPLICATIONS

The present application is a 35 U.S.C. 371 National Phase Entry from PCT/KR2018/000903, filed Jan. 19, 2018, which claims priority to Korean Patent Application No. 10-2017-0009015 filed on Jan. 19, 2017, and Korean Patent Application No. 10-2017-0009019 filed on Jan. 19, 2017, the entireties of which are incorporated herein by reference.

This research was supported by a grant of the Korea Health Technology R&D Project through the Korea Health Industry Development Institute (KHIDI), funded by the Ministry of Health & Welfare, Republic of Korea (HI16C2177, HI18C1178, HO16C0001).

SEQUENCE LISTING STATEMENT

The instant application contains a Sequence Listing in electronic format which has been submitted via EFS-Web. Said Sequence Listing, created on Jul. 18, 2019, is named "4669-125_ST25.Txt" and is 4 kilobytes in size. The information in the electronic format of the Sequence Listing is part of the present application and is incorporated herein by reference in its entirety.

TECHNICAL FIELD

The present invention relates to a method for producing a composition for differentiation into chondrocytes, a chondrocyte produced by differentiation therefrom, and a pharmaceutical composition for preventing or treating a cartilage-related disease, comprising the composition for differentiation into chondrocytes or the chondrocyte produced by differentiation, which are capable of providing new strategies for personalized regenerative medicine.

BACKGROUND

Cartilage is a bone tissue composed of chondrocytes and cartilage matrix, and usually refers to a tissue that forms part of a joint. Cartilage consists mostly of chondrocytes and a large amount of extracellular matrix (ECM) in which various types of collagen, proteoglycans, and flexible fibers are enriched. As a result, cartilage has high elasticity and a very low coefficient of friction, and serves as a buffer to prevent friction between the ends of bone, thereby helping joints to move with little friction. In addition, cartilage serves to construct a framework for a portion that requires elasticity, such as an organ of the respiratory tract or auricle, or a portion that requires resistance to pressure, such as costal cartilage or symphyseal cartilage.

In particular, articular cartilage is composed of chondrocytes that are cells specially differentiated so as to be distributed between cartilage matrices. Chondrocytes serve to create and maintain articular cartilage. Cell division occurs in chondroblasts. However, once growth stops, chondrocytes are trapped in a small space called lacuna and no longer divide in a normal environment.

Therefore, once cartilage is damaged, regeneration thereof is difficult to occur. In addition, since cartilage is an avascular tissue, there is no blood vessel for nutritional supply, so that there is a limitation for migration of stem cells and regeneration capacity of tissue is decreased. Therefore, various regenerative medicine researches have been conducted for the purpose of increasing regeneration capacity of cartilage, such as inducing differentiation into chondrocytes for regeneration of cartilage. The most commonly used technique for this is a cell therapy technique using cells. However, such a technique has a disadvantage in that proliferation efficiency differs depending on types of cell lines so that there may be limitations. Accordingly, it has recently been known that adult stem cells such as adipocyte-derived stem cells or mesenchymal stem cells (MSCs), which are isolated autologously from patients, are induced to differentiate into chondrocytes in vitro and used for cell therapies.

However, even in such cell therapies, early chondrocytes and adult stem cells rapidly lose characteristics of chondrocytes when they are cultured in vitro. Thus, there are restrictions that their continued use is limited after being transplanted into the body. In addition, for differentiation capacity of adult stem cells to differentiate into chondrocytes, characteristics thereof may vary depending on pathological characteristics of sources from which the adult stem cells are isolated. Thus, there are concerns about side effects in that many variables may be present in applying such cell therapies to actual regenerative medicine.

Accordingly, studies have been attempted to use human induced pluripotent stem cells (hiPSCs) as cell therapeutic agents for tissue regeneration medicine. The hiPSCs are characterized in that they have differentiation capacity to differentiate into various lineages and thus can be used regardless of types of tissues in tissue regeneration medicine [NPL 1]. Therefore, even for a tissue in which low differentiation capacity is exhibited in a case of being induced to differentiate from stem cells, a relatively high regeneration effect can be expected in a case of using hiPSCs.

Among growth factors used for inducing hiPSCs to differentiate into chondrocytes, bone morphogenetic protein (BMP), transforming growth factor (TGF), or the like has recently been used [NPL 2]. BMP alone is known to play a major role in development of bone and cartilage, and is also known to affect the survival and proliferation of chondrocytes. Among these, it has been reported that due to deficiency of BMP2, development of endochondral bone may be inhibited [NPL 3].

TGFβ proteins are known as factors that regulate structural frameworks in various tissues through their involvement in processes such as proliferation, differentiation, and death of cells. The TGFβ proteins are divided into three protein isoforms such as TGFβ1, TGFβ2, and TGFβ3, and it has been reported that cartilage formation may be induced through action among these isoforms [NPLS 4 and 5]. Among these, cartilage formation may be induced, in particular, using TGFβ1 or TGFβ3, in which TGFβ3 has been reported to have higher differentiation capacity [NPL 6]. In the process of inducing stem cells to differentiate into cells of a target tissue, use of recombinant human growth factors may function as an important element. However, this requires frequent addition of growth factor molecules during differentiation, which involves a disadvantage that an expensive cost is incurred.

In order to overcome such a disadvantage, attempts have been made, in the process of differentiating stem cells, to induce differentiation thereof into cells of a target tissue by inducing overexpression of growth factors through gene transfer in a state where growth factors are not added to a medium. With regard to differentiation into chondrocytes, it has been reported that in a case where gene delivery of TGFβ1 is made with a viral vector in synovial-derived MSCs, cell proliferation may be increased and a rate of chondrogenic differentiation may be accelerated [NPL 7]. In addition, in a case where SOX9 is overexpressed in mouse mesenchymal stem cells (MSCs) and cord blood-derived MSCs, differentiation into chondrocytes may be promoted [NPLS 8 and 9], and expression of type 2 collagen may be also increased [NPL 10].

With regard to gene delivery techniques for such cell therapies, a non-viral gene delivery technique has attracted attention as a safe method. This is because commercial DNA vector plasmids contain sequences of bacterial origin, which may induce an immune response to bacterial proteins. For this purpose, a minicircle vector can be used, and the minicircle vector refers to a vector having a relatively small size, obtained by removing an antibiotic resistance gene, a gene encoding a bacterial structural protein, and a transcription unit gene. The minicircle vector has a feature capable of expressing an exogenous gene at a high level in vitro and in vivo, along with advantages of being small in size and capable of avoiding an immune response. Thus, the minicircle vector attracts attention for its potential of being beneficially used in preclinical gene therapy studies [NPL 11]. Through this, safe and efficient gene delivery becomes possible, and thus a therapeutic effect can be enhanced in a case where genetically modified stem cells are applied to therapies [NPL 12].

In addition, in conventional methods for inducing differentiation of stem cells into chondrocytes, differentiation into chondrocytes is induced in a process in which induced pluripotent stem cell-derived embryoid bodies are generated and differentiation into chondrocytes is continuously induced therefrom. In this process, in order to increase differentiation efficiency, a method has been studied in which embryoid bodies are cultured in a gelatin medium to obtain outgrowth cells (OG cells), and the resulting cells are caused to differentiate into single cells so that differentiated chondrocytes are obtained. However, since it is required to further increase differentiation efficiency so as to use chondrocytes, which are produced by differentiation induction from stem cells, as a cell therapeutic agent in regenerative medicine, studies on development of a method for more effectively producing chondrocytes have been continuously conducted.

Accordingly, the present inventors have studied to develop a method in which stem cells are induced to differentiate into a chondrogenic pellet and the chondrogenic pellet is effectively applied to cartilage regeneration therapies. As a result, first, the present inventors have identified that in a case where minicircle vectors expressing the growth factors BMP2 and TGFβ3 are constructed and transduced into stem cells, and the stem cells are induced to differentiate into chondrocytes, the stem cells can effectively differentiate into a chondrogenic pellet. The present inventors have identified that the differentiated chondrogenic pellet can significantly express chondrocyte marker genes and can exhibit a significant cartilage regeneration effect in an osteochondral defect area in a case of being transplanted into the living body.

In addition, the present inventors have identified that in a case where iPSCs are cultured to obtain embryoid bodies, outgrowth cells (OG cells) are produced therefrom, and then the OG cells are isolated by sizes through centrifugation, as the OG cells are smaller in size, higher efficiency of differentiation into a chondrogenic pellet is exhibited, thereby having completed the present invention.

In addition, there is therefore a need for an alternative system that can cover a large portion of the population with minimal cell lines. This alternative system should have a low risk of allograft rejection in a case of being used in many patients. The history of successful transplantation of organs and hematopoietic stem cells has established importance of HLA genes, which is directly related to the individual's immune identity. Banking of ESCs isolated from HLA-homozygous individuals was recommended in the year 2005 to decrease the number of required cell lines. This banking system exclusively requires cells, which are homozygous for only one of HLA-A, -B and -DRB1 haplotypes, from donors. These three subsets of genes are most important in the HLA loci and to decrease possibility of rejection. This strategy was applied to settlement of iPSC banking.

Accordingly, the present inventors have classified the homozygous HLA-A, -B, and -DRB1 types that can maximally cover the (South) Korean population using data from the Catholic Hematopoietic Stem Cell Bank. CBMCs and PBMCs were obtained from donors to produce iPSCs at a clinical level and reprogrammed according to the Good Manufacturing Practice. On the basis of this, the present invention includes a report on the first homozygous iPS cell line in Korea, the report having been made, under the sponsorship of the Korean government, for research and clinical trial.

CITATION LIST

Non-Patent Literature

[NPL 1] Kim Y, Rim Y A, Yi H, Park N, Park S H, Ju J H: The Generation of Human Induced Pluripotent Stem Cells from Blood Cells: An Efficient Protocol Using Serial Plating of Reprogrammed Cells by Centrifugation. *Stem Cells Int* 2016, 2016:1329459.

[NPL 2] Nam Y, Rim Y A, Jung S M, Ju J H: Cord blood cell-derived iPSCs as a new candidate for chondrogenic differentiation and cartilage regeneration. *Stem Cell Res Ther* 2017, 8:16.

[NPL 3] Shu B, Zhang M, Xie R, Wang M, Jin H, Hou W, Tang D, Harris S E, Mishina Y, O'Keefe R J, et al: BMP2, but not BMP4, is crucial for chondrocyte proliferation and maturation during endochondral bone development. *J Cell Sci* 2011, 124:3428-3440.

[NPL 4] Tuli R, Tuli S, Nandi S, Huang X, Manner P A, Hozack W J, Danielson K G, Hall D J, Tuan R S: Transforming growth factor-beta-mediated chondrogenesis of human mesenchymal progenitor cells involves N-cadherin and mitogen-activated protein kinase and Wnt signaling cross-talk. *J Biol Chem* 2003, 278:41227-41236.

[NPL 5] Mueller M B, Tuan R S: Functional characterization of hypertrophy in chondrogenesis of human mesenchymal stem cells. *Arthritis Rheum* 2008, 58:1377-1388.

[NPL 6] Barry F, Boynton R E, Liu B, Murphy J M: Chondrogenic differentiation of mesenchymal stem cells from bone marrow: differentiation-dependent gene expression of matrix components. *Exp Cell Res* 2001, 268:189-200.

[NPL 7] Kim Y I, Ryu J S, Yeo J E, Choi Y J, Kim Y S, Ko K, Koh Y G: Overexpression of TGF-beta1 enhances chondrogenic differentiation and proliferation of human synovium-derived stem cells. *Biochem Biophys Res Commun* 2014, 450:1593-1599.

[NPL 8] Tsuchiya H, Kitoh H, Sugiura F, Ishiguro N: Chondrogenesis enhanced by overexpression of sox9 gene in mouse bone marrow-derived mesenchymal stem cells. *Biochem Biophys Res Commun* 2003, 301:338-343.

[NPL 9] Wang Z H, Li X L, He X J, Wu B J, Xu M, Chang H M, Zhang X H, Xing Z, Jing X H, Kong D M, et al: Delivery of the Sox9 gene promotes chondrogenic differentiation of human umbilical cord blood-derived mesenchymal stem cells in an in vitro model. *Braz J Med Biol Res* 2014, 47:279-286.

[NPL 10] Kim J H, Do H J, Yang H M, Oh J H, Choi S J, Kim D K, Cha K Y, Chung H M: Overexpression of SOX9 in mouse embryonic stem cells directs the immediate chondrogenic commitment. *Exp Mol Med* 2005, 37:261-268.

[NPL 11] Gill D R, Pringle I A, Hyde S C: Progress and prospects: the design and production of plasmid vectors. *Gene Ther* 2009, 16:165-171.

[NPL 12] Bandara N, Gurusinghe S, Chen H, Chen S, Wang L X, Lim S Y, Strappe P: Minicircle DNA-mediated endothelial nitric oxide synthase gene transfer enhances angiogenic responses of bone marrow-derived mesenchymal stem cells. *Stem Cell Res Ther* 2016, 7:48.

DISCLOSURE

Technical Problem

As described above, since cartilage is difficult to regenerate, an effective regenerative treatment method is required. Accordingly, an object of the present invention is to provide a chondrocyte obtained by differentiation induction from stem cells and a method for producing the same.

In addition, another object of the present invention is to provide a pharmaceutical composition for preventing or treating a cartilage defect disease, comprising, as an active ingredient, the chondrocyte obtained by differentiation induction.

Solution to Problem

In order to achieve the above objects, the present invention provides, as a first technical solution, a method for producing chondrocytes obtained by differentiation induction from stem cells, comprising the following steps i) to v):

i) culturing induced pluripotent stem cells (iPSCs) to generate embryoid bodies (EBs);

ii) culturing the EBs generated in step i) in a gelatin-coated medium, to obtain outgrowth cells (OG cells);

iii) transducing the OG cells obtained in step ii) with either or both of a minicircle vector that contains a base sequence encoding BMP2 and a minicircle vector that contains a base sequence encoding TGFβ3;

iv) inducing differentiation of the OG cells transduced in step iii) into chondrocytes; and v) obtaining the chondrocytes produced by differentiation induction in step iv).

In addition, the present invention provides a method for producing chondrocytes obtained by differentiation induction from stem cells, comprising the steps of i) to vi):

i) culturing iPSCs to generate EBs;

ii) culturing the EBs generated in step i) in a gelatin-coated medium, to obtain OG cells;

iii) transducing the OG cells obtained in step ii) with a minicircle vector that contains a base sequence encoding BMP2;

iv) transducing the OG cells obtained in step ii) with a minicircle vector that contains a base sequence encoding TGFβ3;

v) performing mixed culture of the OG cells transduced in step iii) and the OG cells transduced in step iv), so that the OG cells are induced to differentiate into chondrocytes; and vi) obtaining the chondrocytes produced by differentiation induction in step v).

In a preferred embodiment of the present invention, the minicircle vector that contains a base sequence encoding BMP2 may be a non-viral vector, the non-viral vector, (a) containing a gene expression cassette that contains a CMV promoter, a BMP2 gene consisting of the base sequence of SEQ ID NO: 1, and an SV40 polyadenylation sequence; (b) containing the att attachment sequence of bacteriophage lambda, located outside the gene expression cassette of (a); and (c) not containing a replication origin and an antibiotic resistance gene.

In a further preferred embodiment of the present invention, the minicircle vector that contains a base sequence encoding TGFβ3 may be a non-viral vector, the non-viral vector, (a) containing a gene expression cassette that contains a CMV promoter, a TGFβ3 gene consisting of the base sequence of SEQ ID NO: 2, and an SV40 polyadenylation sequence; (b) containing the att attachment sequence of bacteriophage lambda, located outside the gene expression cassette of (a); and (c) not containing a replication origin and an antibiotic resistance gene.

In addition, in a further preferred embodiment of the present invention, the step of inducing differentiation of the OG cells into chondrocytes may be performed by culturing the cells in a medium containing no recombinant growth factor for 3 to 30 days.

In addition, the present invention provides, as a second technical solution, a method for producing chondrocytes obtained by differentiation induction from stem cells, comprising the following steps i) to v):

i) culturing induced pluripotent stem cells (iPSCs) to obtain embryoid bodies;

ii) performing adherent culture of the embryoid bodies obtained in step i), to obtain outgrowth cells (OG cells);

iii) performing centrifugation of the OG cells obtained in step ii) so that the cells are isolated by sizes, and selecting light cells;

iv) inducing differentiation of the light cells selected in step iii) into chondrocytes; and v) obtaining the chondrocytes produced by differentiation induction in step iv).

In a preferred embodiment of the present invention, the induced pluripotent stem cells of step i) may be obtained by reprogramming cord blood mononuclear cells.

In a preferred embodiment of the invention, the adherent culture in step ii) may be performed by culturing the cells on a gelatin-coated plate.

In a preferred embodiment of the present invention, the centrifugation and selection in step iii) may be performed through the following steps a) to c):

a) centrifuging a medium containing the outgrowth cells at 300 rpm to 800 rpm for 3 to 10 seconds, to classify the precipitated cells as heavy cells;

b) centrifuging the supernatant after centrifugation in step a) at 800 rpm to 1,200 rpm for 3 to 10 seconds, to classify the precipitated cells as medium cells; and c) centrifuging the supernatant after centrifugation in step b) at 1,200 rpm to 2,000 rpm for 3 to 10 seconds, to classify the precipitated cells as light cells.

In a preferred embodiment of the present invention, the differentiation induction in step iv) may be carried out in a medium containing human bone morphogenetic protein 2 and human transforming growth factor beta 3, in which the medium may additionally be supplemented with an IGF2 inhibitor.

In addition, the present invention provides, as a third technical solution, a method for producing chondrocytes obtained by differentiation induction from stem cells, comprising the steps of:

i) generating and obtaining embryoid bodies from cord blood mononuclear cell-derived human induced pluripotent stem cells (CBMC-hiPSCs);

ii) generating and obtaining outgrowth cells from the embryoid bodies of step i); and iii) culturing the outgrowth cells of step ii) to obtain a chondrogenic pellet.

According to a preferred embodiment of the present invention, the CBMC-hiPSCs of step i) may be obtained by reprogramming cord blood mononuclear cells.

According to a further preferred embodiment of the present invention, the outgrowth cells of step ii) may be generated by inoculating the embryoid bodies into a gelatin medium.

According to a further preferred embodiment of the present invention, the embryoid bodies may be inoculated at 50 to 70 per $cm^2$ of the gelatin medium.

According to a further preferred embodiment of the present invention, the cord blood mononuclear cell-derived human induced pluripotent stem cells in step i) may be HLA homozygotes.

According to a further preferred embodiment of the present invention, the HLA homozygote may have an HLA homozygous type of Korean.

According to a further preferred embodiment of the present invention, the HLA homozygous type of Korean may be any one selected from the group consisting of HLA-A*33, HLA-B*44, and HLA-DRB1*13.

In addition, the present invention provides a chondrocyte produced by any one of the above methods.

According to a preferred embodiment of the present invention, the composition for differentiation into chondrocytes may be such that expression of at least one gene selected from the group consisting of ACAN, COL2A1, COMP, and SOX9 is increased.

According to a further preferred embodiment of the present invention, the composition for differentiation into chondrocytes may be such that the gene expression level of COL1A1 or COL10 is lower than the gene expression level of COL2A1.

In addition, the present invention provides a pharmaceutical composition for preventing or treating a cartilage damage disease, comprising the chondrocyte as an active ingredient.

In a preferred embodiment of the present invention, the cartilage damage disease may be degenerative arthritis, rheumatoid arthritis, fracture, plantar fasciitis, humerus epicondylitis, calcified myositis, nonunion of fracture, or joint injury caused by trauma.

Advantageous Effects of Invention

Accordingly, the present invention provides a chondrogenic pellet differentiated from induced pluripotent stem cells (iPSCs) with transduction of minicircle vectors encoding the growth factors BMP2 and TGFβ3. The chondrogenic pellet significantly expresses chondrocyte marker genes, in which the chondrocyte marker genes can be expressed at a higher level than in the chondrocytes produced by differentiation induction in a medium supplemented with recombinant growth factors.

In addition, the present invention provides a method for producing chondrocytes, in which outgrowth cells (OG cells) produced from iPSCs are isolated into single unit cells and isolated by sizes through centrifugation, and among these, light OG cells are selected and induced to differentiate into a chondrogenic pellet. In a case where light OG cells are selected and induced to differentiate into a chondrogenic pellet according to the method of the present invention, not only significantly high expression levels of chondrocyte markers are observed as compared with a chondrogenic pellet derived from heavy OG cells, but also a chondrogenic pellet having a histologically stable structure can be generated.

The chondrogenic pellet produced according to the method of the present invention significantly expresses chondrocyte marker genes, in which the chondrocyte marker genes can be expressed at a higher level than in the chondrocytes produced by differentiation induction in a medium supplemented with recombinant growth factors.

In a case where the chondrogenic pellet is transplanted into a cartilage damage area in the living body, cartilage regeneration may be effectively exhibited by the differentiated chondrocytes, and effective cartilage regeneration capacity may be exhibited as compared with a case where chondrocytes produced by differentiation induction with the addition of recombinant growth factors are transplanted. Thus, the chondrogenic pellet can be usefully used for tissue engineering therapies for cartilage regeneration.

In addition, the chondrogenic pellet produced according to the method of the present invention is produced by differentiation induction from CBMC-derived iPSCs. The chondrogenic pellet is an HLA homozygote and has high expression levels of chondrocyte marker genes having types suitable for cartilage transplantation, so that the chondrogenic pellet can be usefully used for preventing, ameliorating, or treating a cartilage-related disease.

BRIEF DESCRIPTION OF DRAWINGS

FIG. 1A illustrates morphological results for the generated CBMC-hiPSC lines;

FIG. 1B illustrates results showing that the CBMC-hiPSCs are stained with alkaline phosphatase;

FIG. 1C illustrates results of relative expression of pluripotency markers in the CBMC-hiPSC lines; and FIG. 1D illustrates results represented by images showing immunofluorescence staining of the generated CBMC-hiPSC lines.

FIG. 2A illustrates a schematic diagram of chondrogenic pellet generation;

FIG. 2B illustrates a morphological result for CBMC-hiPSCs;

FIG. 2C illustrates a morphological result for the generated EBs;

FIG. 2D illustrates a result represented by an image of outgrowth cells derived from EBs attached to a gelatin-coated culture dish; and FIG. 2E illustrates a result showing an image of the chondrogenic pellet.

FIG. 5A illustrates results showing images of the chondrogenic pellet which is stained with antibodies against type 2 collagen and aggrecan, and is harvested at various time points; and FIG. 5B illustrates results showing images of the chondrogenic pellet stained with antibodies against type 1 collagen.

FIG. 6A illustrates results showing expression levels of COL1A1, which is a gene representative of fibroid cartilage, and COL10, which is a hypertrophy marker, at various time points;

FIG. 6B illustrates results showing ratios of COL2A1 to COL1A1 at day 10, day 20, and day 30; and FIG. 6C illustrates results showing relative expression of ACAN, COMP, COL2A1, SOX9, COL1A1, and COL10 in chondrogenic pellets derived from BMSCs and CBMC-hiPSCs at day 30.

FIG. 8A illustrates a schematic diagram of the entire GMP-grade iPSC generation process (in which human leukocyte antigen (HLA) types are screened, cells having a selected HLA type are transferred to a GMP facility, the cells are reprogrammed with iPSCs in the facility, the cells are subjected to various assays for analysis of characteristics, and then a cell line that has passed the assays is established);

FIG. 8B illustrates results of immunofluorescence staining of the generated homozygous IPSCs;

FIG. 8C illustrates a result obtained by identifying a pluripotency marker through a reverse transcription polymerase chain reaction;

FIG. 8D illustrates a result showing an image obtained by alkaline phosphatase staining and the number of positive iPSC colonies;

FIG. 8E illustrates a result of normal karyotype for the generated iPSCs; and

FIG. 8F illustrates results obtained by immunofluorescence staining of iPSCs differentiated into three germ layers.

FIG. 9A illustrates a schematic diagram showing a construction process of minicircle vectors for expression of BMP2 and TGFβ3; and FIG. 9B illustrates results which identify sizes of a minicircle vector (mcBGF2) that contains a gene encoding BMP2 and a minicircle vector (mcTGFβ3) that contains a gene encoding TGFβ3.

FIG. 10A illustrates photographs, taken by a fluorescence microscope, which identify an expression level of RFP following transduction of mcBAMP2 or mcTGFβ3 into HEK293T cells;

FIG. 10B illustrates a result which identifies percentage of cells into which mcBAMP2 or mcTGFβ3 has been transduced;

FIG. 10C illustrates a result which compares a relative expression level of BAMP2 in HEK293T cells into which mcBAMP2 or mcTGFβ3 has been transduced; and FIG. 10D illustrates a result which compares a relative expression level of TGFβ3 in HEK293T cells into which mcBAMP2 or mcTGFβ3 has been transduced.

FIG. 11A illustrates a schematic diagram of a process of inducing iPSCs to differentiate into a chondrogenic pellet;

FIGS. 11B to 11E illustrate morphology of iPSC colonies (FIG. 11B), embryoid bodies (FIG. 11C), OG cells obtained by performing adherent culture of EBs on a gelatin container (FIG. 11D), and OG cells before transduction (FIG. 11E), in the differentiation induction process; and FIGS. 11F to 11H illustrate photographs, taken by a fluorescence microscope, which identify expression of RFP in OG cells into which minicircle vectors have been transduced.

FIG. 12A illustrates percentage of OG cells into which the minicircle vectors have been transduced;

FIGS. 12B to 12F illustrate results obtained by identifying expression levels of mesenchymal stem cell marker genes in the OG cells into which the minicircle vectors have been transduced; and FIGS. 12G to 12I illustrate results obtained by performing alizarin red staining (FIG. 12G), oil red O staining (FIG. 12H), and alcian blue staining (FIG. 12I) of the OG cells into which the minicircle vectors have been transduced.

FIG. 13A illustrates morphology of cells 5 days after transduction of mcBAMP2 or mcTGFβ3; and FIGS. 13B to 13E illustrate results obtained by identifying expression levels of RFP, 5 days (FIG. 13B), 10 days (FIG. 13C), 20 days (FIG. 13D), and 30 days (FIG. 13E) after initiation of differentiation induction following transduction of mcBAMP2 or mcTGFβ3. Results of GFP were checked to identify fluorescence intensity which is spontaneously expressed in a three-dimensionally cultured chondrogenic pellet.

FIGS. 15A to 15C illustrate results obtained by performing alcian blue staining (FIG. 15A), safranin O staining (FIG. 15B), and toluidine blue staining (FIG. C) of the chondrogenic pellet; and FIGS. 15D and 15E illustrate results which identify production levels of collagen expressed in the chondrogenic pellet.

FIG. 16A illustrates a schematic diagram showing a process in which the chondrogenic pellet is transplanted into an osteochondral defect model mouse in order to identify in vivo cartilage regeneration capacity thereof;

FIGS. 16B to 16D illustrate results obtained by transplanting the chondrogenic pellet produced by differentiation induction with transduction of minicircle vectors, and, after 4 weeks, identifying the osteochondral defect area with alcian blue staining (FIG. 16B), toluidine blue staining (FIG. 16C), and safranin staining (FIG. 16D); and FIG. 16E illustrates a result obtained by identifying, with the ICRS score, a regeneration degree of cartilage following transplantation of the chondrogenic pellet into which minicircle vectors have been transduced.

FIGS. 18A and 18B illustrate results obtained by observing morphology of heavy OG cells, medium OG cells, and light OG cells, after isolation and in adherent culture;

FIGS. 18C to 18E illustrate results obtained by identifying gene expression levels of SOX9 and COL10 in the heavy OG cells, the medium OG cells, and the light OG cells; and FIGS. 18F and 18G illustrate results obtained by identifying protein expression levels of SOX9 and COL10 in the heavy OG cells, the medium OG cells, and the light OG cells.

FIG. 19A illustrates morphology of chondrogenic pellets produced by inducing differentiation of OG cells, which have been isolated by sizes, by being cultured in a chondrogenic differentiation medium; and FIG. 19B illustrates results obtained by identifying, through histological staining, osteogenic capacity of the obtained chondrogenic pellets.

FIG. 23A illustrates morphology of a chondrogenic pellet produced by differentiation induction with treatment with 2 mM chromeceptin; and FIG. 23B illustrates results obtained by identifying gene expression levels of COL2A1 and SOX9 in the thus differentiated chondrogenic pellet.

DETAILED DESCRIPTION OF INVENTION

Figure 1:
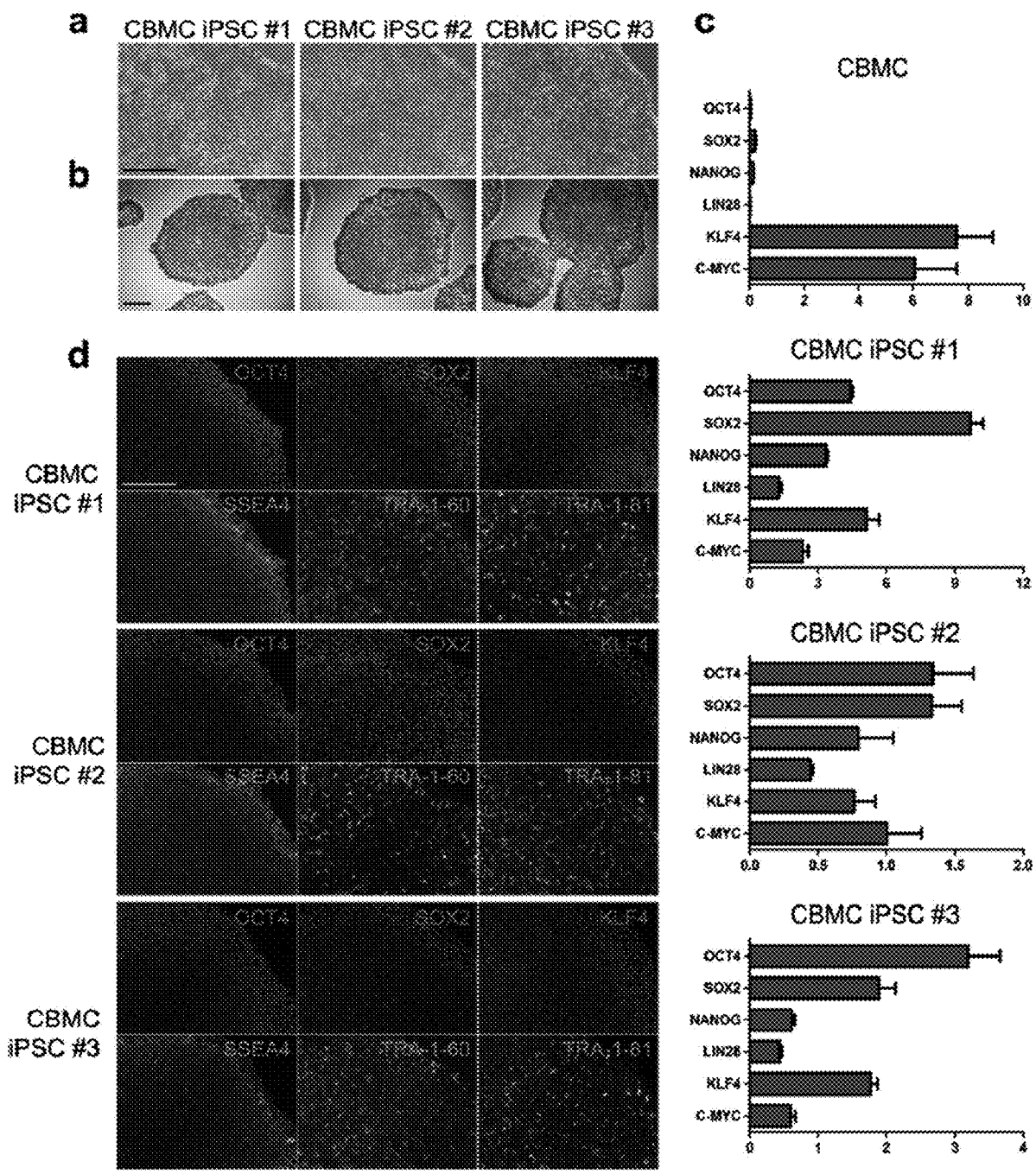
FIGS. 1A-1D illustrate results for characteristics of three CBMC-hiPSC lines.

Hereinafter, the present invention will be described in detail.

In the field of regenerative medicine, techniques for inducing differentiation into chondrocytes through cell therapy techniques are widely used for cartilage regeneration. However, a therapeutic effect may vary depending on characteristics of differentiation capacity and tissue-forming capacity of chondrocytes to be transplanted into the body. For this purpose, a technique for inducing differentiation into induced pluripotent stem cell-derived chondrocytes is required, and studies for the purpose of improving differentiation efficiency and tissue-forming capacity of differentiated chondrocytes are continuing.

Accordingly, the present invention provides a method for producing chondrocytes obtained by differentiation induction from stem cells, comprising the following steps i) to v):

i) culturing induced pluripotent stem cells (iPSCs) to generate embryoid bodies (EBs);

ii) culturing the EBs generated in step i) in a gelatin-coated medium, to obtain outgrowth cells (OG cells);

iii) transducing the OG cells obtained in step ii) with either or both of a minicircle vector that contains a base sequence encoding BMP2 and a minicircle vector that contains a base sequence encoding TGFβ3;

iv) inducing differentiation of the OG cells transduced in step iii) into chondrocytes; and v) obtaining the chondrocytes produced by differentiation induction in step iv).

In addition, the present invention provides a method for producing chondrocytes obtained by differentiation induction from stem cells, comprising the steps of i) to vi):

i) culturing iPSCs to generate EBs;

ii) culturing the EBs generated in step i) in a gelatin-coated medium, to obtain OG cells;

iii) transducing the OG cells obtained in step ii) with a minicircle vector that contains a base sequence encoding BMP2;

iv) transducing the OG cells obtained in step ii) with a minicircle vector that contains a base sequence encoding TGFβ3;

v) performing mixed culture of the OG cells transduced in step iii) and the OG cells transduced in step iv), so that the OG cells are induced to differentiate into chondrocytes; and vi) obtaining the chondrocytes produced by differentiation induction in step v).

In addition, the present invention provides a chondrogenic pellet produced by any one of the above methods.

In the method for producing chondrocytes of the present invention, the iPSCs in step i) may be derived from patient-derived cells, or may be commercially available. However, in a process of intending to improve biocompatibility in transplanting the chondrocytes of the present invention into an osteochondral defect area, it is more preferable that the iPSCs be derived from patient-derived cells.

In the method for producing chondrocytes of the present invention, it is more preferable that the OG cells obtained in step ii) be isolated and obtained in single unit cells. However, the present invention is not limited thereto. In order to obtain the cells in single unit cells, embryoid bodies can be isolated using a cell strainer or the like. It is preferable that OG cells as single cells obtainable in the production method of the present invention represent fibrous morphology similar to mesenchymal stem cells.

In the method for producing chondrocytes of the present invention, it is preferable that the OG cells into which the minicircle vectors have been transduced be induced to differentiate into a chondrogenic pellet by being cultured in a chondrogenic differentiation medium for 3 to 30 days. Specifically, it is more preferable that the differentiation induction be performed by being cultured for 5 to 20 days. However, the present invention is not limited thereto. In the differentiation induction, it is preferable that the chondrogenic differentiation medium not further contain a recombinant growth factor.

Therefore, the chondrogenic pellet produced by differentiation from induced pluripotent stem cells into which minicircle vectors encoding the growth factors BMP2 and TGFβ3 have been transduced, which is provided in the present invention, significantly expresses chondrocyte marker genes, in which the chondrocyte marker genes can be expressed at a higher level than in the chondrocytes produced by differentiation induction in a medium supplemented with recombinant growth factors.

In a case where the chondrogenic pellet is transplanted into a cartilage damage area in the living body, cartilage regeneration may be effectively exhibited by the differentiated chondrocytes, and an effective cartilage regeneration capacity may be exhibited as compared with a case where chondrocytes produced by differentiation induction with the addition of recombinant growth factors are transplanted. Thus, the chondrogenic pellet can be usefully used for tissue engineering therapies for cartilage regeneration.

Accordingly, the present invention provides a method for producing chondrocytes obtained by differentiation induction from stem cells, comprising the following steps i) to v):

i) culturing induced pluripotent stem cells (iPSCs) to obtain embryoid bodies;

ii) performing adherent culture of the embryoid bodies obtained in step i), to obtain outgrowth cells (OG cells);

iii) performing centrifugation of the OG cells obtained in step ii) so that the cells are isolated by sizes, and selecting light cells;

iv) inducing differentiation of the light cells selected in step iii) into chondrocytes; and v) obtaining the chondrocytes produced by differentiation induction in step iv).

In addition, the present invention provides a chondrocyte produced by the above method.

In addition, in the method for producing chondrocytes of the present invention, the "centrifugation" in step iii) is carried out with the intention of selecting light outgrowth cells (OG cells). For this purpose, it is preferable that the OG cells obtained in step ii) be used in a state of being isolated into single unit cells by removal of cell masses. As such, in a case of being isolated into single unit cells, it is expectable that the respective cells can be significantly isolated by sizes. In a case of embryoid bodies cultured in an aggregated form, in order to isolate the same into single unit cells, it is possible to achieve isolation by a conventional method such as using a cell strainer.

In the method for producing chondrocytes of the present invention, it is preferable that the "centrifugation" and "selection" in step iii) be carried out through the following steps a) to c):

a) centrifuging a medium containing the outgrowth cells at 300 rpm to 800 rpm for 3 to 10 seconds, to classify the precipitated cells as heavy cells;

b) centrifuging the supernatant after centrifugation in step a) at 800 rpm to 1,200 rpm for 3 to 10 seconds, to classify the precipitated cells as medium cells; and c) centrifuging the supernatant after centrifugation in step b) at 1,200 rpm to 2,000 rpm for 3 to 10 seconds, to classify the precipitated cells as light cells.

Specifically, for conditions of the above-mentioned "centrifugation", it is preferable to perform centrifugation at 500 rpm for 5 seconds in step a); it is preferable to perform centrifugation at 1,100 rpm for 5 seconds in step b); and it is more preferable to perform centrifugation at 1,500 rpm for 5 seconds in step c). However, the present invention is not limited thereto. In the method of the present invention, from the viewpoint that light OG cells are selected and induced to differentiate into chondrocytes, modification can be made so that the step a) is omitted and only the step b) is performed, and then a step of classifying the cells as light cells is performed through the step c) using the supernatant after centrifugation. However, the present invention is not limited thereto, and the method of the present invention can be applied without limitation as long as the method is a method that belongs to a scope which can be understood by a person skilled in the art to be capable of selecting only light cells.

In the method of the present invention, the "induced pluripotent stem cells" of step i) may be derived from patient-derived cells, or may be commercially available. However, from the viewpoint that it is intended to enhance biocompatibility in transplanting the chondrocytes of the present invention into an osteochondral defect area, it is more preferable to use, as the iPSCs, those induced from the patient-derived cells. Specifically, it is most preferable to use, as the iPSCs, those obtained by reprogramming the patient's cord blood mononuclear cells. However, the present invention is not limited thereto.

In the method of the present invention, the "adhesion culture" in step ii) may be such that the cells are cultured on a gelatin-coated plate.

In the method of the present invention, it is preferable that the "inducing differentiation" in step iv) be performed in a medium containing human bone morphogenetic protein 2 and human transforming growth factor beta 3. However, the present invention is not limited thereto. Differentiation inducing factors known as factors capable of inducing differentiation of stem cells into chondrocytes may be optionally added to or subtracted from the medium. In addition, the medium may further contain an IGF2 inhibitor. As the IGF2 inhibitor, chromeceptin may be typically mentioned.

In a case where light outgrowth cells are selected and induced to differentiate into chondrocytes according to the method of the present invention, not only significantly high expression levels of chondrocyte markers are observed as compared with a chondrogenic pellet derived from heavy OG cells, but also a chondrogenic pellet having a histologically stable structure can be generated. Therefore, in the method in which only light cells are selected and induced to differentiate into chondrocytes so that the chondrocytes are produced, according to the method of the present invention, not only differentiation efficiency which induces differentiation of stem cells into chondrocytes can be improved as compared with a conventional method, but also quality of differentiated chondrocytes can be improved. Thus, such a method can be usefully used in the treatment of a cartilage damage disease in regenerative medicine.

In addition, the present invention provides a chondrocyte produced by the method of the present invention.

In addition, the present invention provides a pharmaceutical composition for preventing or treating a cartilage damage disease, comprising the chondrocyte as an active ingredient.

In the pharmaceutical composition of the present invention, the cartilage damage disease may be preferably at least one selected from the group consisting of degenerative arthritis, rheumatoid arthritis, fracture, plantar fasciitis, humerus epicondylitis, calcified myositis, nonunion of fracture, or joint injury caused by trauma. However, the present invention is not limited thereto, and any disease known in the art as a disease of cartilage area which may be caused by a cartilage defect or damage can be included without limitation.

A therapeutically effective amount of the composition of the present invention may vary depending on a variety of factors, such as method of administration, target site, and the patient's condition. Therefore, in a case of being used in the human body, the dosage should be determined to an appropriate amount, taking into consideration together with safety and effectiveness. It is also possible to estimate an amount to be used in humans from the effective amount determined through animal experiments. Such considerations in determining the effective amount are described, for example, in Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition of the present invention may also contain carriers, diluents, excipients, or a combination of two or more thereof, commonly used in biological preparations. Pharmaceutically acceptable carriers are not particularly limited as long as they are suitable for in vivo delivery of the composition. As such pharmaceutically acceptable carriers, for example, compounds described in Merck Index, 13th ed., Merck & Co. Inc., saline, sterile water, Ringer's solution, buffered saline, dextrose solution, maltodextrin solution, glycerol, ethanol, and a mixture of one or more thereof can be used, and if necessary, other typical additives such as antioxidants, buffers, and bacteriostatic agents can be added thereto. Furthermore, the composition can be preferably made into preparations, depending on respective diseases or ingredients, using appropriate methods in the art or methods disclosed in Remington's Pharmaceutical Science (Mack Publishing Company, Easton Pa., 18th, 1990).

Hereinafter, the present invention will be described in more detail by way of examples.

It will be apparent to those skilled in the art that these examples are given to merely illustrate the present invention and that the scope of the present invention is not construed as being limited by these examples.

[Experimental Methods]

Hereinafter, specific experimental methods performed for the examples of the present invention will be described. The following experimental methods indicate some methods of carrying out the examples of the present invention and may be optionally changed by a person having ordinary skill in the art.

1) Isolation of CBMCs

CBMCs were acquired from the Cord Blood Bank at Seoul ST. Mary's Hospital. Cord blood was diluted with phosphate buffered saline (PBS) and centrifuged at 850×g for 30 minutes through a Ficoll gradient. CBMCs were collected, washed, and frozen. The frozen CBMCs were thawed and resuspended in StemSpan medium (STEMCELL Technological, Vancouver, British Columbia, Canada) supplemented with CC110 cytokine cocktail (STEMCELL) before use. Before reprogramming, the cells were kept for 5 days at 37° C. in 5% $CO_2$.

2) Blood Samples and Ethics Regulations

The present study was approved by the Institutional Review Board (IRB) of the Catholic University of Korea.

3) Reprogramming Using Sendai Virus

Reprogramming refers to a process by which epigenetic marks are changed in the course of mammalian development. In general, reprogramming of induced pluripotent stem cells refers to a technique of inducing pluripotent stem cells by artificially overexpressing factors necessary for reprogramming in somatic cells. The method for overexpressing genes includes using viruses, plasmid vectors, mRNAs, proteins, or the like.

CBMCs were seeded onto a 24-well plate at a concentration of $3\times10^5$. Reprogramming was induced using the CytoTune-iPS Sendai Reprogramming kit. Infection was performed with a multiplicity of infection of 7.5 per $3\times10^5$ cell infectious unit. After addition of viral components, the cells were centrifuged for 30 minutes at a condition of 1,160×g and 35° C., and then incubated at 37° C. in 5% $CO_2$. Next day, the cells were transferred to a 12-well plate coated with vitronectin (Life Technologies) and precipitated by performing centrifugation for 10 minutes at 1,160×g and 35° C. After the centrifugation, TeSR-E8 medium (STEMCELL) was added thereto at a ratio of 1:1. The reprogrammed cells were kept and expanded in TeSR-E8 medium with daily medium replacement.

4) Staining with Alkaline Phosphatase

In order to obtain colonies large enough to be stained, the cells were inoculated, at a concentration of $2\times10^3$, into a 6-well plate coated with vitronectin, and expanded for 5 to 7 days. Staining of undifferentiated iPSC colonies was performed using an alkaline phosphatase detection kit (Millipore, Billerica, Mass., USA). The cells were washed with PBS containing 0.05% Tween-20 and fixed with 4% paraformaldehyde for 2 minutes. Fast Red Violet, Naphthol AS-BI phosphate solution, and water were mixed at a ratio of 2:1:1 to prepare a staining reagent. The cells were washed twice with PBST. Treatment with the staining solution mixture was performed at room temperature (RT) for 15 minutes. After incubation, the cells were washed with PBST and covered with PBS to prevent drying. The stained colonies were measured with a microscope.

5) Immunocytochemical Staining

In order to obtain iPSC colonies large enough to be stained, the cells were inoculated, at a concentration of $2\times10^3$, into a 6-well plate coated with vitronectin. In order to induce iPSC colonies, the cells were expanded for 5 to 7 days with daily medium replacement. After the expansion, the iPSCs were washed with PBS and fixed with 4% paraformaldehyde. The cells were permeabilized with 0.1% Triton X-100 (BIOSESANG) for 10 minutes. After the infiltration, the cells were blocked with PBS (PBA) containing 2% bovine serum albumin (BSA; Sigma Aldrich, St. Louis, Mo., USA) for 30 minutes at room temperature. Primary antibodies were diluted in PBA in the following dilution proportions: OCT4 (1/100; Santa Cruz, Calif., USA), KLF4 (1/250; Abcam, Cambridge, UK), SOX2 (1/100; BioLegend, San Diego, Calif., USA), TRA-1-60 (1/100; Millipore), TRA-1-81 (1/100; Millipore), and SSEA4 (1/200; Millipore). Incubation with the primary antibodies was performed at room temperature for 2 hours. Alexa Fluor 594- (1/400; Life Technologies) and 488- (1/400; Life Technologies) conjugated secondary antibodies were diluted with PBA and incubation therewith was performed for 1 hour at room temperature while avoiding light. The cells were washed and mounted using ProLong Antifade mounting reagent (Thermo Fisher Scientific, Waltham, Mass., USA). The stained colonies were detected with an immunofluorescence microscope.

6) Polymerase Chain Reaction Using CBMC-iPSC Sample $5 \times 10^5$ iPSCs were harvested and frozen at −20° C. Total mRNA was extracted therefrom using Trizol (Life Technologies) and cDNA was synthesized using RevertAid™ First Strand cDNA Synthesis Kit (Thermo Fisher Scientific). The synthesized cDNA was used to perform reverse transcriptase polymerization. Primer sequences are shown in [Table 1] below.

TABLE 1

Primer sequences for translocation markers used in real-time RT-PCR

| Target Name | Direction | Primer Sequence | Size |
|---|---|---|---|
| OCT3/4 | Forward | ACCCCTGGTGCCGTGAA | 190 |
|  | Reverse | GGCTGAATACCTTCCCAAATA |  |
| SOX2 | Forward | CAGCGCATGGACAGTTAC | 321 |
|  | Reverse | GGAGTGGGAGGAAGAGGT |  |
| NANOG | Forward | AAAGGCAAACAACCCACT | 270 |
|  | Reverse | GCTATTCTTCGGCCAGTT |  |
| LIN28 | Forward | GTTCGGCTTCCTGTCCAT | 122 |
|  | Reverse | CTGCCTCACCCTCCTTCA |  |
| DPPB5 | Forward | CGGCTGCTGAAAGCCATTTT | 215 |
|  | Reverse | AGTTTGAGCATCCCTCGCTC |  |
| TDGF1 | Forward | TCCTTCTACGGACGGAACTG | 140 |
|  | Reverse | AGAAATGCCTGAGGAAAGCA |  |
| GAPDH | Forward | GAATGGGCAGCCGTTAGGAA | 414 |
|  | Reverse | GACTCCACGACGTACTCAGC |  |

7) Karyotyping

Cells were cultured until confluency reached about 80%. A chromosome resolution additive (Genial Genetic Solutions, Runcorn, UK) was added to each well. After incubation, treatment with Colcemid® was performed for 30 minutes. The cells were harvested and treated with a preheated stock solution to become a solution. The resultant was fixed with a mixture obtained by mixing acetic acid and a methanol solution at a ratio of 1:3. Slides were prepared for chromosome analysis using the trypsin-Giemsa banding technique.

8) Functional Identification of iPSCs

A kit for identifying human pluripotent stem cell function (R&D, Minneapolis, Minn., USA) was purchased to evaluate differentiation capacities of three germ layers. The day before the experiment, a culture dish was coated with Cultrex PathClear BME (R&D) according to the manufacturer's instructions. A medium specific to each germ layer was prepared and cells were cultured individually. After differentiation, the cells were washed with PBS and fixed with 4% paraformaldehyde. Permeation and blocking were performed with 0.3% Triton X-100 and 1% PBA for 45 minutes. Antibodies against Otx2 (1/10, ectoderm), Brachyury (1/10 mesoderm), and Sox17 (1/10, endoderm) were diluted. The antibodies were suspended in PBA and incubation therewith was performed at room temperature for 3 hours.

After washing the primary antibodies, Alexa Fluor 568 donkey anti-goat secondary antibodies (1:200; R&D) were diluted with PBA and incubation therewith was performed for 1 hour. The cells were washed with PBA, and treatment with a DAPI solution was performed at room temperature for 10 minutes. The cells were washed and covered with PBS. The staining results were checked using a fluorescence microscope.

9) EB-Derived Outgrowth Cell Induction

CBMC-hiPSCs were expanded and $2 \times 10^6$ cells were prepared. The cells were resuspended in Aggrewell medium (STEMCELL) and seeded on a 100-mm culture dish. The cells were cultured for one day at 37° C. in 5% $CO_2$. Next day, the medium was replaced with TeSR-E8 medium and the cells were kept expanded for 6 days. After the expansion process, EBs were harvested and resuspended in DMEM containing 20% fetal bovine albumin (FBS). The resultant was placed on a gelatin-coated dish to induce outgrowth cells. The cells were kept for one week at 37° C. in 5% $CO_2$ prior to chondrogenic differentiation.

10) Chondrogenic Differentiation Using EB-Derived Outgrowth Cells

The outgrowth cells derived from the EBs were washed and separated from the culture dish. The cells were passed through a 40 μm cell strainer (Thermo Fisher Scientific) to remove cell masses. Single outgrowth cells were counted and $3 \times 10^5$ cells per chondrogenic pellet were prepared. $3 \times 10^5$ outgrowth cells were cultured in a chondrogenic differentiation medium (DMEM, 20% knockout serum replacement, lx non-essential amino acids, 1 mM L-glutamine, 1% sodium pyruvate, 1% ITS+Premix, $10^{-7}$M dexamethasone, 50 μm ascorbic acid, 40 μg/mL of L-proline, supplemented with 50 ng/mL of human bone morphogenetic protein 2, and 10 ng/mL of human transforming growth factor beta 3), and transferred to a conical tube. The cells were centrifuged at 750×g for 5 minutes. The resulting chondrogenic pellet was kept for 30 days and replacement of the culture medium was performed daily. BMSCs were used as a positive control.

11) Histological Analysis of Chondrogenic Pellet

The chondrogenic pellet was fixed with 4% paraformaldehyde at room temperature for 2 hours. One layer of gauze was placed on a cassette and the pellet was transferred to the gauze. Dehydration was performed sequentially with an ethanol solution. The dehydration solution was removed with a mixture of graded ethanol and zylene (Duksan Pure Chemical Co., Ltd., Ansan, Korea) and paraffin infiltration was performed overnight. Next day, the pellet was immobilized on a paraffin block and a 7 μm section was obtained using a microtome. The slide was dried at 60° C. for 2 hours. The section was deparaffinized with 2 cycles of zylene. The section was rehydrated with decreasing sequential ethanol series and washed with tap water for 5 minutes.

For alcian blue staining, the section was incubated in 1% alcian blue solution for 30 minutes. Then, the slide was washed and counter-stained with nuclear fast red for 1 minute. Safranin O staining was performed by incubating the slide in Weigert's iron hematoxylin for 10 minutes. Slide was washed and incubated in 0.1% safranin O solution for 5 minutes.

For toluidine staining, the section was incubated in toluidine blue solution for 4 minutes. After the staining process, the section was washed and passed through increasing sequential ethanol series. Ethanol was removed with 2 cycles of zylene and the slide was fixed using VectaMount™ Permanent Mounting Medium (VectorLaboratories). Staining was checked with a microscope.

12) Immunohistochemistry

The section was dried at 60° C. for 2 hours and deparaffinized with 2 cycles of zylene. The section was rehydrated with decreasing sequential ethanol series and washed with tap water for 5 minutes. Antigen unmasking was induced by incubation in citrate buffer for 15 minutes and cooling for 20 minutes. The cooled section was washed twice with deionized water (DW). Activity of endogenous peroxidase was blocked by incubating the section in 3% hydrogen peroxide diluted in DW for 10 minutes. The section was washed twice with DW and then further washed with Tris buffered saline (TBS) containing 0.1% Tween-20 (TBST). The section was blocked with TBS containing 1% BSA at room temperature for 20 minutes. Primary antibodies diluted in blocking solution were added to the section and incubation was performed overnight at 4° C. The primary antibodies were diluted in the following proportions: type 1 collagen (1/100, Abcam), type 2 collagen (1/100, Abcam), and aggrecan (1/100, GeneTex, Irvine, Calif., USA). A negative control slide was treated with the same amount of blocking solution containing no antibody. Next day, the section was washed three times for 3 minutes each in TBST, and incubation with secondary antibodies (1/200) was performed at room temperature for 40 minutes. The section was washed with TBST and ABC reagent and incubated for 30 minutes. The slide was washed 3 times with TBST and a DAB solution (Vector Laboratories) was applied for 1 minute. The section was washed with DW until the color was washed away. Mayer's hematoxylin was applied to the section for 1 minute for counter staining. The section was washed and passed through increasing sequential ethanol series. Ethanol was removed with two cycles of zylene and the slide was mounted using VectaMount™ Permanent Mounting Medium (Vector Laboratories). Staining was checked with a bright-field microscope.

13) Polymerase Reaction of Chondrogenic Pellet 10 chondrogenic pellets were harvested at each time point and frozen at −80° C. The samples were rapidly frozen with liquid nitrogen and ground with pestle and mortar. Each of the ground pellet samples was incubated with Trizol for mRNA extraction. cDNA was synthesized from the extracted mRNA, and polymerase chain reaction was performed with primers for cell-specific markers. Primer sequences for RT-PCR are shown in [Table 2]. Primer sequences for real-time PCR are shown in [Table 3] below. The mean cycle threshold obtained from triplicate experiments was used to calculate gene expression so as to average GAPDH as an internal control.

TABLE 2

Primer sequences used in RT-PCR for amplification of chondrogenic markers

| Target Name | Direction | Primer Sequence | Size |
|---|---|---|---|
| SOX9 | Forward | GAACGCACATCAAGACGGAG | 631 |
| | Reverse | TCTCGTTGATTTCGCTGCTC | |

TABLE 2-continued

Primer sequences used in RT-PCR for amplification of chondrogenic markers

| Target Name | Direction | Primer Sequence | Size |
|---|---|---|---|
| ACAN | Forward | TGAGGAGGGCTGGAACAAGTACC | 349 |
| | Reverse | GAGGTGGTAATTGCAGGGAACA | |
| COL2A1 | Forward | TTCAGCTATGGAGATGACAATC | 472 |
| | Reverse | AGAGTCCTAGAGTGACTGAG | |
| COMP | Forward | CAACTGTCCCCAGAAGAGCAA | 588 |
| | Reverse | TGGTAGCCAAAGATGAAGCCC | |
| COL1A1 | Forward | CCCCTGGAAAGAATGGAGATG | 148 |
| | Reverse | TCCAAACCACTGAAACCTCTG | |
| COL10 | Forward | CAGTCATGCCTGAGGGTTTT | 196 |
| | Reverse | GGGTCATAATGCTGTTGCCT | |
| GAPDH | Forward | GAATGGGCAGCCGTTAGGAA | 414 |
| | Reverse | GACTCCACGACGTACTCAGC | |

TABLE 3

Primer sequences used in real-time PCR for amplification of chondrogenic markers

| Target Name | Direction | Primer Sequence | Size |
|---|---|---|---|
| SOX9 | Forward | TTCCGCGACGTGGACAT | 77 |
| | Reverse | TCAAACTCGTTGACATCGAAGGT | |
| ACAN | Forward | AGCCTGCGCTCCAATGACT | 107 |
| | Reverse | TAATGGAACACGATGCCTTTCA | |
| COL2A1 | Forward | GGCAATAGCAGGTTCACGTACA | 79 |
| | Reverse | CGATAACAGTCTTGCCCCACTTA | |
| COMP | Forward | AGCAGATGGAGCAAACGTATTG | 76 |
| | Reverse | ACAGCCTTGAGTTGGATGCC | |
| COL1A1 | Forward | CCCCTGGAAAGAATGGAGATG | 148 |
| | Reverse | TCCAAACCACTGAAACCTCTG | |
| COL10 | Forward | CAGTCATGCCTGAGGGTTTT | 196 |
| | Reverse | GGGTCATAATGCTGTTGCCT | |

[Example 1] Production of hiPSCs Using Isolated CBMCs

Reprogramming of CBMCs was facilitated using sendai virus containing a Yamanaka factor. The Yamanaka factor is a gene capable of inducing pluripotency. Some time after transduction, CBMC-hiPSCs formed a colony similar to embryonic stem cells (FIG. 1A). The CBMC-hiPSCs were purified into a cell line with the same cell morphology. The same CBMC-hiPSCs were used for further characterization. The established CBMC-hiPSCs were stained with alkaline phosphate (FIG. 1B). Expression of pluripotency makers including OCT4, SOX2, NANOG, LIN28, KLF4, and c-MYC was also measured (FIG. 1C). The parental CBMCs were used as a negative control. Expression of OCT4, SOX2, NANOG, and LIN28 was increased in the CBMC-hiPSCs. However, low expression of KLF4 and c-MYC was observed in the CBMC-hiPSCs as compared with the CBMCs. Typical cell surface markers (SSEA4, OCT4, SOX2, KLF4, TRA-1-80, and TRA-1-60) were identified by immunochemical analysis (FIG. 1D). All differentiated cell lines expressed markers which become standards for pluripotency. It was identified that the CBMC-hiPSCs maintain their normal karyotype even after the reprogramming process and also differentiate into various germ cells. These data indicate that CBMC-hiPSCs have been successfully produced and have pluripotency.

[Example 2] Differentiation of CBMC-iPSCs into Chondrocytes

Figure 2:
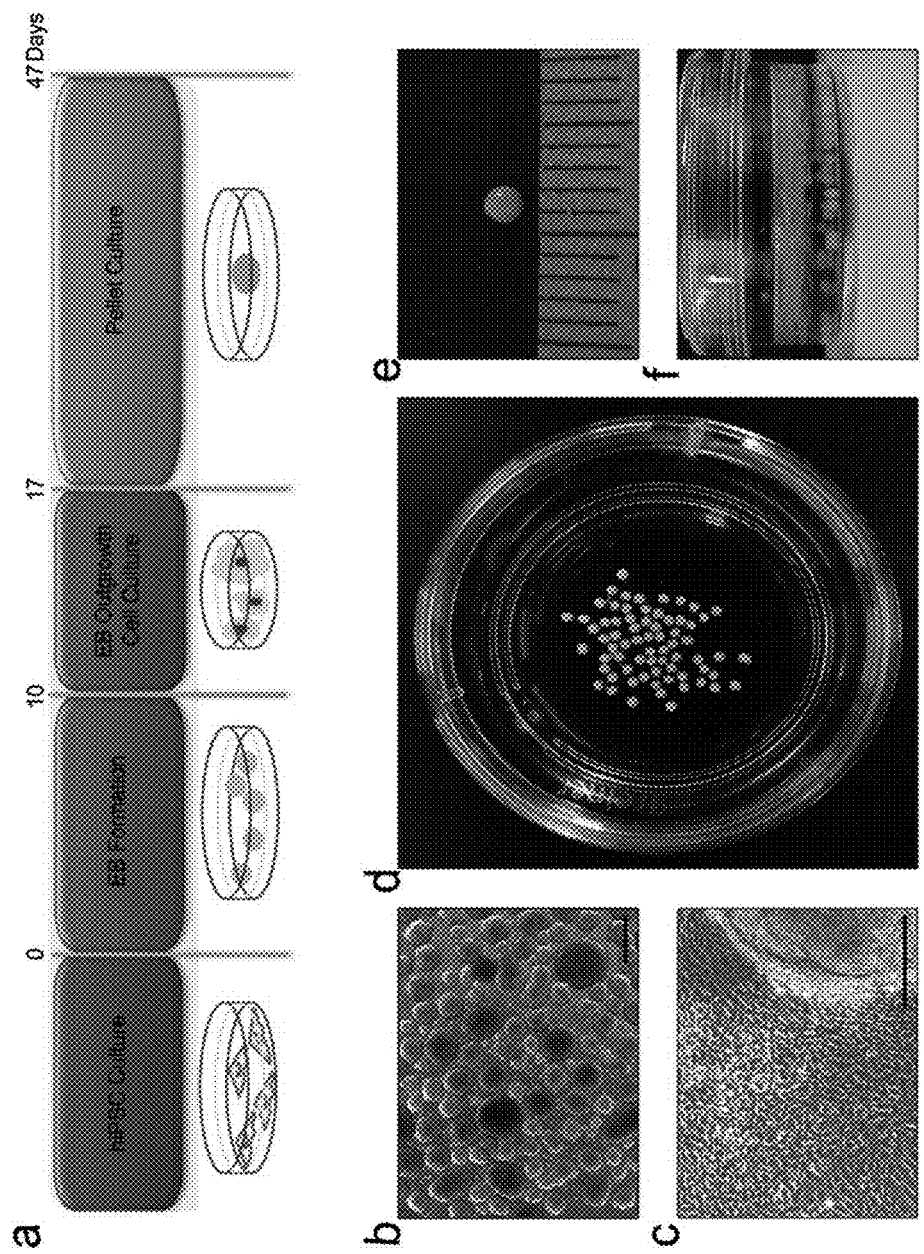
FIGS. 2A-2E illustrate results of chondrogenic pellet generation using CBMC-hiPSCs.

In order to check cartilage regeneration capacity of CBMC-iPSCs, chondrogenic differentiation was performed through culture of EBs and induction of outgrowth cells. A simple scheme for a chondrogenic pellet production process is as illustrated in FIG. 2A. CBMC-iPSCs colonies were prepared for chondrogenic differentiation (FIG. 2B). The CBMC-iPSCs were expanded and aggregated into EBs (FIG. 2C). The EBs were expanded for several days and transferred to a gelatin-coated culture dish so as to be induced to outgrowth cells (FIG. 2D). The outgrowth cells were expanded and were isolated into single cells for differentiation into chondrocytes. $2 \times 10^6$ iPSCs were used to obtain a number of chondrogenic pellets. After 30 days of differentiation, the chondrogenic pellets were generated using the EB outgrowth cells. The generated chondrogenic pellets exhibited a three-dimensional spheroidal shape. From the above, it was identified that CBMC-hiPSCs can differentiate into chondrocytes and can form a cartilage shape having a spheroidal shape due to accumulation of ECM.

Figure 3:
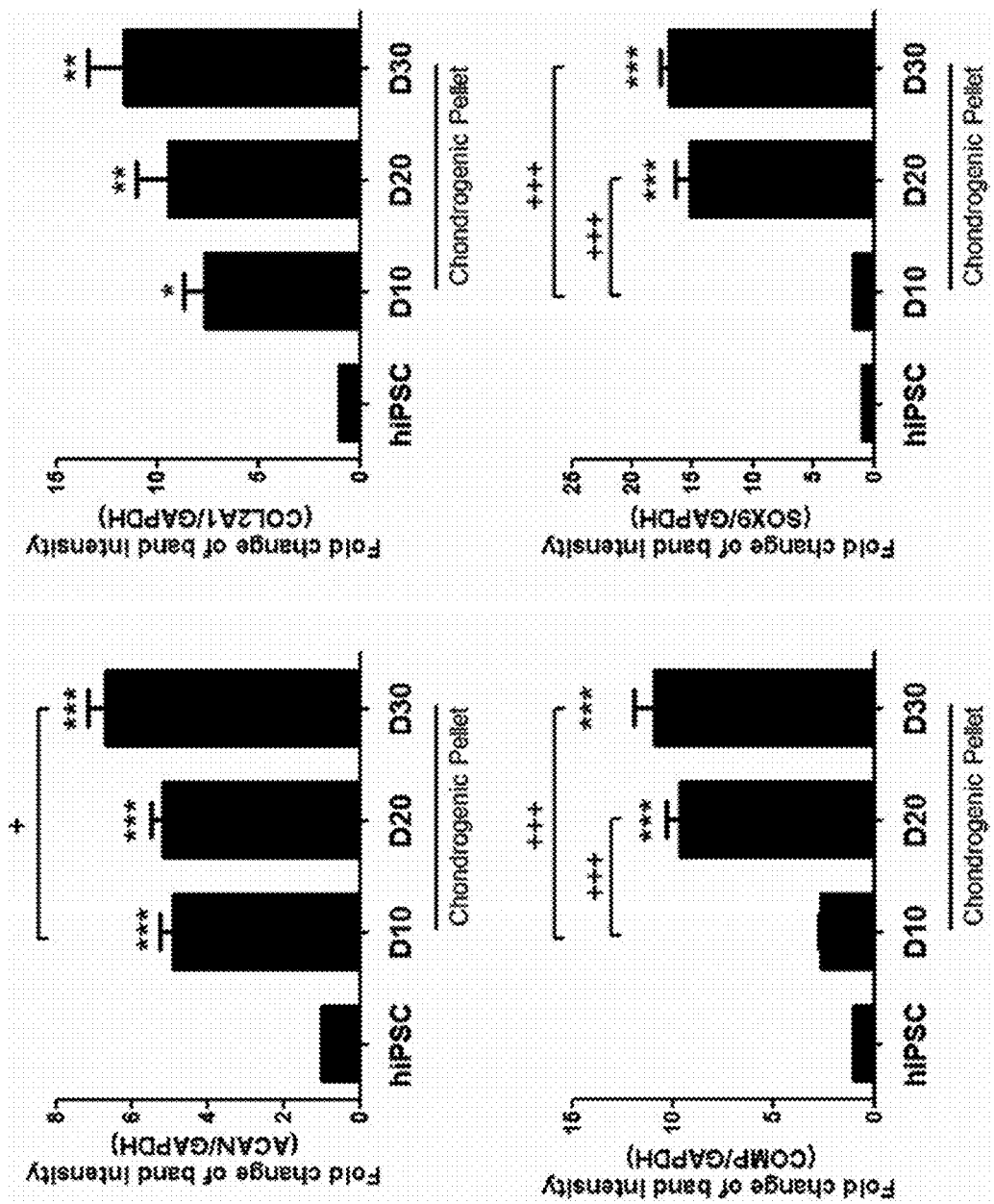
FIG. 3 illustrates results showing, as a genetic characteristic of a chondrogenic pellet generated from CBMC-hiPSCs, expression levels of COL2A1, ACAN, COMP, and SOX9 in the chondrogenic pellet for 10 days, 20 days, and 30 days (*, +p<0.05, , ++p<0.01, *, +++p<0.001).

[Example 3] Identification of Expression of Cartilage Gene in Chondrogenic Pellet Through previous procedures, chondrogenic pellets were successfully generated from CBMC-hiPSCs. In addition, the differentiated cells synthesized ECM components and exhibited cartilage-like characteristics. Expression of major ECM constitutive proteins such as aggrecan (ACAN), type 2 collagen (COL2A1), and cartilage oligomeric matrix protein (COMP) was respectively checked at day 10, day 20, and day 30. As a result, it was identified that expression of ACAN, COL2A1, and COMP is increased (FIG. 3). Sex-determining region Y-box 9 (Sox9) is known as a transcription factor that regulates gene expression of early chondrogenic differentiation markers and ECM proteins. Expression of Sox9 was increased after 20 days. That is, genetic characteristics of the generated chondrogenic pellets were identified. Corresponding to cartilage-like morphology, an increase in gene expression of major ECM component proteins was identified.

[Example 4] Histological Characteristics of Chondrogenic Pellet

Figure 4:
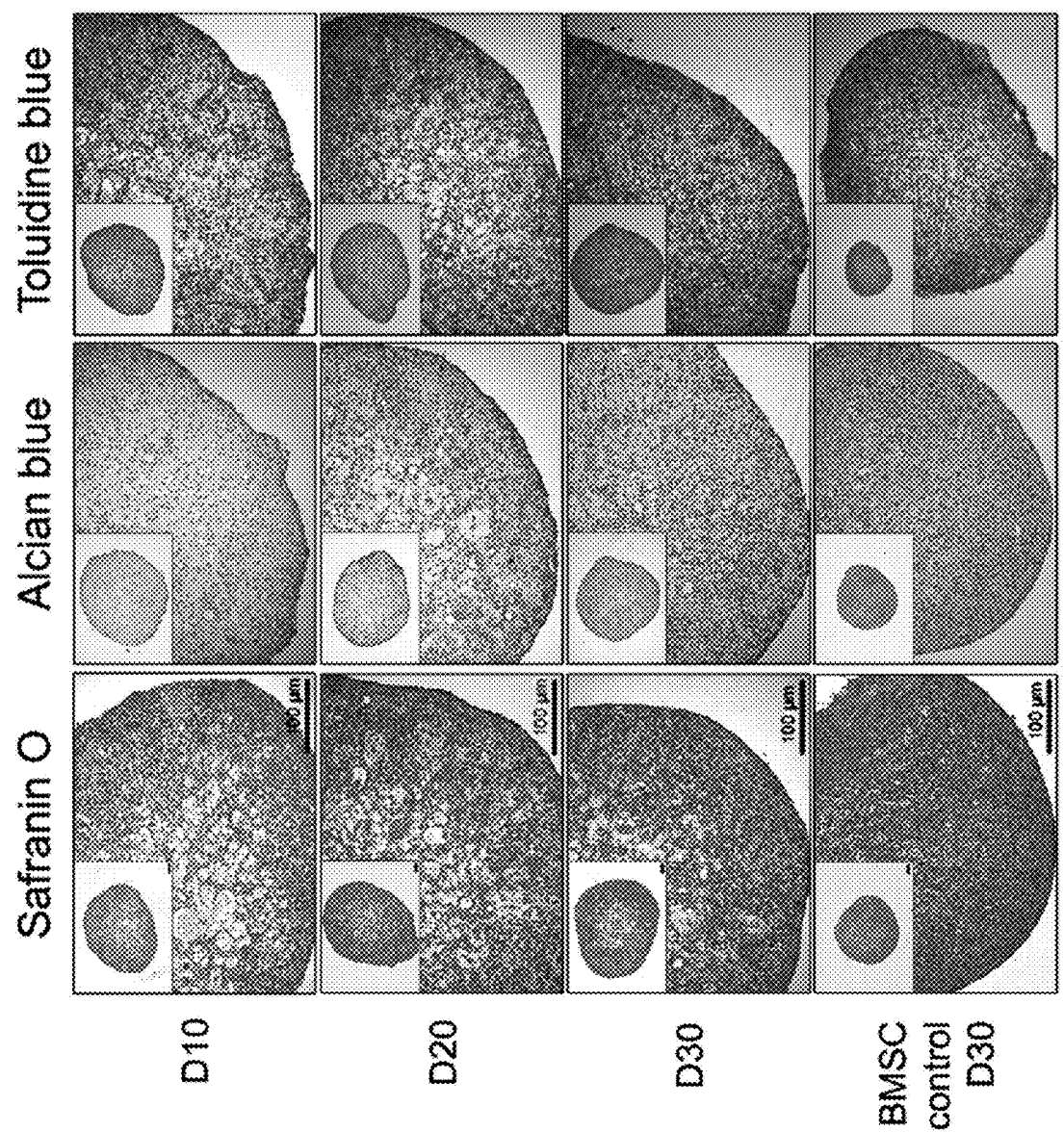
FIG. 4 illustrates results obtained by performing histological analysis of a chondrogenic pellet derived from CBMC-hiPSCs, the results showing images of the chondrogenic pellet stained with safranin O, alcian blue, and toluidine blue at day 10, day 20, and day 30.

As increased expression of chondrogenic markers was identified, protein levels in the chondrogenic pellets generated from CBMC-hiPSCs were evaluated by histological analysis (FIG. 4). Safranin O staining, alcian blue staining, and toluidine blue staining are staining methods used for detection of ECM in cartilage. As a result of the above stainings, accumulation of ECM was identified in the inner part of the pellet even at an early stage of differentiation (day 10). Lacuna is one of the major features appearing in articular cartilage. A reservoir like empty lacuna was seen after 10 days. However, the size thereof was decreased as differentiation progressed. At day 30 of differentiation, the reservoir seemed like lacuna as ECM was accumulated in the reservoir. The staining intensity at day 30 was almost similar.

Figure 5:
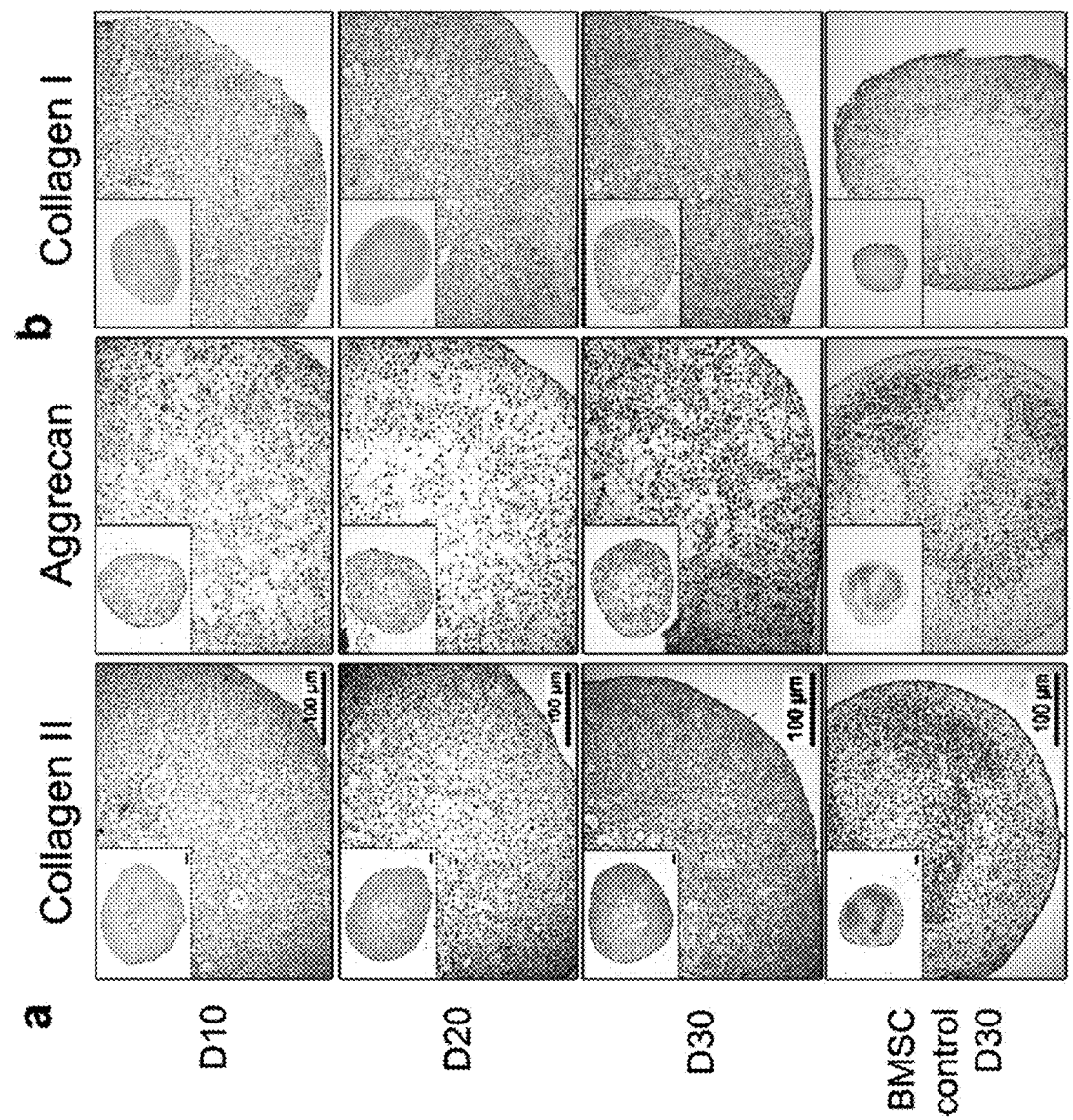
FIGS. 5A-5B illustrate results obtained by performing immunohistological analysis of a chondrogenic pellet derived from BMC-hiPSCs.

The quality of cartilage is determined by the major types of ECM proteins. Therefore, it is important to identify specific proteins. Aggrecan and type 2 collagen proteins are known as main components that constitute ECM. Type 2 collagen is a major collagen type that represents vitreous cartilage. Antibodies against type 2 collagen and aggrecan were stained against the chondrogenic pellet for chondrogenic differentiation (FIG. 5A). The staining intensity of type 2 collagen was higher in the CBMC-hiPSC-derived chondrogenic pellet than the MSC control. Corresponding to the previous staining results, aggrecan and type 2 collagen were mostly detected in the inner part of the pellet at day 30. A major feature of fibrous cartilage is high expression of type 1 collagen. It was identified that the chondrogenic pellet does not have the predominant feature of fibrous cartilage (FIG. 5B). Expression of type 1 collagen was relatively higher than that in MSC control mice. However, expression remained at a certain level and did not remarkably increase during differentiation. The chondrogenic pellet generated from CBMC-hiPSCs is characterized by having a similar quality to the chondrogenic pellet derived from MSCs after 30 days of differentiation. Chondrocytes differentiated from CBMC-hiPSCs were capable of producing ECM component proteins. Type 2 collagen was expressed at a higher level than type 1 collagen in the CBMC-hiPSC-derived chondrogenic pellets. In conclusion, it was identified that CBMC-hiPSCs can produce cartilage-like features similar to those of vitreous cartilage.

Figure 6:
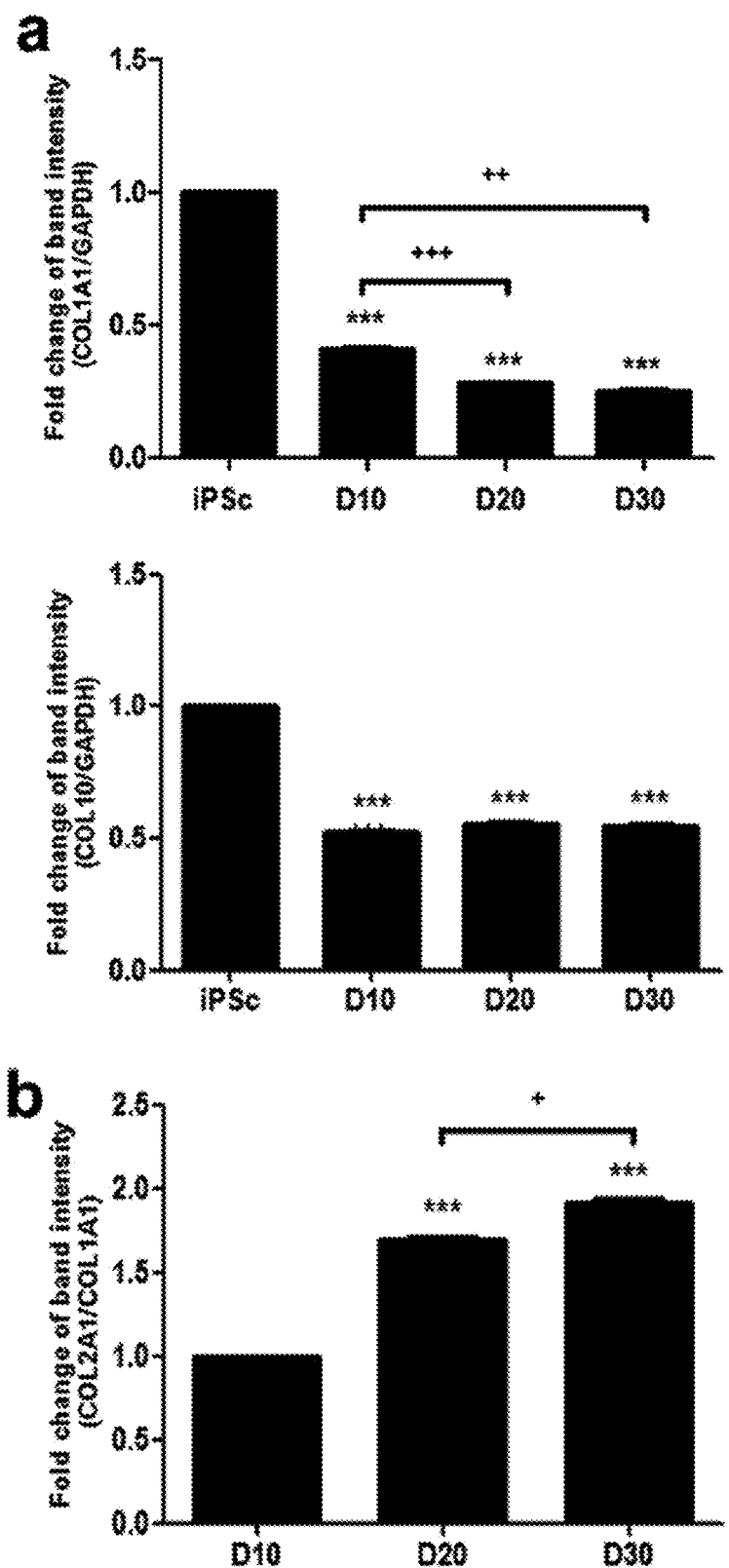
FIGS. 6A-6C illustrate results obtained by performing further analysis for genetic markers of chondrogenic pellets derived from CBMC-hiPSCs and MSCs (*, +p<0.05, , ++p<0.01, *, +++p<0.001)

[Example 5] Analysis for Genetic Markers in Chondrogenic Pellets Derived from CBMC-hiPSCs and MSCs Collagen is the most abundant protein that constitutes ECM. There are many types of collagen, but collagen types 1, 2, and 10 are mainly related to cartilage. In previous experiments, expression of type 1 collagen and type 2 collagen was identified by histological analysis (FIGS. 5A and 5B). Based on the above results, expression of type 1 collagen (COL1A1) gene was analyzed (FIG. 6A). Gene expression of type 10 collagen (COL10), a protein known to be dominant type expressed in hypertrophic cartilage, was also analyzed. Stable expression of type 1 collagen was identified by histochemical staining. However, expression of COL1A1 decreased at each time point. Expression of COL10 did not change during the differentiation process. As mentioned earlier, the proportion of type 2 collagen can alter the resulting characteristics of the chondrogenic pellet. Using the previous gene expression data, the gene expression ratio of COL2A1 to COL1A1 was evaluated (FIG. 6B). The total increase rate indicates that the hyaline cartilage gene is highly expressed relative to the fibrous cartilage gene. The CBMC-hiPSC-derived chondrogenic pellet was compared with the chondrogenic pellet generated in BMSCs at day 30 using real-time PCR (FIG. 6C). There was no statistical significance of ACAN expression between the two samples. Expression of COL2A1 and SOX9 was significantly higher in the chondrogenic pellet differentiated from CBMC-hiPSCs than in the BMSC-derived chondrogenic pellet. However, COMP was highly expressed in the MSC control chondrogenic pellet. Expression of the fibrous marker COL1A1 was also higher in the MSC control chondrogenic pellet. However, expression of the hypertrophy marker COL10 was remarkably lower in the CBMChiPSC-derived chondrogenic pellet. These results highlight possibility of CBMC-hiPSCs as a potential cell source for cartilage regeneration in future applications.

[Example 6] Identification of Differentiation Capacity Increasing Effect of Chondrocytes Differentiated from CBMC-Derived iPSCs In order to identify that differentiation capacity can be improved in the method for differentiation into chondrocytes of the present invention, the present inventors induced differentiation into chondrocytes using peripheral blood cell (PBMC)-derived iPSCs and CBMC-derived iPSCs of the present invention. After differentiation, the respective chondrocytes were obtained, from which expression levels of ACAN and COL2A1 associated with cartilage formation were checked.

Figure 7:
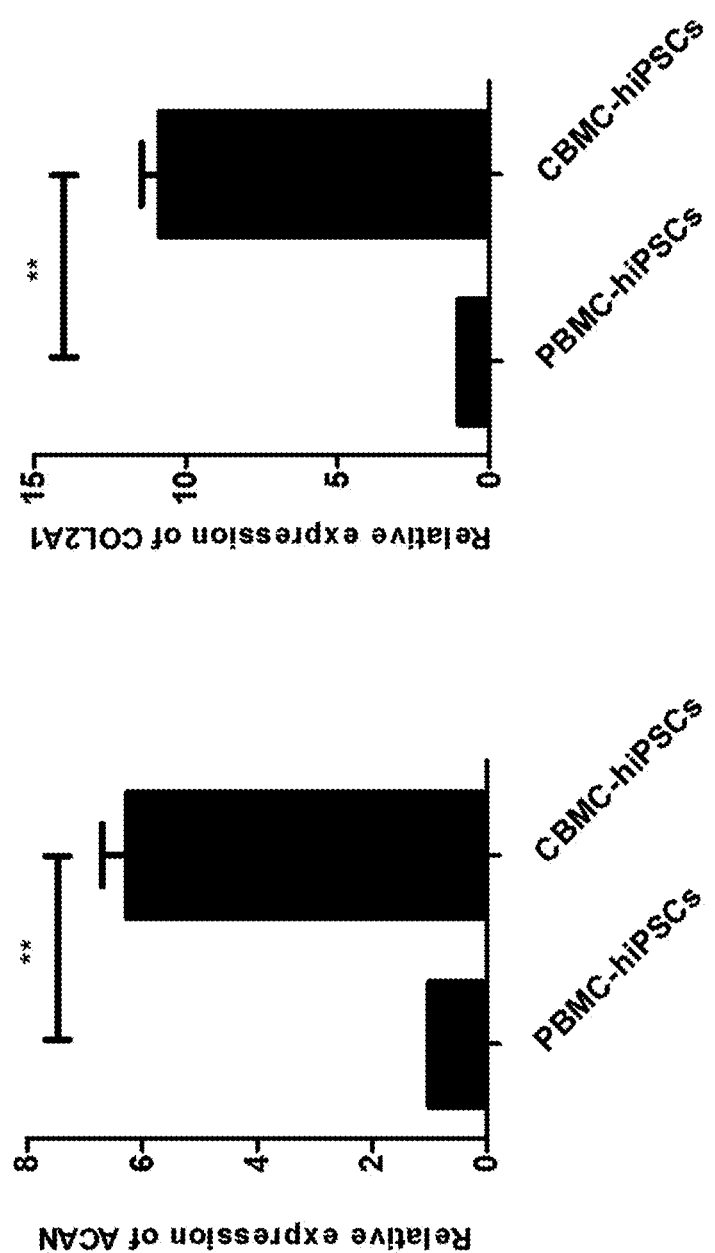
FIG. 7 illustrates results obtained by comparing expression levels of ACAN and CLO2A1, which are cartilage formation-related factors, in chondrocytes differentiated from CBMC-derived iPSCs of the present invention and chondrocytes differentiated from peripheral blood cell (PBMC)-derived iPSCs according to the prior art.

As a result, as illustrated in FIG. 7, it was identified that expression levels of ACAN and AOL2A1 are about 6 to 10 times higher in the CBMC-derived chondrocytes than those of the PMBC-derived chondrocytes. From this, it was identified that cartilage production efficiency is increased in the CBMC-derived chondrocytes of the present invention.

[Example 7] Identification of Whether Prepared iPSCs are Homozygotes

In order to identify whether the prepared CMC-hiPSCs are homozygotes, allele types of Human Leukocyte Antigen (HLA) were analyzed for three CMC-derived iPSC cell lines. As a result, as shown in [Table 4] to [Table 6], it was identified that the CMC-hiPSCs prepared by the method of the present invention are homozygotes.

Accordingly, the chondrocytes differentiated using the CMC-iPSCs of the present invention can be used in the form of chondro beads to produce cartilage tissue, and an increased transplantation success rate can be exhibited.

TABLE 4

Results of HLA test (SBT)

| | HLA-A | HLA-B | HLA-C | DRB1 | DQB1 | DPB1 |
|---|---|---|---|---|---|---|
| CMC-hiPSC-008 | *33:03(A33) *33:03(A33) | *44:03(B44) *44:03(B44) | — — | *13:02 *13:02 | — — | — — |

TABLE 5

Results of HLA test (SBT)

| | HLA-A | HLA-B | HLA-C | DRB1 | DQB1 | DPB1 |
|---|---|---|---|---|---|---|
| CMC-hiPSC-009 | *24:02(A24) *24:02(A24) | *07:02(B7) *07:02(B7) | — — | *01:01 *01:01 | — — | — — |

TABLE 6

Results of HLA test (SBT)

| | HLA-A | HLA-B | HLA-C | DRB1 | DQB1 | DPB1 |
|---|---|---|---|---|---|---|
| CMC-hiPSC-008 | *11:01(A11) *11:01(A11) | *15:01(B62) *15:01(B62) | — — | *04:06 *04:06 | — — | — — |

For production of iPSCs, the homozygous type that can account for the highest proportion of the Korean population was selected. However, HLA types of Koreans are treated as confidential due to the Personal Information Protection Law. Accordingly, in the present study, HLA type information of CBMCs which had been legally donated and were stored in the Catholic Hematopoietic Stem Cell Bank was analyzed. As shown in [Table 7] below, information on the top 20 HLA types was obtained. HLA-A*33, HLA-B*44, and HLA-DRB1*13 accounted for approximately 23.97% in the entire CBMC bank, and thus were the most frequent homozygous HLA types. The second most frequent types were HLA-A*33, HLA-B*58, and HLA-DRB1*13 which were recorded as accounting for 11.16% of the estimated population. In the top 5 types, the coverage of HLA types was less than 5%. Among the three HLA types, HLA-A tended to be relatively more concentrated than the other two types. Of the 20 selected HLA types, 25% had HLA-A type of *33 and 40% had HLA-A type of *02.

Figure 8:
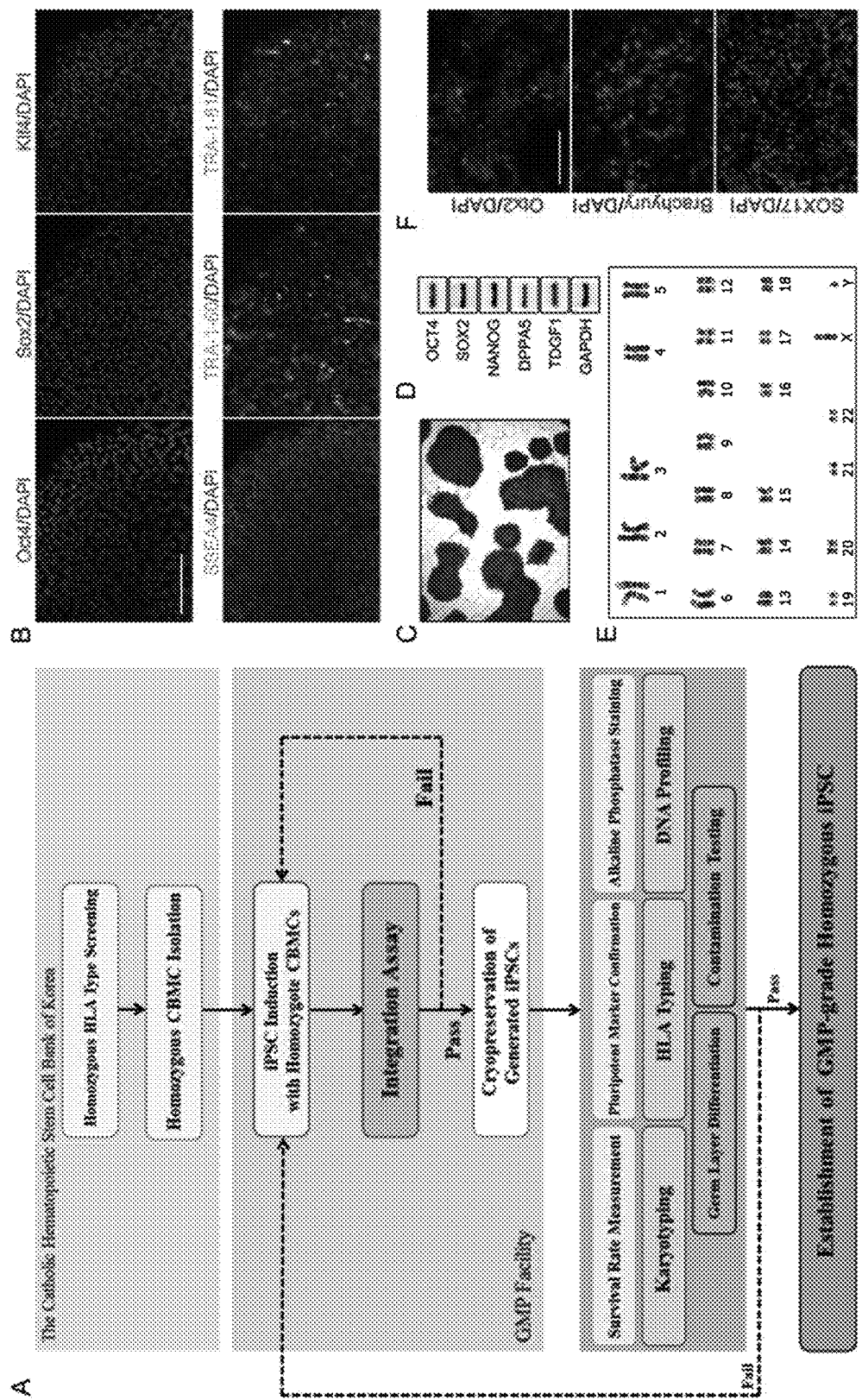
FIGS. 8A-8F illustrate results which identify good manufacturing practice (GMP)-grade homozygous human leukocyte antigen (HLA)-induced pluripotent stem cells.

Based on the information of the classified HLA types, 9 homozygous cells were selected for recombination in the Catholic Hematopoietic Stem Cell Bank. In addition, 4 PBMC samples with homozygous HLA types were obtained as a gift. As shown in [Table 8] below, 3 of the total 13 cell samples had HLA types of HLA-A*33, HLA-B*44, and HLA-DRB1*13. The obtained cells were transferred to the GMP facility at the Catholic Institute of Cell Therapy for reprogramming After treatment with a Yamanaka factor, samples with no defect were isolated and characterized by various assays. Survival was measured based on cell attachment. Pluripotency was identified through PCR and immunofluorescence. Undifferentiated state of the cells was identified by alkaline phosphatase staining. Karyotyping and short tandem repeat assay were performed to identify the normal genetic background. Finally, multiple transfers thereof were identified through differentiation into respective germ layers, and infection testing was performed. After undergoing these processes, only cells that passed all quality control tests were stored in the GMP facility (FIG. 8A).

After several subcloning procedures, all cell lines showed a proper form of iPSCs. Homozygous HLA-iPSCs showed positive expression of pluripotency markers (FIGS. 8B and 8D). All cells remained undifferentiated during passaging (FIG. 8C). Normal karyotype was identified in the cell line (FIG. 8E). In addition, the produced cells were capable of differentiating into all three germ layers in vitro (FIGS. 8F and 8G). The data illustrated in FIGS. 8B-8F represents data for the CMC-hiPSC-001 cell line.

Production of homozygous HLA-iPSCs opened up new opportunities for development of personalized regenerative medicine. By reducing the time, money and manpower required, the homozygous HLA-iPSCs can be used to treat a large number of patients with minimal cell sources. Depending on the HLA phenotype allele frequency, candidate HLA homozygous cell types can be selected and held as an iPSC resource bank. However, homozygous cells are not frequently found, and thus it is important to estimate the minimum or appropriate number of iPSCs that accounts for the largest percentage of the population.

As a result, the present inventors determined the frequencies of homozygous HLA types in the Korean population with an alternative method. The present inventors firstly accessed the HLA-typed CBMC library of the Catholic Institute of Cell Therapy. Through the CBMC bank, it was identified that 23.9% of the HLA-homozygous CBMCs stored at the bank show phenotypes of HLA-A*33, HLA-B*44, and HLA-DRB1*13. Homozygous single cells were screened through the produced data and reprogrammed so that the cells are obtained as iPSCs. The three homozygous HLA-iPSCs, HLA-A*33, HLA-B*44, and HLA-DRB1*13 were produced. 13 produced HLA-iPSC lines had high pluripotency and normal karyotype and passed various contamination tests. This is the first achievement in which the Korean homozygous HLA-iPSC bank has been established in Koreans under the sponsorship of the Korean government. Homozygous HLA-iPSCs will open up new opportunities for successful regenerative medicine and clinical stem cell therapy.

TABLE 7

|   | HLA-A | HLA-B | HLA-DR(B1) | % of Frequency |
|---|-------|-------|------------|----------------|
| 1 | *33 | *44 | *13 | 23.97 |
| 2 | *33 | *58 | *13 | 11.16 |
| 3 | *24 | *07 | *01 | 7.85 |
| 4 | *30 | *13 | *07 | 7.44 |
| 5 | *33 | *44 | *07 | 7.02 |
| 6 | *24 | *52 | *15 | 4.55 |
| 7 | *11 | *15 (62) | *04 | 4.13 |
| 8 | *24 | *54 | *04 | 2.48 |
| 9 | *02 | *46 | *08 | 2.07 |
| 10 | *01 | *37 | *10 | 1.65 |
| 11 | *02 | *27 | *01 | 1.65 |
| 12 | *02 | *15 (62) | *04 | 1.24 |
| 13 | *24 | *51 | *09 | 1.24 |
| 14 | *33 | *58 | *03 | 1.24 |
| 15 | *33 | *58 | *15 | 1.24 |
| 16 | *02 | *13 | *12 | 0.83 |
| 17 | *02 | *46 | *09 | 0.83 |
| 18 | *02 | *48 | *04 | 0.83 |
| 19 | *02 | *48 | *14 | 0.83 |
| 20 | *02 | *51 | *15 | 0.83 |

TABLE 8

| Donor No. | Cell Type | HLA Type A | B | DR(B1) |
|-----------|-----------|-----|-----|--------|
| CMC-hiPSC-001 | PBMC | *33:03 | *44:03 | *13:02 |
| CMC-hiPSC-002 | PBMC | *33:03 | *44:03 | *07:01 |
| CMC-hiPSC-003 | PBMC | *33:03 | *44:03 | *13:02 |
| CMC-hiPSC-004 | PBMC | *33:03 | *44:03 | *07:01 |
| CMC-hiPSC-005 | CBMC | *33:03 | *58:01 | *13:02 |
| CMC-hiPSC-006 | CBMC | *33:03 | *44:03 | *07:01 |
| CMC-hiPSC-007 | CBMC | *02:01 | *48:01 | *14:54 |
| CMC-hiPSC-008 | CBMC | *33:03 | *44:03 | *13:02 |
| CMC-hiPSC-009 | CBMC | *24:02 | *07:02 | *01:01 |
| CMC-hiPSC-010 | CBMC | *02:01 | *51:01 | *04:03 |
| CMC-hiPSC-011 | CBMC | *11:01 | *15:01 | *04:06 |
| CMC-hiPSC-012 | CBMC | *33:03 | *58:01 | *13:02 |
| CMC-hiPSC-013 | CBMC | *33:03 | *58:01 | *13:02 |

[Example 8] Construction of Minicircle Vector Encoding Human Growth Factor

<8-1> Construction of Minicircle Vector Expressing BMP2 or TGFβ3

Figure 9A:
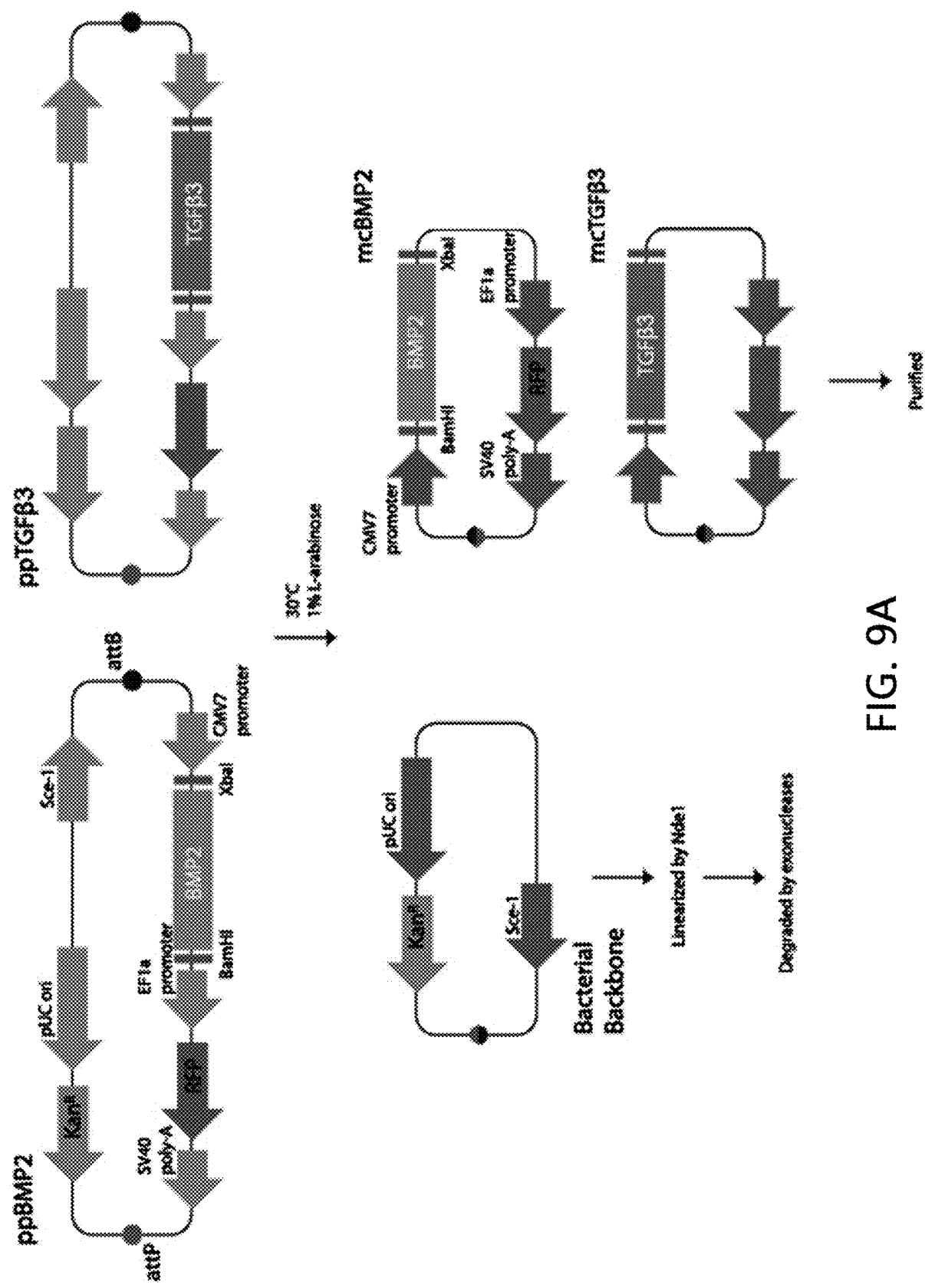
FIGS. 9A-9B illustrate construction and identification of minicircle vectors encoding human growth factors of the present invention.

In order to induce expression of BMP2 and TGFβ3 in the present invention, minicircle vectors were constructed in the same procedure as illustrated in FIG. 9A.

Specifically, for human BMP2 and TGFβ3 genes, cDNA sequences were synthesized as the base sequences of SEQ ID NO: 1 and SEQ ID NO: 2, respectively, by optimizing codons and used. The synthesized cDNA sequence was inserted into a parental plasmid (CMV-MCS-EF1-RFP-SV40-PolyA; manufacturer: System Biosciences, Mountain View, Calif., USA) as a mock vector. At the time of insertion, the BMP2 and/or TGFβ3 sequences were inserted into the sequence between BamHI and XbaI in a multiple cloning site downstream of the CMV promoter, to construct a parental vector containing the growth factor gene. Each parental vector (ppBMP2, pp TGFβ3) containing BMP2 or TGFβ3 was respectively transformed into ZYCY10P3S2T E. coli cells. The transformed cells were isolated into single unit colonies, which were inoculated in 2 ml of LB medium containing 500 μl/ml of kanamycin and initially cultured at 30° C. for 2 hours. Then, 200 ml of terrific broth (TB) was added to a 1 L culture flask, 100 μl of the initially cultured medium was inoculated thereinto, and the culture flask was cultured for 15 hours with shaking culture at 30° C. with 200 rpm. After the culture, 200 ml of LB medium containing 200 μl of 4% 1N NaOH and 20% L-arabinose was added to the culture flask so as to convert the parental vector plasmid into a minicircle vector. The flask to which the medium had been added was further cultured at 30° C. with 200 rpm for 5 hours. After completion of the culture, the cells were obtained and plasmid DNA was extracted using the NucleoBond Xtra plasmid purification kit (Macherey-Nagel, Duren, Germany). The extracted DNA was doubly cleaved with XbaI and BamHI to check the size of the constructed minicircle and the inserted BMP2 or TGFβ3 gene. The respective vectors into which BMP2 and TGFβ3 had been inserted were named mcBMP2 and mcTGFβ3, respectively. In order to prepare a negative control, a minicircle vector (mcMock) was constructed in the same manner using a parental plasmid (ppMock) into which BMP2 and TGFβ3 had not been inserted.

Figure 9B:
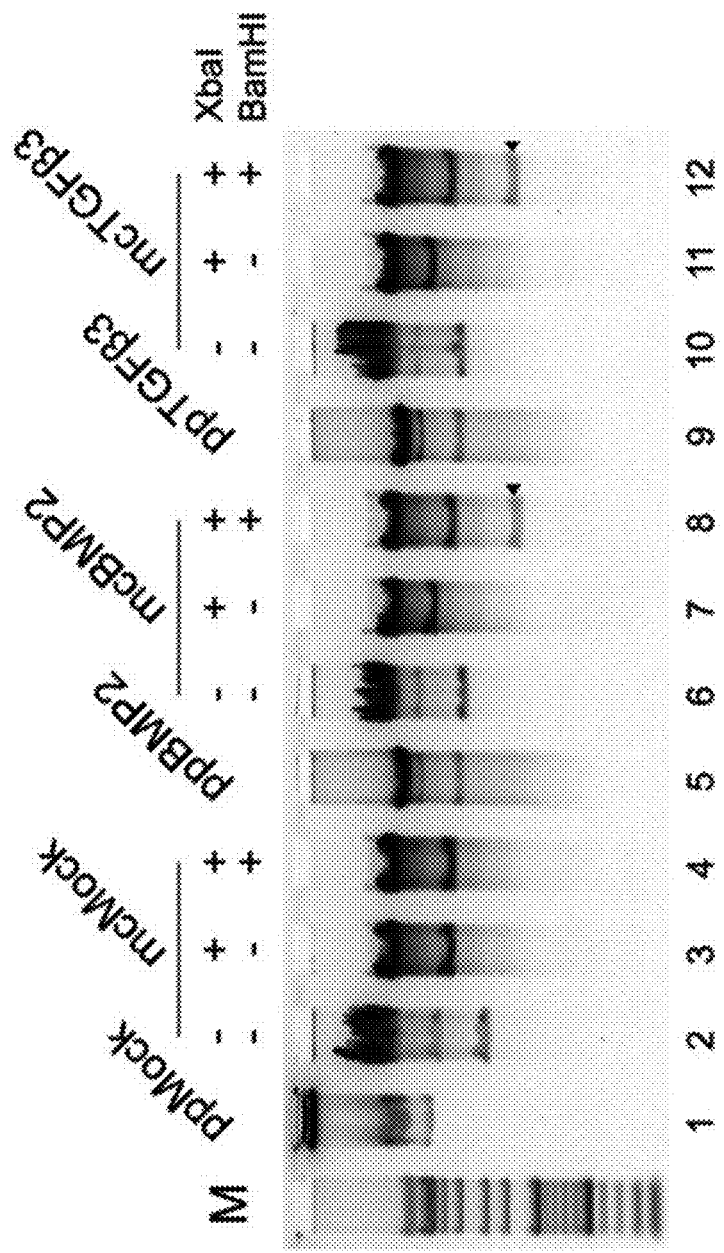

As a result, as illustrated in FIG. 9B, it was identified that the size of mcBMP2 is about 7.3 kb and appears as two bands of about 1.1 kb of BMP2 gene and about 5 kb of minicircle in a case of being doubly cleaved with restriction enzymes. In addition, it was identified that the size of mc TGFβ3 is about 7.5 kb and appears as two bands of about 1.3 kb of TGFβ3 gene and about 5 kb of minicircle in a case of being doubly cleaved with restriction enzymes.

<8-2> Identification of Transduction Efficiency of mcBMP2 and mcTGFβ3

In order to identify whether mcBMP2 and mcTGFβ3 are capable of significantly exhibiting expression activity in a case of being transduced into cells, expression levels of RFP which is also present in both mcBMP2 and mcTGFβ3 were measured.

Specifically, mcBMP2 or mcTGFβ3 constructed in Example <8-1> was respectively mixed with lipofectamine in Opti-MEM medium (Thermo Fisher Scientific) for 20 minutes. Then, the mixed DNA-lipofectamine mixture was added to HEK293T cell culture medium and incubated for 6 hours in a 5% $CO_2$ incubator at 37° C. After the incubation, the cells were checked for cell morphology with a phase contrast microscope, and then expression levels of RFP in HEK293T cells were observed using a fluorescence microscope. In addition, a level of protein expressed in HEK293T cells transformed with mcBMP2 or mcTGFβ3 was identified by checking a level of protein expression with the Bradford assay for the medium in which the cells had been cultured. For quantitative analysis, absorbance values were relatively compared on the basis that the absorbance value of the recombinant BMP2 protein (rhBMP2) or recombinant TGFβ3 protein solution is 1.0.

Figure 10:
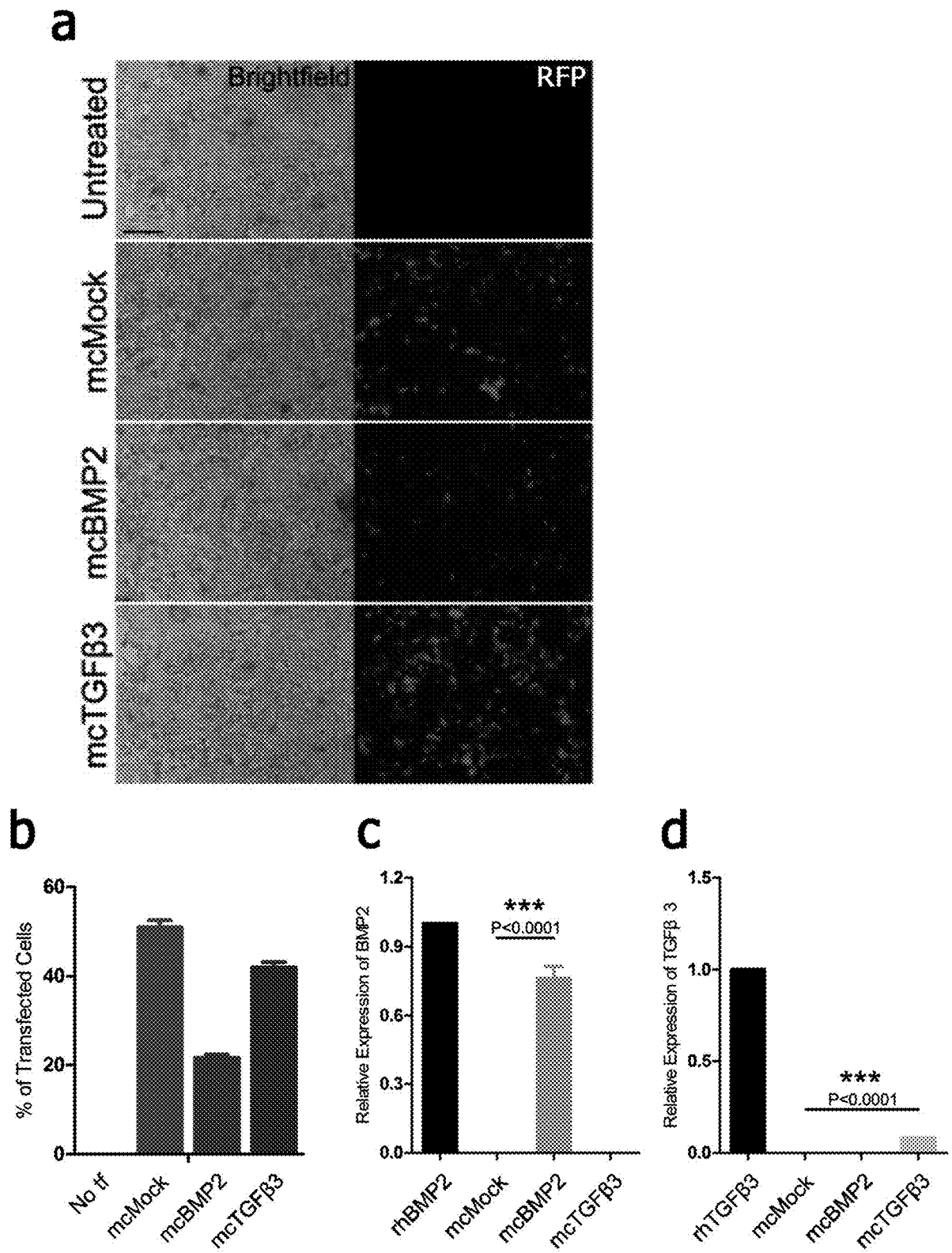
FIGS. 10A-10D illustrate identification of expression efficiency of mcBAMP2 or mcTGFβ3 transduced into HEK293T cells.

As a result, as illustrated in FIGS. 10A-10D, it was identified that the highest expression level of RFP is observed in mcMock-transduced cells as compared with HEK293T cells transduced with mcBMP2 and mcTGFβ3, indicating that mcMock exhibits the highest transduction efficiency (FIGS. 10A and 10B). In addition, it was identified that in a case where a level of protein expressed and secreted in the cell culture medium is checked, the supernatant of the HEK293T cells transformed with mcBMP2 exhibits a significantly high level of absorbance, indicating an expression level of about 0.1 mg/ml (FIG. 10C). As compared with this, it was identified that expression of mcTGFβ3 is observed at a relatively low level. However, as compared with the culture supernatant of mcMock, it was identified that the cells are capable of exhibiting a significant protein expression level as transduced with mcTGFβ3 (FIG. 10D).

[Example 9] Induction of Differentiation into Human iPSC-Derived Chondrocytes Using mcBMP2 and mcTGFβ3

Figure 11:
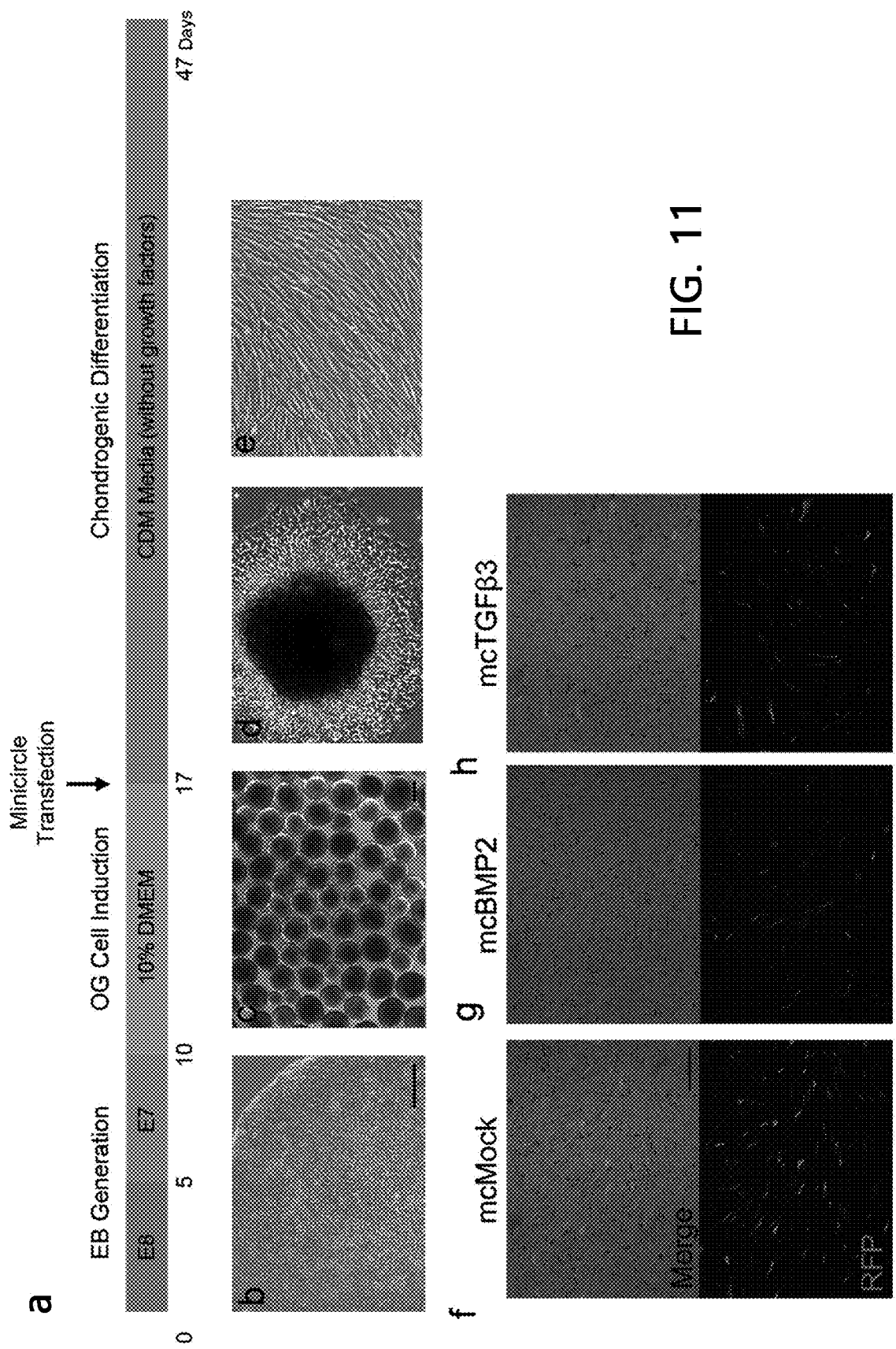
FIGS. 11A-11H illustrate a chondrogenic pellet produced by differentiation induction from iPSCs in the present invention.

A method of differentiating human-derived iPSCs (hiPSCs) into chondrocytes was performed according to the procedure of the schematic diagram illustrated in FIG. 11A. All experiments were repeated three times in total for the same experimental group.

i) Step of Preparing iPSCs

The method for obtaining iPSCs from cord blood mononuclear cells (PBMCs) was carried out with a reprogramming method according to the conventional dedifferentiation induction method [NPL 1]. The obtained iPSCs were cultured in a container coated with vitronectin (Thermo Fisher Scientific, Waltham, Mass., USA), and the culture was performed using E8 medium (STEMCELL Technologies) as a culture medium with daily medium replacement. The morphology of the prepared iPSCs is as illustrated in FIG. 11B.

ii) Step of Generating Embryoid Bodies (EBs) from iPSCs:

The prepared iPSCs were detached from the bottom of the container. The detached iPSCs were counted to $2 \times 10^6$ cells and inoculated onto a new plate. A 1:1 mixture of TeSR-E8 medium and Aggrewell medium (STEMCELL Technologies) was used as a culture medium. The IPSC cells inoculated into the mixed medium were cultured in a 5% $CO_2$ incubator at 37° C. for 24 hours. Then, the medium was removed and replaced with fresh E8 medium. Culture was performed for 3 days. Then, the medium was replaced with E7 medium and culture was further performed for 3 days to obtain embryoid bodies (EBs) (FIG. 11C).

iii) Step of Inducing EBs to Outgrowth Cells (OG Cells):

Then, the EBs were transferred to a gelatin-coated container. For this purpose, the culture container of which the bottom had been coated with 0.1% gelatin for 30 minutes and completely dried was used. The resulting EBs were obtained and suspended in an OG induction medium. As the OG induction medium, DMEM (Thermo Fisher Scientific) medium containing 20% fetal bovine serum (FBS, Thermo Fisher Scientific) and 10% penicillin/streptomycin (Thermo Fisher Scientific) was used. The EBs were inoculated into a gelatin-coated container at a density of 50 to 70 EBs/cm$^2$, and cultured in a 5% $CO_2$ incubator at 37° C. for 3 days so that protruding cells like branches (outgrowth cells (OG cells)) were cultured and induced. Morphology of the induced OG cells is as illustrated in FIG. 11D.

iv) Step of Transducing OG Cells with Minicircle Vectors:

Then, the OG cells were detached and the remaining EB clumps were removed with a 40 μm cell strainer (BD Technologies, Franklin Lakes, N.J., USA) so that OG cells in single unit cells were obtained (FIG. 11E). The OG cells represent fibrous morphology similar to mesenchymal stem cells. The obtained OG cells were again inoculated into a new gelatin-coated container at a density of 1 to $5 \times 10^4$ cells/cm$^2$ and transduction was performed with the minicircle vectors constructed in Example <8-1>. On the day prior to transduction, the culture medium was replaced with DMEM medium containing no serum and antibiotics, and culture was performed overnight. Then, transduction was performed with mcMock, mcBMP2, or mcTGFβ3 using Lipofectamine 2000 reagent (Thermo Fisher Scientific). For the cells transduced with the minicircle vectors, identification of whether transduction had occurred was made by checking the expression level of intracellular RFP using a fluorescence microscope (FIGS. 11F to 11H). It was identified that the OG cells transduced with mcMock exhibit a high level of RFP expression, and that the OG cells transduced with mcBMP2 or mcTGFβ3 exhibit a low level of RFP expression as compared with mcMock, similar to the expression pattern of RFP in HEK293T cells.

v) Step of Inducing Differentiation of OG Cells Transduced with Minicircle Vectors into Chondrogenic Pellet:

The OG cells for which transduction had occurred due to overnight culture were prepared in a 15 ml conical tube to give $3 \times 10^5$ cells per pellet, and cultured in a chondrogenic differentiation medium. The chondrogenic differentiation medium (CDM) used a composition of DMEM medium which contains 20% knockout serum replacement, 1× nonessential amino acid, 1 mM L-glutamine, 1% sodium pyruvate, 1% ITS+Premix, $10^{-7}$ M Dexamethasone, 50 mM ascorbic acid, and 40 μg/ml of L-proline. No recombinant growth factors such as BMP2 and TGFβ3 were added to the CDM. The OG cells were suspended in the CDM medium, precipitated by centrifugation at 750×g for 5 minutes, and then cultured for 30 days to differentiate into a chondrogenic pellet. The medium was replaced at intervals of 3 days. After completion of the final culture, the differentiated chondrogenic pellet was obtained. The obtained chondrogenic pellet was kept frozen at −80° C. before use.

[Example 10] Characterization of Cells Produced by Differentiation Induction Using Minicircle Vectors <10-1> Characterization of OG Cells Induced from iPSCs In order to identify characteristics of the OG cells cultured in the step iii) of inducing EBs to OG cells, expression levels of mesenchymal stem cell (MSC) markers were checked.

The OG cells induced in the step iii) of <Example 8> were obtained and suspended in Trizol (Thermo Fisher Scientific) so that the cells were disrupted and mRNA was extracted therefrom. Using the extracted mRNA as a template, cDNA was synthesized with the RevertAid™ First Strand cDNA synthesis kit (Thermo Fisher Scientific). Using the synthesized cDNA again as a template, PCR was performed on the MSC marker genes CD44, CD73, CD90, CD105, and CD45, and expression levels of the respective genes were checked. Quantitative analysis was performed by repeatedly checking the expression level three times for the same gene, and then the value of each gene expression level was corrected based on the expression level of GAPDH in the same cells. In addition to the OG cells, an expression level of the same gene was checked for iPSCs.

Figure 12:
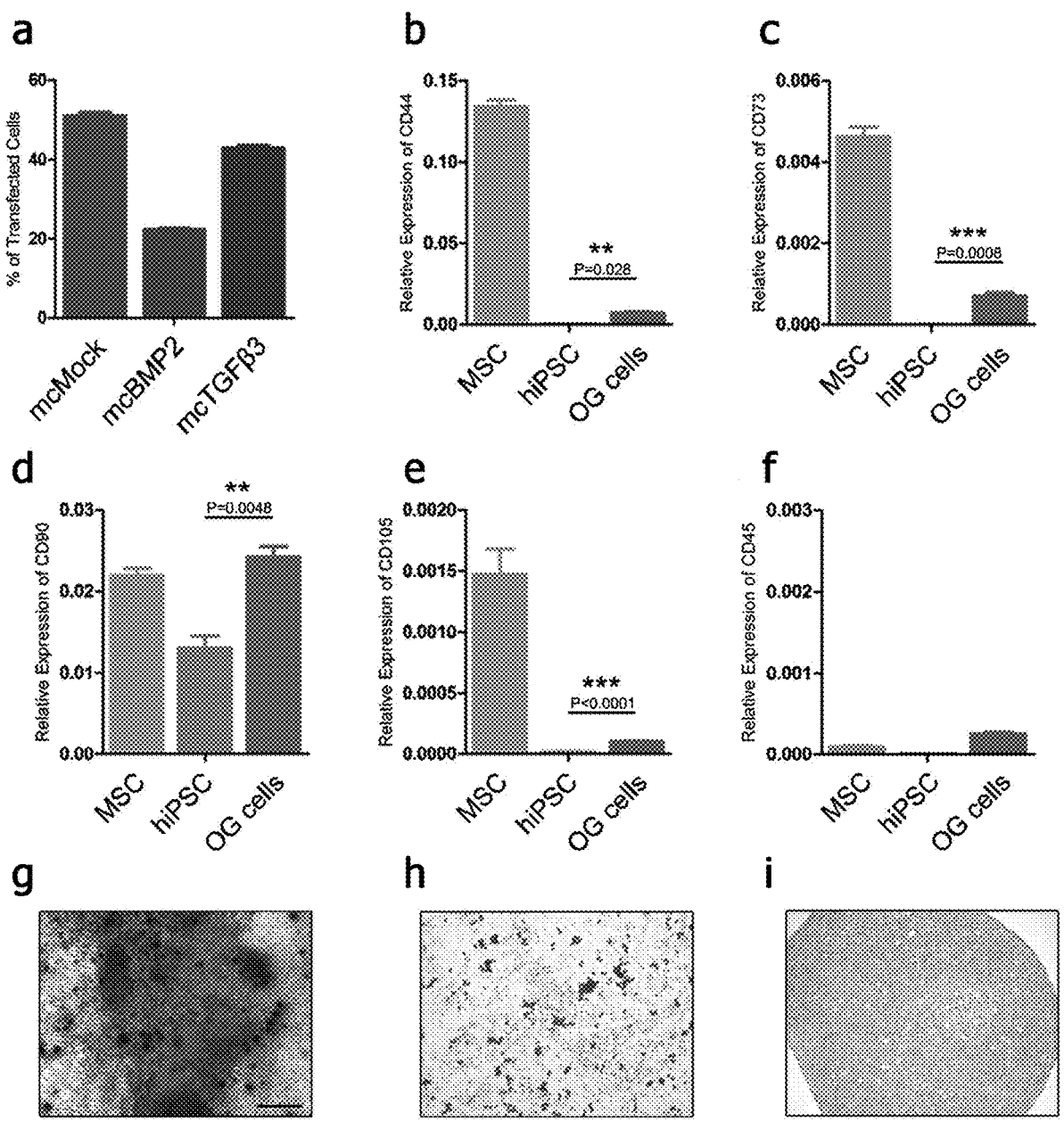
FIGS. 12A-12I illustrate identification of mesenchymal stem cell-related factors in OG cells into which the minicircle vectors of the present invention have been transduced.

First, in a case of checking efficiency when the minicircle vectors are transduced into the OG cells, it was identified that efficiency of the minicircle vectors transduced into the OG cells shows a similar tendency to that of HEK293T cells (FIG. 12A). In addition, expression of MSC marker genes was checked. As a result, it was identified that the OG cells exhibit significant expression levels of CD44, CD73, and CD105, which are somewhat low expression levels as compared with MSCs and are significantly high expression levels as compared with hiPSCs (FIG. 12B, FIG. 12C and FIG. 12E). On the contrary, it was identified that CD90 was expressed at a somewhat higher level in the OG cells than MSCs (FIG. 12D). In addition, it was identified that CD45, known to be a marker which is negatively expressed in mesenchymal stem cells, is expressed at a low level in both MSCs and the OG cells (FIG. 12F).

In addition, it was intended to identify differentiation potential of MSCs. MSCs are known to be able to differentiate into the three lineages, adipocytes, chondrocytes, and osteoblasts. The present inventors performed alizarin red staining, oil red O staining, and alcian blue staining to identify lineage differentiation capacity of the OG cells induced from iPSCs.

As a result, as illustrated in FIGS. 12G to 12I, it was identified that the OG cells exhibit pluripotency which makes it possible to differentiate into chondrocyte lineage (FIG. 12G), to differentiate into adipocyte lineage (FIG. 12H), and to differentiate into chondrogenic pellet (FIG. 12I).

<10-2> Identification of Expression Efficiency of Intracellular Growth Factor Protein Produced by Differentiation Induction Using mcBMP2 and mcTGFβ3

In order to identify expression efficiency of the minicircle vectors in the chondrogenic pellet produced by differentiation induction in the step v) of <Example 8>, expression of RFP and GFP in the cells which are in a differentiation induction process was checked. OG cells (mcBMP2-OG) into which mcBMP2 had been transduced, OG cells (mcTGFβ3-OG) into which mcTGFβ3 had been transduced, and also a mixture (mcBOTH-OG) of mcBMP2-OG and mcTGFβ3-OG at a 1:1 ratio were inoculated into a medium, and co-cultured to induce differentiation into chondrocytes. Chondrogenic pellets were precipitated by centrifugation to form condensates at day 5, day 10, day 20, and day 30 after initiation of differentiation induction of the OG cells transduced with the minicircle vectors in chondrogenic differentiation medium. Then, for the condensates, cell morphology, expression of intracellular RFP, and expression level of GFP were checked.

Figure 13:
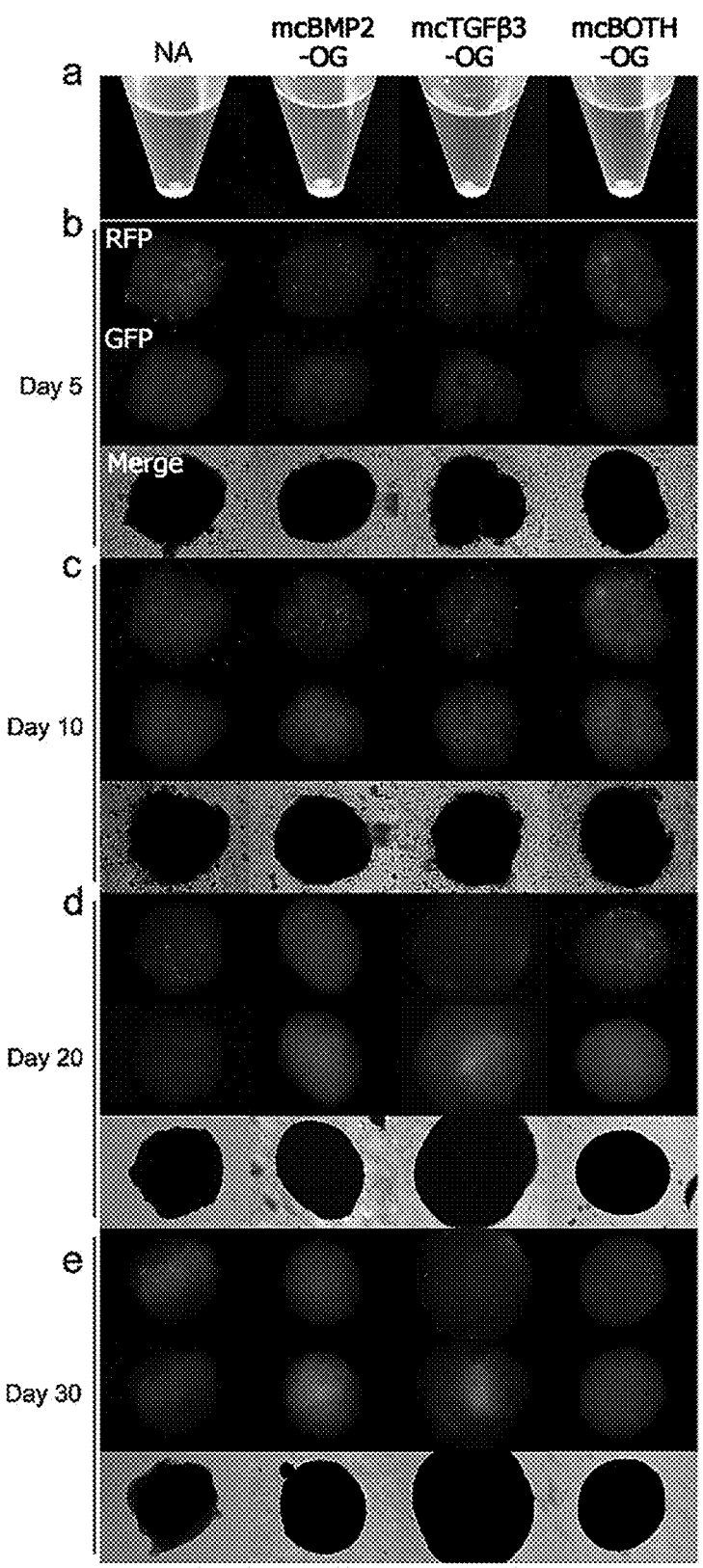
FIGS. 13A-13E illustrate results obtained by identifying characteristics of a chondrogenic pellet produced by differentiation induction with transduction of minicircle vectors.

As a result, as illustrated in FIGS. 13A-13E, it was first identified that the amount of the condensed cells in mcTGFβ3-OG is somewhat lower than that in the other experimental groups (FIG. 13A). From 20 days after initiation of differentiation induction, the size of the cell condensate in mcTGFβ3-OG was increased as compared with mcBMP2-OG and mcBOTH-OG, and mcTGFβ3-OG exhibited the cell proliferation rate at a significantly higher level than that in the other experimental groups (FIG. 13D).

In a case where the expression level of RFP is checked, it was identified that the expression level of RFP in the chondrogenic pellets increases from 5 days after initiation of differentiation induction in all experimental groups (FIG. 13B). Thereafter, it was identified that morphology of the agglutinated cells continues to remain even at day 10 (FIG. 13C). The expression of RFP in all experimental groups of mcBMP2-OG, mcTGFβ3-OG, and mcBOTH-OG tended to increase continuously up to 20 days after initiation of differentiation induction (FIG. 13D). The expression tended to decrease from 30 days after initiation of differentiation induction (FIG. 13E). In a case of the OG cell control (NA) transduced with mcMock, it was identified that the expression of RFP is continuously increased after initiation of differentiation and is kept even after 30 days.

<10-3> Identification of Differentiation Efficiency of Chondrogenic Pellet Produced by Differentiation Induction Using mcBMP2 and mcTGFβ3

Subsequently, in order to analyze characteristics of the differentiated chondrogenic pellet, expression levels of the marker genes in chondrocyte, which are SOX9, ACAN, COL2A1, COL1A1, and COL10A1, were checked. In addition, osteoclastogenic capacity of the chondrogenic pellet was identified by checking the expression level of RUNX2, an osteogenic marker. In order to compare differentiation efficiency using the minicircle vectors of the present invention with the conventional technique, the expression of the same marker genes was checked for the positive control (Both rhGF) which had been induced to differentiate into chondrocytes in a medium containing both the BMP2 and TGFβ3 growth factors without transduction of the minicircle vectors.

Figure 14:
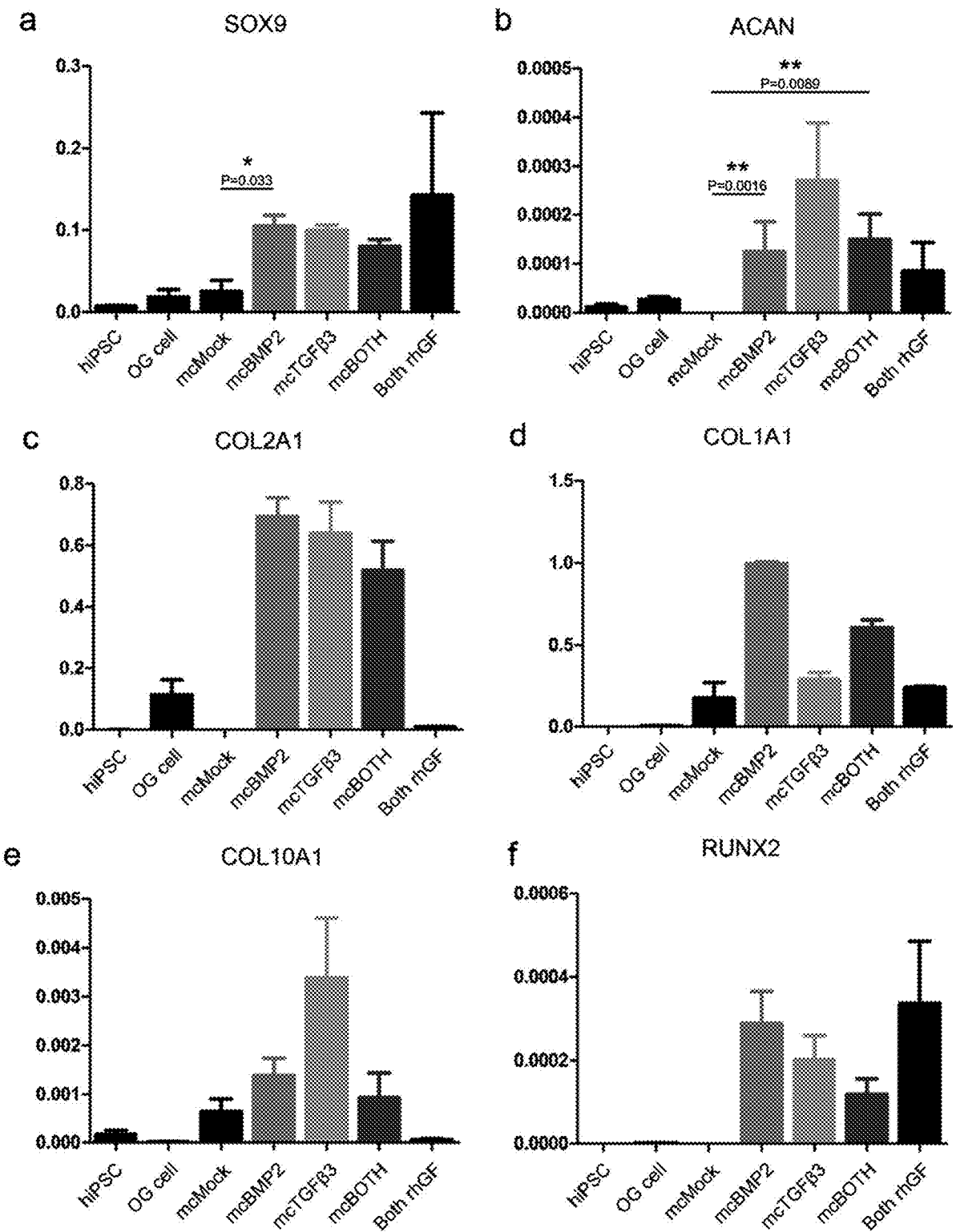
FIGS. 14A-14F illustrates results obtained by identifying expression levels of chondrocyte marker genes in a chondrogenic pellet produced by differentiation with transduction of the minicircle vectors of the present invention.

As a result, as illustrated in FIGS. 14A-14D, it was identified that the chondrocyte marker genes are expressed at high levels in all experimental groups of mcBMP2-OG, mcTGFβ3-OG, and mcBOTH-OG as compared with controls of hiPSCs, OG cells, and mcMock-transduced OG cells. It was identified that SOX9, which is a marker expressed in early chondrocytes, is expressed at a significant level in the chondrogenic pellet derived from the cells transduced with the minicircle vectors (FIG. 14A). In a case of ACAN and COL10A1 markers, it was identified that absolute expression levels thereof are observed at lower levels than SOX9, and that these markers are expressed at higher levels than the positive control, Both rhGF group (FIGS. 14D and 14E). In addition, it was identified that COL2A1 and COL1A1 are also expressed at significant levels in mcBMP2-OG, mcTGFβ3-OG, and mcBOTH-OG, and that the chondrocyte marker genes are expressed at significantly higher levels than the positive control, Both rhGF group (FIGS. 14C and 14D). On the contrary, it was identified that the osteogenic marker RUNX2 is expressed at a lower level than a case where recombinant growth factors are added, and that RUNX2 is expressed at the lowest level in mcBOTH-OG.

The accumulation level of the extracellular matrix (ECM) was identified together with the expression of the chondrocyte marker genes. The ECM accumulation was identified by carrying out alcian blue staining, safranin O staining, and toluidine blue staining for the chondrogenic pellets produced by differentiation induction from mcBMP2-OG, mcTGFβ3-OG, and mcBOTH-OG.

The experimental procedure for this is as follows. Cells of the chondrogenic pellet were first washed with phosphate-buffered saline (PBS). The washed sample was fixed by treatment with 4% paraformaldehyde at room temperature for 2 hours. After the fixation, dehydration was performed using an ethanol solution, and washing was performed again using an ethanol-zylene mixed solution. The washed sample was embedded in paraffin overnight. The obtained paraffin block was fixed and cut into 7 μm sections using a microtome to make sample sections. Prior to staining the respective sections, the sections were placed in an oven at 60° C. for at least 10 minutes to raise the temperature. The sections were immediately deparaffinized with zylene, hydrated with decreasing ethanol concentration, and then rinsed with running tap water for 1 minute.

For the alcian blue staining, the sections were immersed in 1% alcian blue solution (Sigma Aldrich, St. Louis, Mo., USA) and incubated at room temperature for 30 minutes. After the incubation, the sections were washed again with tap water, counter-stained using nuclear fast red solution, and then observed with a microscope.

For the safranin O staining, the sections were treated with a solution of Weigert's hematoxylin (Sigma Aldrich), stained at room temperature for 10 minutes, and then washed again with running tap water for 10 minutes. The washed sections were stained again with 0.001% Fast Green solution (Sigma Aldrich) and 0.1% safranin O solution (Sigma Aldrich) for 5 minutes each, and observed with a microscope.

The toluidine blue staining was carried out by immersing dehydrated sections in 0.04% toluidine blue solution and performing incubation for 10 minutes. The stained sections were washed with running tap water and dried for 10 minutes until complete drying was achieved. At the end of the staining process, the sections were dehydrated with treatment with increasing ethanol concentration. Ethanol was removed by performing treatment with 100% zylene twice, mounted on the VectaMount™ Permanent Mounting Medium (Vector Laboratories, CA, USA), and then observed with a microscope.

In addition, in order to identify the types of collagen constituting the ECM produced, collagen formation of the chondrogenic pellet was checked by immunochemical staining, through type 1 collagen and type 2 collagen staining. Prior to staining the respective sections, the sections were placed in an oven at 60° C. for at least 10 minutes to raise the temperature. The sections were immediately deparaffinized with zylene, hydrated with decreasing ethanol concentration, and then rinsed with running tap water for 1 minute.

Then, the sections were immersed in boiling citrate buffer and rehydrated to unmask antigen proteins. The sections after completion of antigen unmaking were cooled, and then treated with 3% hydrogen peroxide solution to block activity of peroxidase expressed in tissues. Then, the sections were washed again and blocked with TBS containing 1% BSA. Primary antibodies were diluted with the blocking solution and used. The sections were treated with anti-type 1 collagen antibodies (1/200 dilution; Abcam) or anti-type 2 collagen antibodies (1/100 dilution; Abcam) and incubation therewith was performed at 4° C. overnight. Next day, the sections were washed with TBS containing 0.1% Tween-20, and treatment with secondary antibodies was performed. Treatment with the secondary antibodies (1/200 dilution; Vector Laboratories) was performed at room temperature for 40 minutes and then washing was performed. After the washing, treatment with ABC reagent drops (Vector Laboratories) was performed for 30 minutes. Then, the sections were immersed in a DAB solution and incubated for 5 minutes. Counter staining was performed by treatment with Mayer's hematoxylin (Sigma Aldrich) for 1 minute. The counter-stained sections were mounted and microscopically observed with bright illumination.

Figure 15:
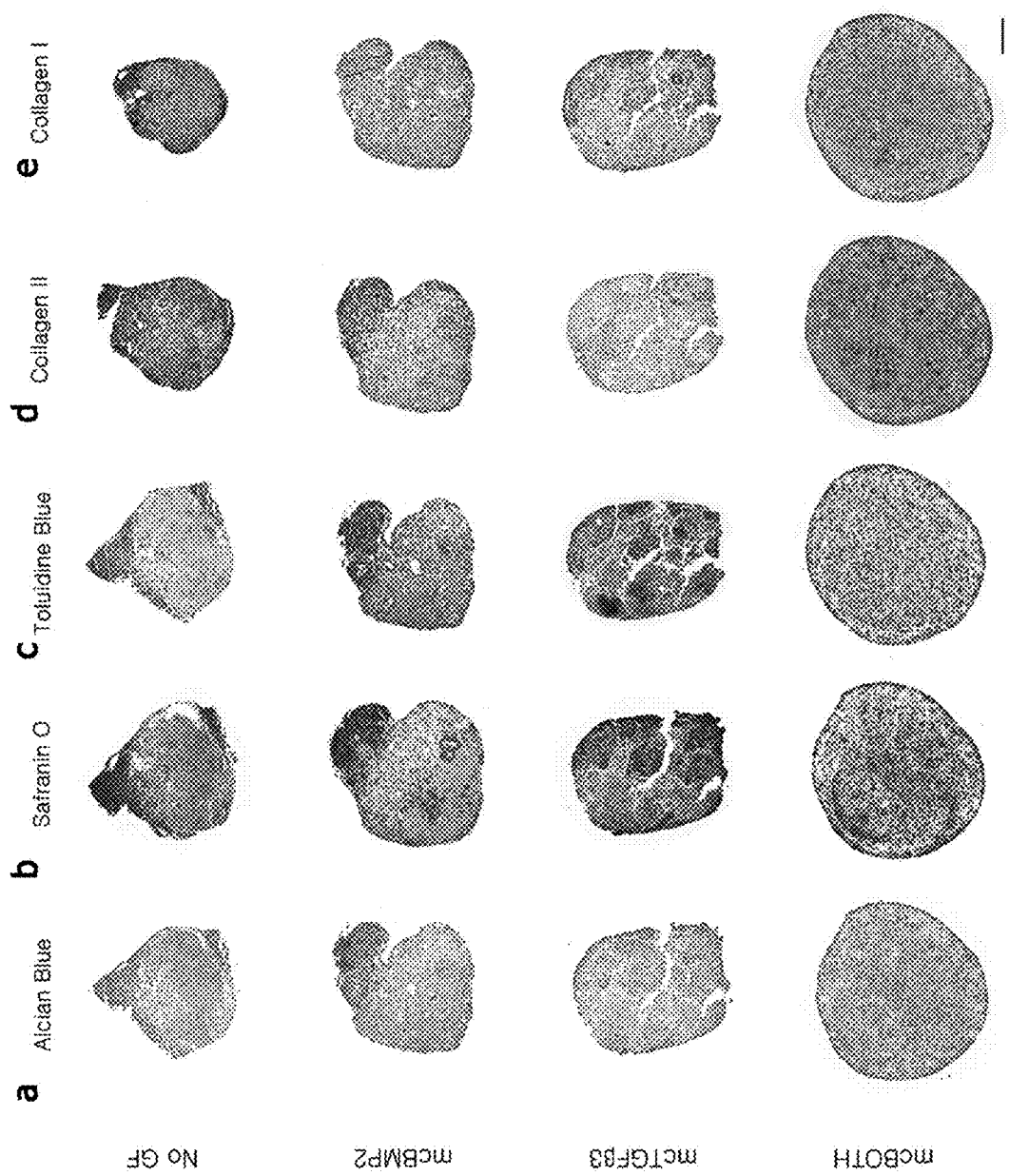
FIGS. 15A-15E illustrate results obtained by identifying characteristics of a chondrogenic pellet produced by differentiation with transduction of the minicircle vectors of the present invention.

As a result, as illustrated in FIG. 15, it was identified that ECM is significantly formed in all experimental groups. Among these, it was identified that overall uniform ECM expression is observed in the mcBMP2-OG-derived chondrogenic pellet exhibits, while ECM is expressed in the form of being accumulated in some regions in the mcTGFβ3-OG-derived chondrogenic pellet (FIGS. 15A to 15C).

Collagen that constitutes cartilage in vivo may include type 1 collagen and type 2 collagen. It is known that type 1 collagen forms fibrous cartilage and type 2 collagen forms hyaline cartilage. It was identified that collagen is significantly expressed in all experimental groups. However, it was identified that both type 1 collagen and type 2 collagen are observed at high levels in the mcBOTH-OG-derived chondrogenic pellet (FIGS. 15D and 15E). Accordingly, the present inventors expected that in the course of inducing differentiation into chondrocytes using the minicircle vectors of the present invention, a more effective induction of differentiation into chondrocytes is possible in a case where mcBMP2-OG and mcTGFβ3-OG are cultured together for differentiation into chondrocytes.

[Example 11] Identification of Cartilage Regeneration Capacity In Vivo of Chondrogenic Pellet Produced by Differentiation Induction with Transduction of Minicircle Vectors In order to identify whether the chondrogenic pellet produced by differentiation induction using the method of the present invention actually exhibits cartilage regeneration capacity in vivo in an effective manner, a regeneration effect was identified by transplanting, into a cartilage defective mouse model, the chondrogenic pellet produced by differentiation induction from mcBOTH-OG.

Figure 16:
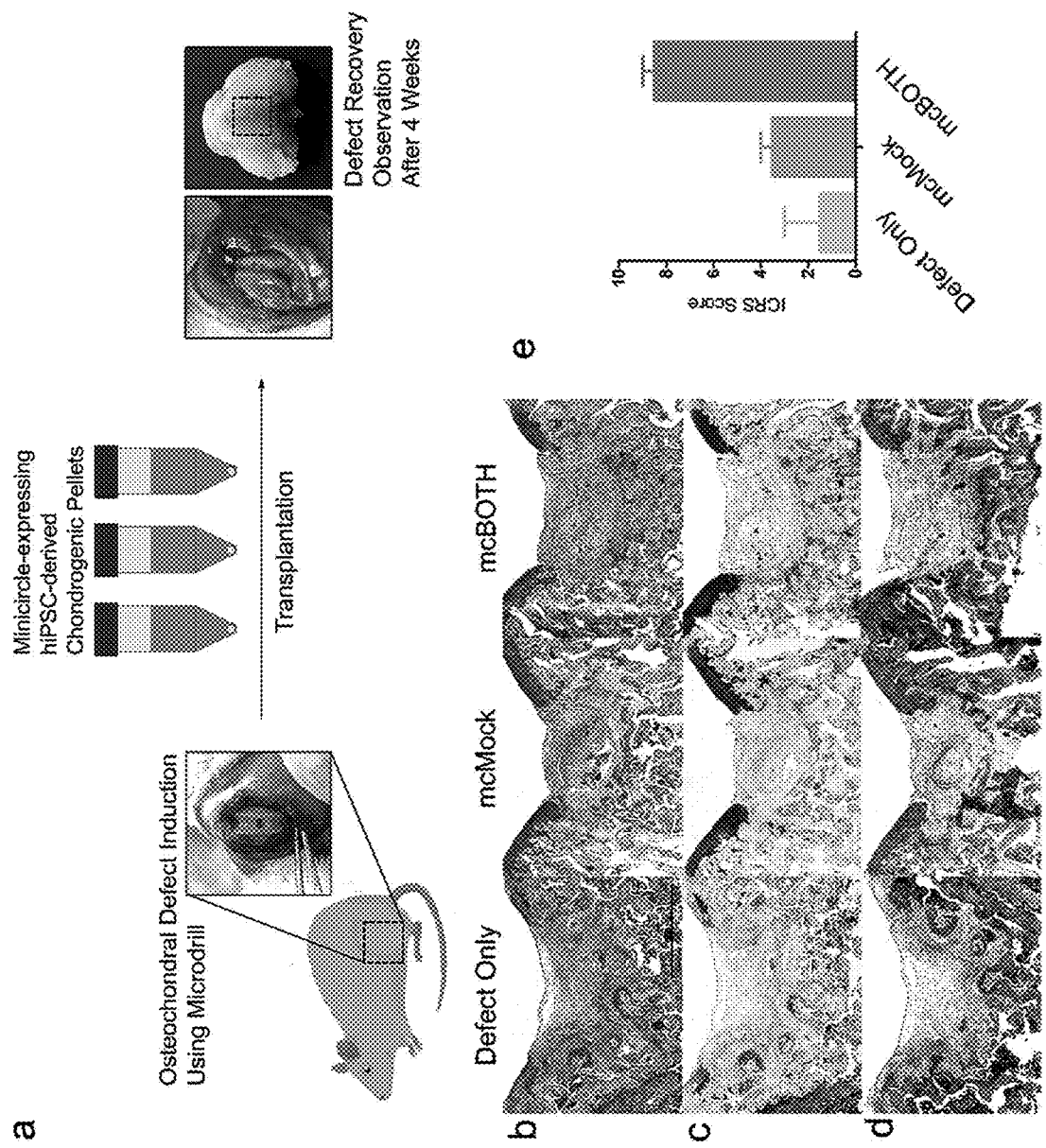
FIGS. 16A-16E illustrate results obtained by identifying in vivo cartilage regeneration capacity of a chondrogenic pellet produced by differentiation induction with transduction of minicircle vectors.

First, a model mouse having osteochondral defect was produced (FIG. 16A). For this purpose, an experimental mouse (Sprague-Dawley) was anesthetized, and osteochondral defect having a size of 1.5 mm×1.5 mm×1.5 mm was induced using a microdrill at articular cartilage of the trochlear groove of the distal femur. Then, the chondrogenic pellet, produced by differentiation induction for 10 days in <Example 8>, was transplanted into the osteochondral defect site. The skin on the surgical site which had been opened for arthrotomy was sealed with a nylon thread. The animal model was fed with sufficient feed and drinking water for 4 weeks after the surgery. 4 weeks later, the mice were sacrificed, and the corresponding osteochondral defect site was observed by immunohistological staining. For cartilage regeneration effects, degrees of regeneration were checked using the recovery scores established by the International Cartilage Repair Society (ICRS) and compared.

As a result, as illustrated in FIGS. 16B-16D, it was identified, through alcian blue staining, toluidine blue staining, and safranin O staining, that ECM formation is induced by the transplanted chondrocytes at the site where osteochondral defect has been induced. It was identified that in the control (defect only) in which the defect has been kept for 4 weeks and the control into which mcMock-OG-derived chondrocytes have been transplanted, ECM accumulation is not observed and the empty space is increased. This was identified as indicating that although the cells of mcMock-OG are transplanted, significant differentiation into chondrocytes does not proceed due to lack of growth factors, and thus cell death is induced.

On the contrary, it was identified that in the experimental group into which the mcBOTH-OG-derived chondrogenic pellet has been transplanted, chondrocytes are densely clustered in various regions and produced by differentiation induction, and thus a cartilage regeneration effect is significantly exhibited to induce ECM accumulation (FIGS. 16B to 16D). In addition, it was identified that even in a case where the histological score is checked, the score is remarkably higher than the control, indicating that cartilage regeneration is effectively achieved (FIG. 16E).

Figure 17:
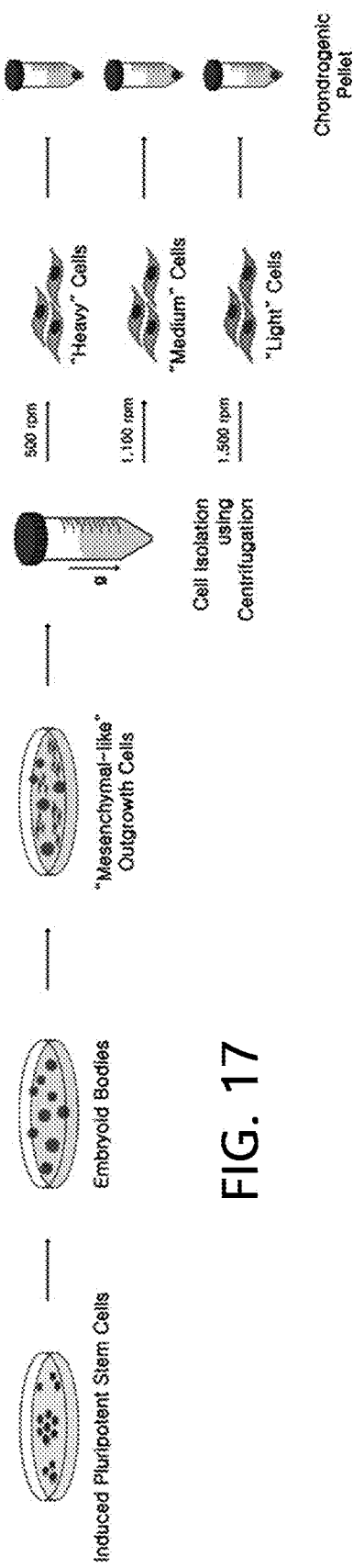
FIG. 17 illustrates a schematic diagram which summarizes the method of the present invention for producing a chondrogenic pellet from induced pluripotent stem cells.

[Example 12] Induction of Differentiation into Chondrocytes with Isolation of Cells by Sizes In order to establish a method capable of producing chondrocytes of cell therapeutic grade, the present inventors have constructed a method in which embryoid bodies (EBs) are produced from induced pluripotent stem cells (iPSCs), mesenchymal-like outgrowth cells (OG cells) are obtained, and the OG cells obtained by size classification through centrifugation are induced to differentiate into chondrocytes (FIG. 17).

i) Preparation of iPSCs

First, cord blood mononuclear cell (CBMC)-derived induced pluripotent stem cells were prepared. Here, the CBMCs used were acquired from the Cord Blood Bank at Seoul ST. Mary's Hospital, Korea. The cord blood was diluted with phosphate buffered saline (PBS) and centrifuged at 850×g for 30 minutes through a Ficoll gradient to collect CBMCs. Then, the CBMCs were washed and frozen, and kept until use. The CBMCs were thawed immediately before use, and then resuspended in StemSpan medium (STEMCELL Technological, Vancouver, British Columbia, Canada) supplemented with CC110 cytokine cocktail (STEMCELL). The resultant was cultured for 5 days in a 5% $CO_2$ incubator at 37° C.

Then, in order to produce iPSCs from the CBMCs, the CBMCs were inoculated into a 24-well plate at a concentration of $3 \times 10^5$, and reprogramming was induced using the CytoTune-iPS Sendai Reprogramming kit according to the protocol provided by the manufacturer. Thus, CBMC-derived iPSCs were obtained.

ii) Induction of Embryoid Bodies (EBs) and Outgrowth Cells (OG Cells) from CBMC-Derived iPSCs The CBMC-derived iPSCs were resuspended in Aggrewell medium (STEMCELL) and inoculated onto a 100-mm culture plate at a concentration of $2 \times 10^6$ cells/well. The inoculated iPSCs were cultured in a 37° C. incubator for 24 hours. Next day, the medium was replaced with TeSR-E8 medium, and then culture was further performed for 6 days to obtain EBs. The obtained EBs were suspended in DMEM medium containing 20% fetal bovine serum (FBS), and cultured on a gelatin-coated plate for 7 days to induce formation of OG cells.

iii) Isolation of OG Cells by Sizes

The formed OG cells were separated from the gelatin-coated plate and passed through a cell strainer (Thermo Fisher Scientific) having a size of 40 μm to remove cell masses. The cells were isolated into single unit cells. The isolated cells were centrifuged so as to be isolated again by sizes. First, the cells were centrifuged at 500 rpm for 5 seconds, and the precipitated cells were obtained as heavy cells. The supernatant was centrifuged again at 1,100 rpm for 5 seconds, and the precipitated cells were obtained as medium cells. In addition, the supernatant was centrifuged again at 1,500 rpm for 5 seconds, and the precipitated cells were obtained as light cells.

iv) Induction of Differentiation of OG Cells into Chondrogenic Pellet

The obtained heavy cells, medium cells, and light cells were respectively counted, inoculated into a chondrogenic differentiation medium at a concentration of $3 \times 10^5$ cells/tube, and cultured. For the chondrogenic differentiation medium, DMEM medium containing 20% knockout serum replacement, 1x non-essential amino acid, 1 mM L-glutamine, 1% sodium pyruvate, 1% ITS+Premix, $10^{-7}$ M Dexamethasone, 50 μm ascorbic acid, 40 μg/ml of L-proline, 50 ng/ml of human bone morphogenetic protein 2, and 10 ng/ml of human transforming growth factor beta 3 was used. The respective cells were inoculated into the chondrogenic differentiation medium, and then centrifuged at 750×g for 5 minutes to precipitate the cells. Culture was performed at 37° C. for 30 days in total with daily replacement with fresh medium, so that a finally differentiation-induced chondrogenic pellet was obtained.

[Example 13] Identification of Differentiation Induction Markers in OG Cells Isolated by Sizes In order to identify whether distinguished differentiation capacity into chondrocytes is exhibited as OG cells are isolated by sizes, characteristics of the OG cells, which had been isolated by sizes through centrifugation, were first identified.

First, cell morphology of the respective heavy OG cells, medium OG cells, and light OG cells obtained in the step iii) of [Example 12] was observed with a microscope. As a result, as illustrated in FIGS. 18A and 18B, it was identified that the cells are isolated depending on their sizes.

Then, the respective cells were equally counted to $5 \times 10^5$ cells for each sample. Then, the respective cells were disrupted using Trizol (Life Technologies), and mRNA was extracted therefrom. Using the mRNA as a template, cDNA was synthesized using the RevertAid™ First Strand cDNA synthesis kit (Thermo Fisher Scientific) according to the protocol provided by the manufacturer. Using the synthesized cDNA as a template, PCR was carried out again using the primer sequences listed in [Table 9] below, to identify mRNA expression levels of SOX9, which is a transcription factor that helps induce differentiation into chondrocytes, and COL10, which is a hypertrophy marker that helps cell growth. The mRNA expression levels were identified by electrophoresis, and then relative expression levels of intracellular SOX9 and COL10A1 were analyzed based on GAPDH for quantitative analysis.

Figure 18:
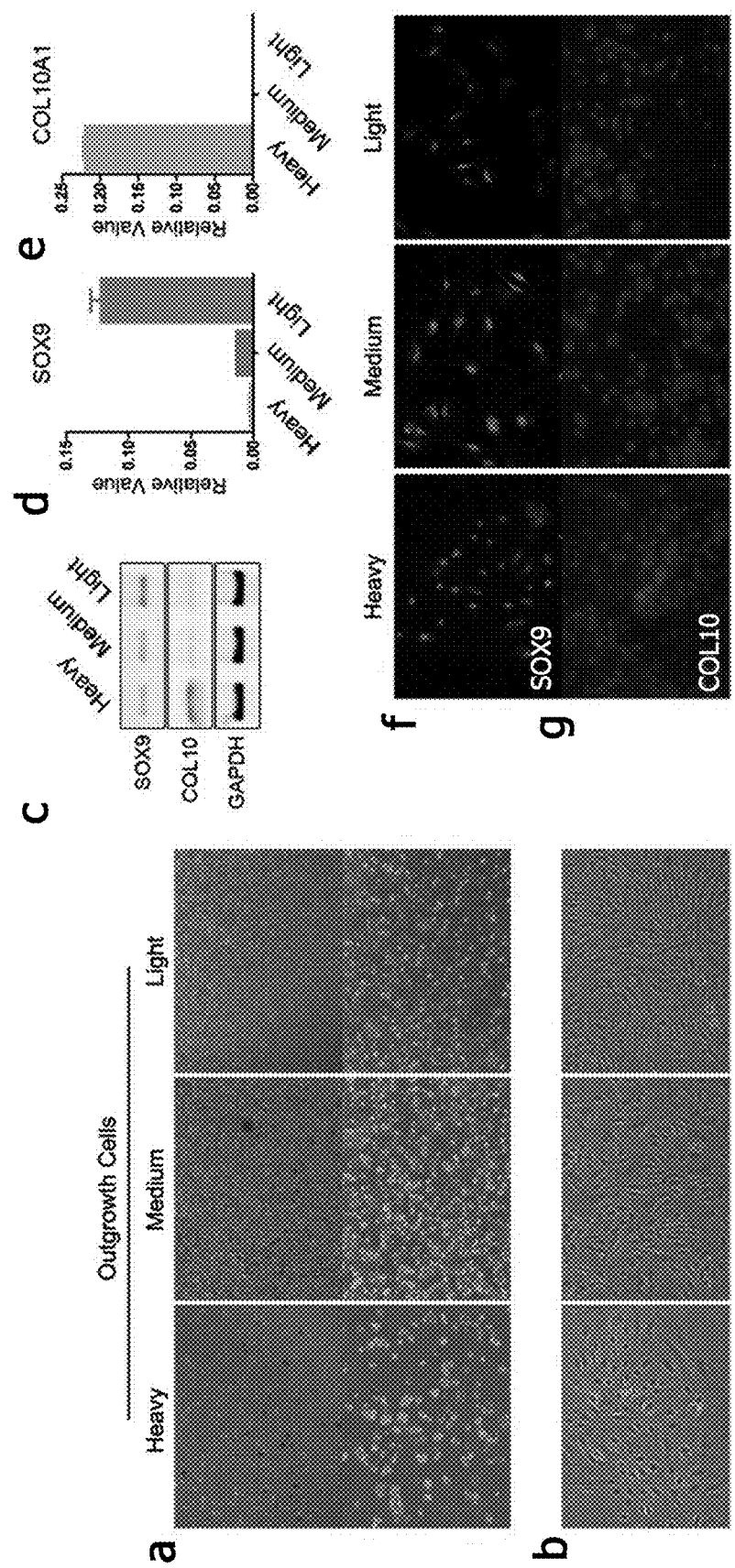
FIGS. 18A-18G illustrate identification of differentiation induction markers in OG cells isolated by sizes.

As a result, as illustrated in FIGS. 18C to 18E, it was identified that the heavy cells exhibit a low expression level of SOX9 and a high expression level of COL10, and the light cells exhibit a relatively high expression level of SOX9 and no expression of COL10.

TABLE 9

List of primers used for identifying expression of markers in inducing differentiation into chondrocytes depending on sizes of OG cells and sequences therefor

| Target Name | Direction | Primer Sequence | Size |
|---|---|---|---|
| SOX5 | Forward | CAGCCAGAGTTAGCACAATAGG | 104 |
|  | Reverse | CTGTTGTTCCCGTCGGAGTT |  |
| SOX6 | Forward | GGATGCAATGACCCAGGATTT | 141 |
|  | Reverse | TGAATGGTACTGACAAGTGTTGG |  |
| SOX9 | Forward | GAACGCACATCAAGACGGAG | 631 |
|  | Reverse | TCTCGTTGATTTCGCTGCTC |  |
| COL2A1 | Forward | GGCAATAGCAGGTTCACGTACA | 79 |
|  | Reverse | CGATAACAGTCTTGCCCCACTTA |  |
| COL1A1 | Forward | TCTGCGACAACGGCAAGGTG | 146 |
|  | Reverse | GACGCCGGTGGTTTCTTGGT |  |
| COL10A1 | Forward | GTCTGCTTTTACTGTTATTCTCTCCAAA | 108 |
|  | Reverse | TGCTGTTGCCTGTTATACAAAATTTT |  |
| ACAN | Forward | AGCCTGCGCTCCAATGACT | 107 |
|  | Reverse | TAATGGAACACGATGCCTTTCA |  |
| CHAD | Forward | GATCCCCAAGGTGTCAGAGAAG | 66 |
|  | Reverse | GCCAGCACCGGGAAGTT |  |

TABLE 9-continued

List of primers used for identifying expression of markers in inducing differentiation into chondrocytes depending on sizes of OG cells and sequences therefor

| Target Name | Direction | Primer Sequence | Size |
|---|---|---|---|
| PRG4 | Forward | AAAGTCAGCACATCTCCCAA | 108 |
| | Reverse | GTGTCTCTTTAGCGGAAGTAGTC | |
| RUNX2 | Forward | TCTTAGAACAAATTCTGCCCTTT | 136 |
| | Reverse | TGCTTTGGTCTTGAAATCACA | |
| OPN | Forward | GGGAGTACGAATACACGGGC | 92 |
| | Reverse | TCGGTAATTGTCCCCACGAG | |
| BGLAP | Forward | ATGAGAGCCCTCACACTCCT | 117 |
| | Reverse | CTTGGACACAAAGGCTGCAC | |

In order to identify again the expression of SOX9 and COL10A1 at the protein level, fluorescence immunoassay was performed. The respective cells were counted to the same number, then washed with PBS, and fixed with 4% paraformaldehyde. The fixed cells were treated with 0.1% Triton X-100 for 10 minutes to have permeability, and then precipitated to obtain cells. The cells were blocked at room temperature for 30 minutes by treatment with PBS (PBA) containing 2% bovine serum albumin (BSA). The blocked cells were treated with anti-SOX9 antibodies or anti-CTLA10 antibodies as primary antibodies, and then allowed to react at room temperature for 2 hours. Then, Alexa Fluor 594-antibodies were added thereto, and reaction was induced in the dark for 1 hour. After completion of the reaction, the cells were washed with PBA, and the stained cells were observed with a fluorescence microscope. Nuclei of the cells were stained with DAPI.

As a result, as illustrated in FIGS. 18F and 18G, it was identified that the heavy OG cells exhibit a low expression level of SOX9 and a high expression level of COL10, and the light OG cells exhibit a relatively high expression level of SOX9 and no expression of COL10. From this, it was identified that a consistent pattern is exhibited between the results obtained at the mRNA expression level and the results obtained at the protein level.

[Example 14] Characterization of OG Cell-Derived Chondrogenic Pellet

<14-1> Identification of Structure Formation Capacity for Chondrogenic Pellet Depending on Sizes of OG Cells It was identified whether among the chondrogenic pellets differentiated through the method of the present invention, a degree of differentiation varies depending on sizes of the OG cells.

Specifically, the colony of the chondrogenic pellet produced by differentiation induction in the step iv) of [Example 12] was fixed with 4% paraformaldehyde at room temperature for 2 hours, and dehydrated with a solution obtained by mixing ethanol and zylene. The dehydrated pellet was fixed with paraffin, and then cut into 7 μm sections to prepare sections. For the prepared sections, toluidine blue staining, safranin O staining, and alcian blue staining were carried out. Each sample was checked with a microscope.

Figure 19:
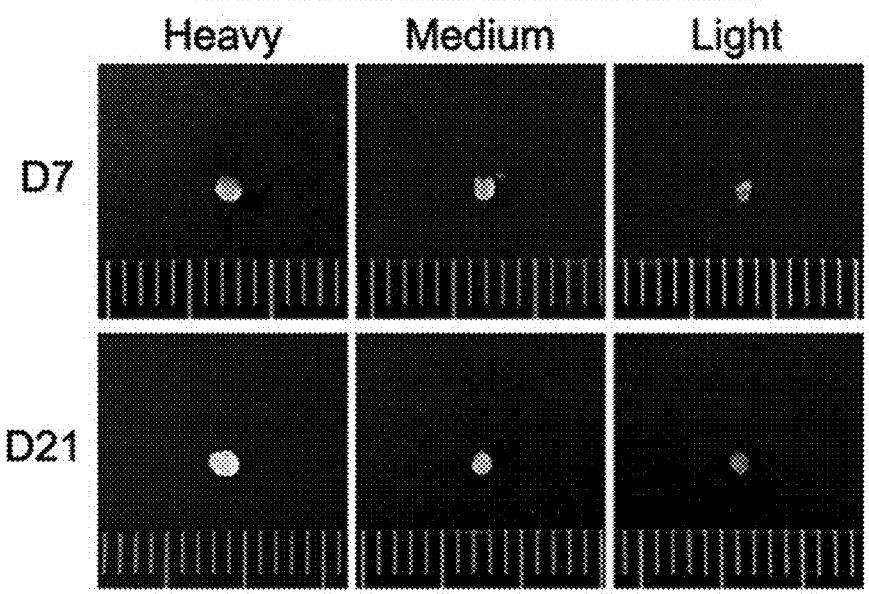
FIGS. 19A-19B illustrate identification of characteristics of OG cell-derived chondrogenic pellets.
Figure 19:
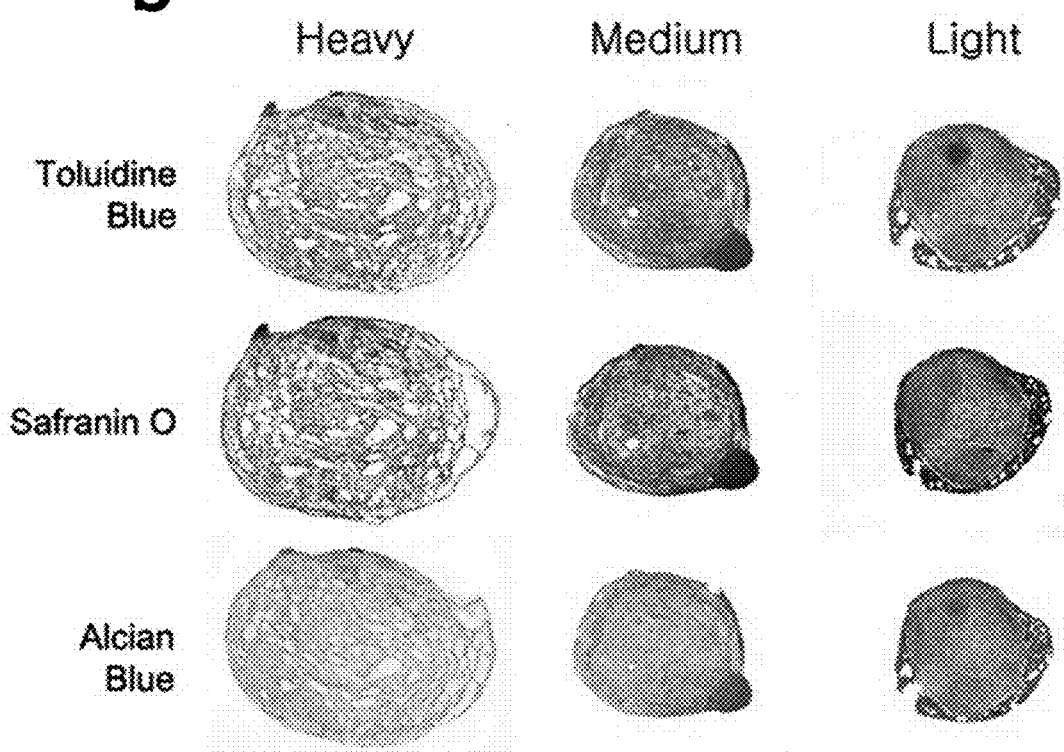

As a result, as illustrated in FIGS. 19A-19B, it was identified that the OG cells isolated depending on their sizes also exhibit different sizes of colonies as the time for inducing differentiation into chondrogenic pellet has elapsed (FIG. 19A). After completion of differentiation induction, in a case where the chondrogenic pellets are stained and histologically checked, it was identified that the chondrogenic pellet produced by differentiation induction from the light cells has a more stable structure (FIG. 19B). On the contrary, it was identified that the chondrogenic pellet produced by differentiation induction from the heavy cells has a loose structure in terms of cartilaginous tissue, indicating similar characteristics to those of osteoarthritic patients.

<14-2> Identification of Difference in Expression Levels of Markers in Chondrogenic Pellet Depending on Sizes of OG Cells In order to identify whether chondrocyte marker genes are expressed in the chondrogenic pellet differentiated through the method of the present invention, gene expression levels of the chondrogenic differentiation promotion markers SOX5, SOX6, and SOX9; the collagen markers COL2A1, COL1A1, and COL10A10; the extracellular matrix proteins ACAN, CHAD, and PRG4; and the bone differentiation markers RUNX2, OPN, and BGLAP were checked.

Specifically, the chondrogenic pellet produced by differentiation induction in the step iv) of [Example 12] was obtained, rapidly frozen with liquid nitrogen, and then ground with pestle and mortar. To each ground sample was added Trizol so that the chondrogenic pellet was disrupted, and total mRNA was extracted therefrom. Using the extracted mRNA as a template, cDNA was synthesized. Using the cDNA again as a template, PCR was performed with the primer sequences shown in [Table 9] above, to identify mRNA expression levels of the respective markers. For the mRNA expression levels, relative expression levels were compared based on GAPDH. Thus, in the differentiated chondrogenic pellets, relative expression levels of the marker genes depending on the sizes of the OG cells were analyzed.

Figure 20:
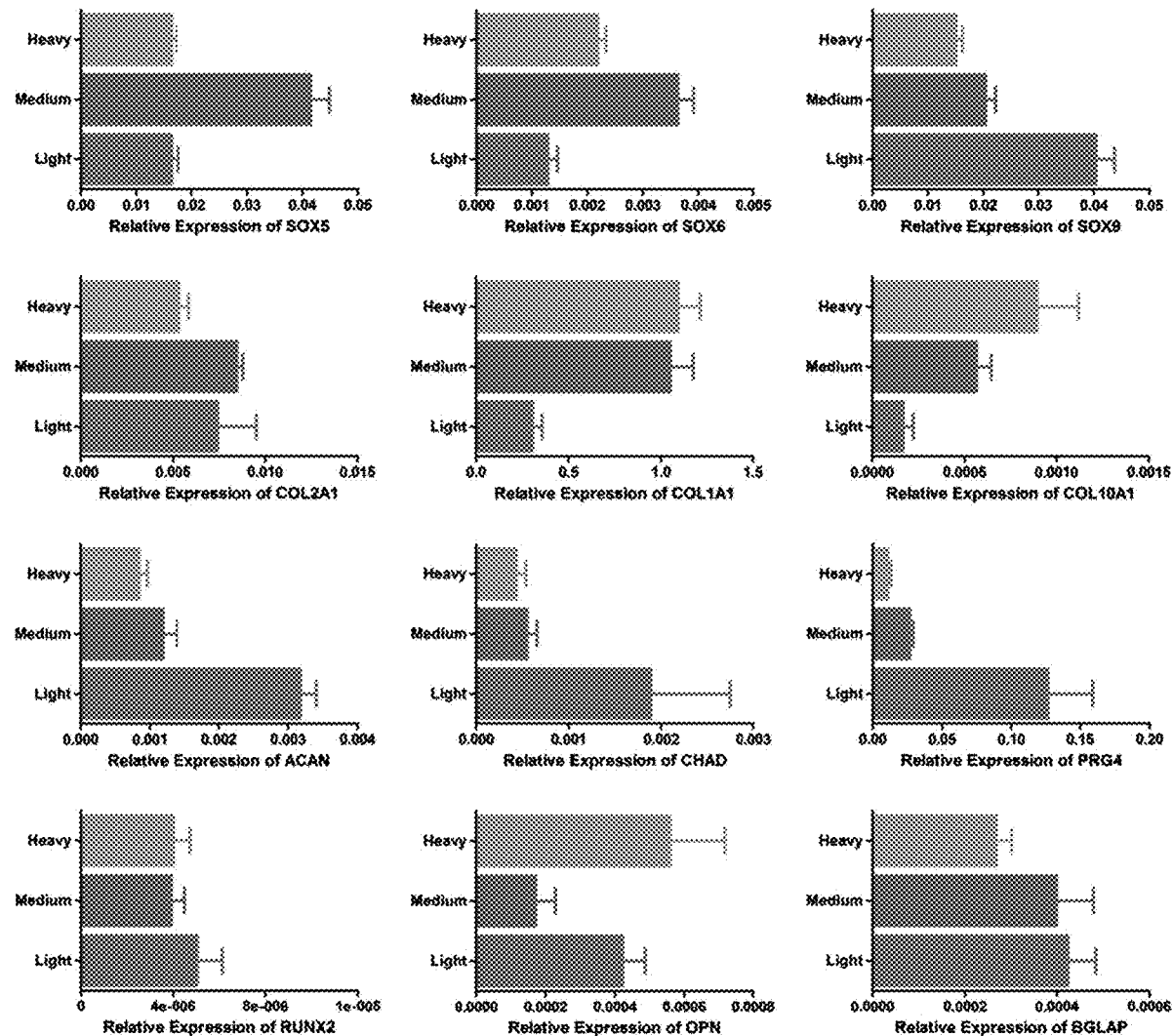
FIG. 20 illustrates results obtained by identifying difference in expression levels of markers for chondrogenic pellets depending on sizes of OG cells.

As a result, as illustrated in FIG. 20, it was identified that as the OG cells are smaller in size, high gene expression of the extracellular matrix proteins is observed in the chondrogenic pellet produced by differentiation induction therefrom, while significance for the chondrogenic differentiation markers is decreased among the groups. From this, it was identified that the light OG cell-derived chondrogenic pellet can significantly exhibit formation of hyaline cartilage and thus has high value.

[Example 15] Identification of Cause by which Different Capacity of Differentiating into Chondrogenic Pellet is Exhibited Depending on Sizes of OG Cells It was identified that OG cells exhibit different differentiation capacities of differentiating into chondrogenic pellets depending on their sizes, and that as the OG cells are smaller, better capacity of differentiating into chondrogenic pellet is exhibited. Thus, it was intended to find a factor that prevents heavy OG cells from exhibiting a significant differentiation capacity.

Specifically, total mRNA was extracted, respectively, from the heavy OG cells, the medium OG cells, and the light OG cells obtained in the step iii) of [Example 12], and then the gene expression level thereof was identified by microarray analysis. From the results of microarray analysis, the expression levels of genes in the medium OG cells and the light OG cells were compared to expression levels of genes in the heavy OG cells, in which a gene of which the expression level is specifically changed in the heavy OG cells was screened.

As a result, as shown in [Table 10] and [Table 11] below, it was identified that as the OG cells are larger, the expression level of insulin-like growth factor 2 (IGF2) is remarkably higher.

TABLE 10

| | Gene Accession | Gene Symbol | Gene Name | Fold Change of H/M, L |
|---|---|---|---|---|
| Upregulated | NM_000612 | IGF2 | Insulin-like Growth Factor 2 | 97.48 |
| | NM_181501 | ITGA1 | Integrin, Alpha 1 | 21.62 |
| | NM_002398 | MEIS1 | Meis Homeobox 1 | 18.70 |
| | NM_005994 | TBX2 | T-box 2 | 11.89 |
| | NM_177963 | SYT12 | Synaptotagmin XII | 11.60 |
| | NM_001083 | PDE5A | Phosphodiesterase 5A, cGMP-specific | 10.22 |
| | NM_021110 | COL14A1 | Collagen, Type XIV, Alpha 1 | 9.73 |
| | NM_130385 | MRVI1 | Murine Retrovirus Integration Site 1 Homolog | 8.71 |
| | NM_152864 | NKAIN4 | Na+/K+ Transporting ATPase Interacting 4 | 8.50 |
| | NM_001452 | FOXF2 | Forkhead Box F2 | 7.75 |
| | NM_001257995 | LMO7DN | LMO7 Downstream Neighbor | 7.60 |
| | NM_005940 | MMP11 | Matrix Metallopeptidase 11 | 7.51 |
| | NM_001290268 | FAM65C | Family with Sequence Similarity 65, Member C | 7.33 |
| | NM_018440 | PAG1 | Phosphoprotein Membrane Anchor with Glycosphingolipid Microdomains 1 | 7.26 |
| | NM_001958 | EEF1A2 | Eukaryotic Translation Elongation Factor 1 Alpha 2 | 7.03 |
| | NM_004572 | PKP2 | Plakophilin 2 | 6.85 |
| | NM_001031804 | MAF | V-Maf Avian Musculoaponeurotic Fibrosarcoma Oncogene Homolog | 6.75 |
| | NM_001993 | F3 | Coagulation factor III | 6.63 |
| | NM_001271948 | PPP2R2B | Protein Phosphatase 2, Regulatory Subunit B, Beta | 6.56 |
| | NM_001105521 | JAKMIP3 | Janus Kinase and Microtubule Interacting Protein 3 | 6.48 |
| | NM_022166 | XYLT1 | Xylosyltransferase I | 6.33 |
| | NM_000399 | EGR2 | Early Growth Response 2 | 6.17 |
| | NM_023037 | FRY | Furry Homolog (*Drosophila*) | 6.12 |
| | NM_002653 | PITX1 | Paired-like Homeodomain 1 | 5.91 |
| | NM_006308 | HSPB3 | Heat Shock 27 kDa protein 3 | 5.87 |
| | NR_125749 | TBX2-AS1 | TBX2 Antisense RNA 1 | 5.78 |
| | NM_000955 | PTGER1 | Prostaglandin E Receptor 1 (Subtype EP1) | 5.78 |
| | NM_004155 | SERPINB9 | Serpin Peptidase Inhibitor, Clade B, Member 9 | 5.76 |
| | NR_034095 | LINC01197 | Long Intergenic Non-protein Coding RNA 1197 | 5.75 |
| | NM_001845 | COL4A1 | Collagen, Type IV, Alpha 1 | 5.65 |

TABLE 11

| | Gene Accession | Gene Symbol | Gene Name | Fold Change of H/M, L |
|---|---|---|---|---|
| Downregulated | NM_015429 | ABI3BP | ABI Family, Member 3 (NESH) Binding Protein | −22.20 |
| | NM_001007156 | NTRK3 | Neurotrophic Tyrosine Kinase, Receptor, Type 3 | −18.56 |
| | NM_024893 | SYNDIG1 | Synapse Differentiation Inducing 1 | −17.16 |
| | NM_020311 | ACKR3 | Atypical Chemokine Receptor 3 | −15.89 |
| | NM_017680 | ASPN | Asporin | −14.44 |
| | NM_001252 | CD70 | CD70 Molecule | −14.25 |
| | NM_003485 | GPR68 | G Protein-coupled Receptor 68 | −13.55 |
| | NM_006100 | ST3GAL6 | ST3 Beta-galactoside Alpha-2,3-sialyltransferase 6 | −11.77 |
| | NR_038236 | LINC00968 | Long Intergenic Non-protein Coding RNA 968 | −11.36 |
| | NM_003836 | DLK1 | Delta-like 1 Homolog (*Drosophila*) | −10.64 |
| | NR_102279 | HOXB-AS1 | HOXB Cluster Antisense RNA 1 | −10.03 |
| | NM_001252065 | SYT7 | Synaptotagmin VII | −9.92 |
| | NM_013363 | PCOLCE2 | Procollagen C-endopeptidase Enhancer 2 | −9.54 |
| | NM_005099 | ADAMTS4 | ADAM Metallopeptidase with Thrombospondin Type 1 Motif, 4 | −9.44 |
| | NM_015225 | PRUNE2 | Prune Homolog 2 (*Drosophila*) | −9.36 |
| | NM_005202 | COL8A2 | Collagen, Type VIII, Alpha 2 | −9.09 |
| | NM_000963 | PTGS2 | Prostaglandin-endoperoxide Synthase 2 | −9.06 |
| | NM_032528 | ST6GAL2 | ST6 Beta-galactosamide alpha-2,6-sialyltranferase 2 | −8.87 |
| | NM_006208 | ENPP1 | Ectonucleotide Pyrophosphatase/Phosphodiesterase 1 | −8.55 |
| | NM_005949 | MT1F | Metallothionein 1F | −8.47 |
| | NM_000337 | SGCD | Sarcoglyan, Delta | −8.07 |
| | NM_007281 | SCRG1 | Stimulator of Chondrogenesis 1 | −7.93 |
| | NM_024119 | DHX58 | DEXH (Asp-Glu-X-His) Box Polypeptide 58 | −7.42 |
| | NM_032849 | MEDAG | Mesenteric Estrogen-dependent Adipogenesis | −7.24 |
| | NM_198449 | EMB | Embigin | −7.10 |
| | NM_002245 | KCNK1 | Potassium Channel, Two Pore Domain Subfamily K, Member 1 | −7.07 |
| | NM_130783 | TSPAN18 | Tetraspanin 18 | −6.93 |
| | NM_001146037 | SLC14A1 | Solute Carrier Family 14, Member 1 | −6.78 |

TABLE 11-continued

| Gene Accession | Gene Symbol | Gene Name | Fold Change of H/M, L |
|---|---|---|---|
| NM_020386 | HRASLS | HRAS-like Suppressor | −6.72 |
| NM_003480 | MFAP5 | Microfibrillar Associated Protein 5 | −6.54 |

H: Heavy OG;
M: Medium OG;
L: Light OG

[Example 16] Identification of Differentiation Capacity of Chondrogenic Pellet Produced by Differentiation Induction in Environment Treated with IGF2 Inhibitor <16-1> Identification of Degree of Proliferation of OG Cells Cultured in IGF2 Inhibitor-Treated Medium From [Example 15], it was identified that depending on sizes of OG cells, chondrogenic pellets differentiated therefrom exhibit different expression levels of IGF2. Thus, it was intended to identify whether the OG cells exhibit changed differentiation capacity in a case where treatment with chromeceptin, an IGF2 inhibitor, is performed.

First, among the OG cells obtained in the step iii) of [Example 12], the heavy cells were cultured for 3 days while treating the medium with chromeceptin at a concentration of 2 nM to 2 μM, in the course of inducing differentiation into a chondrogenic pellet according to the step iv). Then, morphology of the cells was observed over the treatment time, and the number of the proliferated cells was counted.

Figure 21:
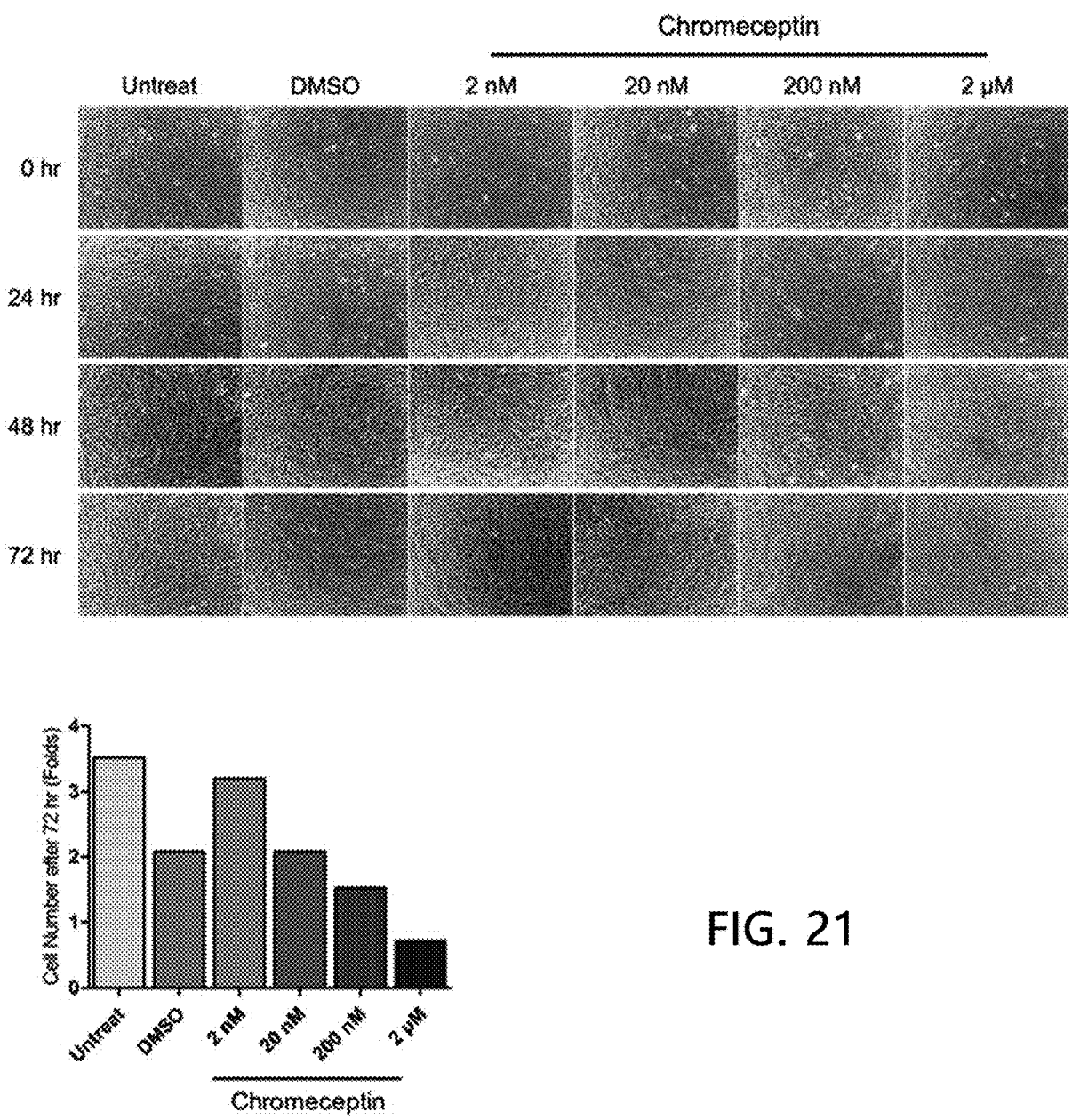
FIG. 21 illustrates results obtained by identifying a proliferation degree of heavy OG cells after performing culture in an environment treated with chromeceptin, an IGF2 inhibitor.

As a result, as illustrated in FIG. 21, it was identified that a degree of proliferation of the cells decreases with increased treatment concentration of chromeceptin, and that after 72 hours, the number of OG cells induced to differentiate in the medium containing 2 μM chromeceptin decreases by about 3 times or higher as compared with the untreated control.

<16-2> Identification of Chondrogenic Differentiation Markers of OG Cells Cultured in IGF2 Inhibitor-Treated Medium It was identified that in a case where treatment with chromeceptin, an IGF2 inhibitor, is performed, proliferative capacity of the OG cells also changes with increased concentration of chromeceptin. Thus, it was intended to identify whether expression levels of chondrogenic differentiation markers differ by treatment with chromeceptin.

Accordingly, heavy OG cells were induced to differentiate into a chondrogenic pellet while performing treatment with chromeceptin under the conditions of Example <16-1>, during which the OG cells were obtained, and mRNA was extracted therefrom and used to synthesize cDNA. Using the synthesized cDNA as a template, expression levels of SOX9, COL2A1, COL10A1, and IGF2 were quantitatively analyzed.

Figure 22:
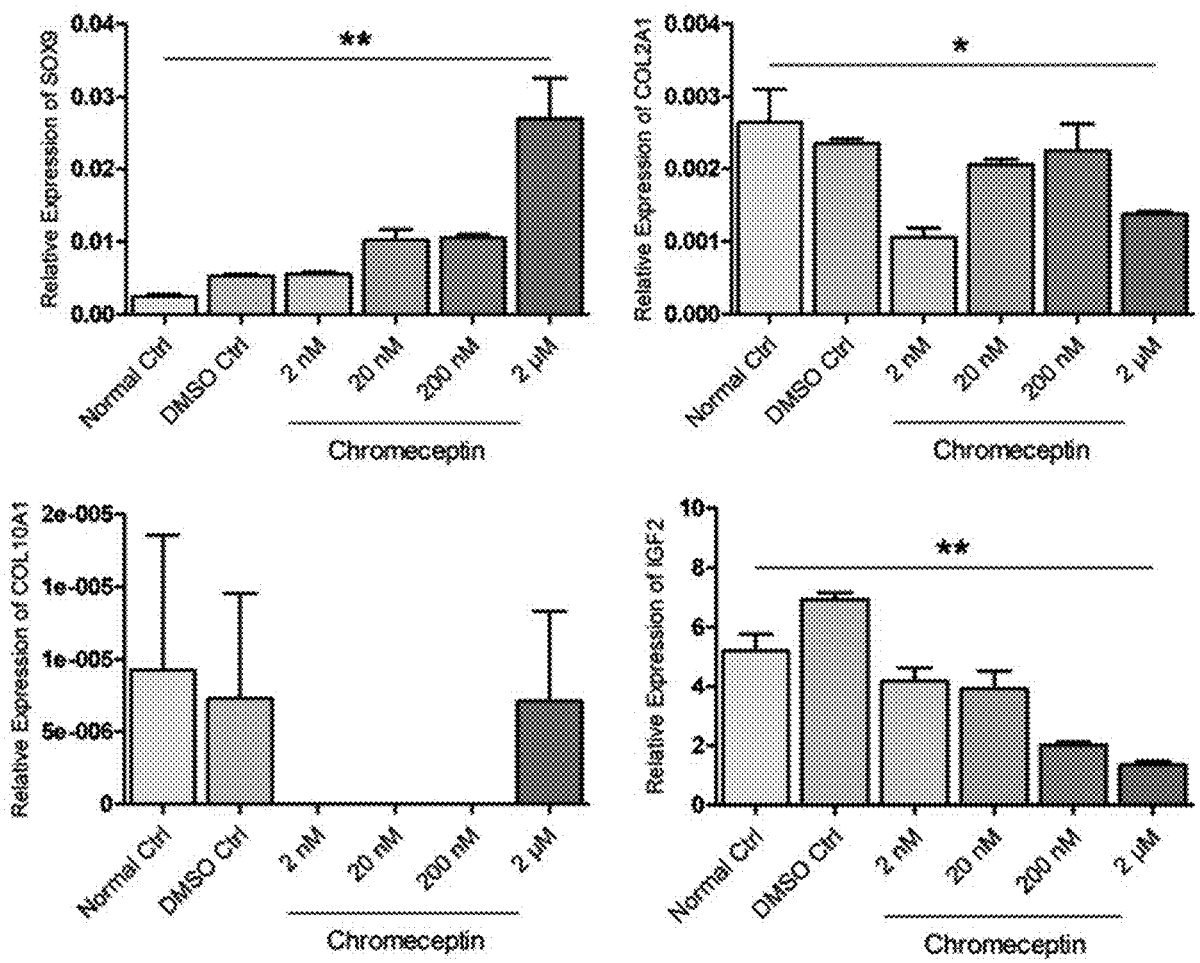
FIG. 22 illustrates results obtained by identifying expression levels of chondrogenic differentiation markers in a case where differentiation of heavy OG cells into a chondrogenic pellet is induced with treatment with chromeceptin.

As a result, as illustrated in FIG. 22, it was first identified that the expression level of IGF2 in the OG cells decreases with increased treatment concentration of chromeceptin. On the contrary, it was identified that the expression level of SOX9, a chondrogenic differentiation marker, significantly increases with increased treatment concentration of chromeceptin, and that the expression level of SOX9 remarkably increases in a cell sample which has been treated with 2 μM chromeceptin as compared with the untreated control (Normal Ctrl).

<16-3> Identification of Chondrocyte Markers in Chondrogenic Pellet Produced by Differentiation Induction in IGF2 Inhibitor-Treated Medium It was identified that the expression levels of chondrogenic differentiation markers can significantly increase even in heavy OG cells by treatment with an IGF2 inhibitor. Accordingly, it was intended to identify whether significant differentiation has occurred in the chondrogenic pellet produced by differentiation induction in this environment.

First, among the OG cells obtained in the step iii) of [Example 12], the heavy cells were cultured for 3 days while treating the medium with chromeceptin at a concentration of 2 mM, in the course of inducing differentiation into a chondrogenic pellet according to the step iv). Experimental groups were divided into two groups, that is, the experimental group (before aggregation) in which differentiation into chondrocytes had been induced by performing treatment with chromeceptin from the beginning of formation of a chondrogenic pellet, and the experimental group (after aggregation) in which differentiation into chondrocytes had been induced by performing treatment with chromeceptin from 7 days after induction of formation of a chondrogenic pellet. The differentiated chondrogenic pellets were respectively obtained therefrom. Then, mRNA was extracted from each of the obtained chondrogenic pellets, and the expression levels of COL2A1, SOX9, COL1A1 and COL10A1 were checked.

Figure 23:
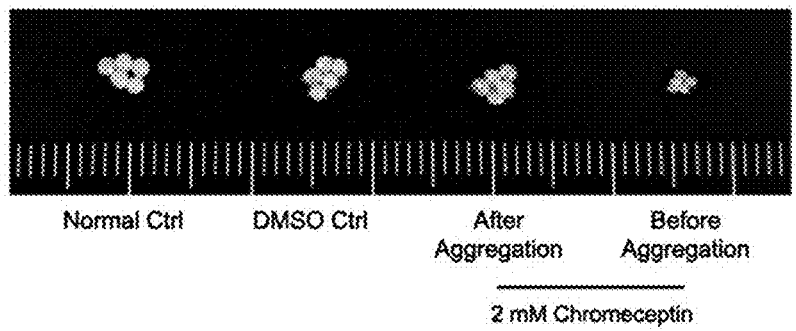
FIGS. 23A-23B illustrates a result obtained by identifying chondrocyte markers in a chondrogenic pellet produced by differentiation induction in an IGF2 inhibitor-treated medium. Here, the OG cells used in the experiment were heavy OG cells isolated by centrifugation. As a normal control, a sample induced to differentiate into a chondrogenic pellet in an environment with no chromeceptin treatment was used.
Figure 23:
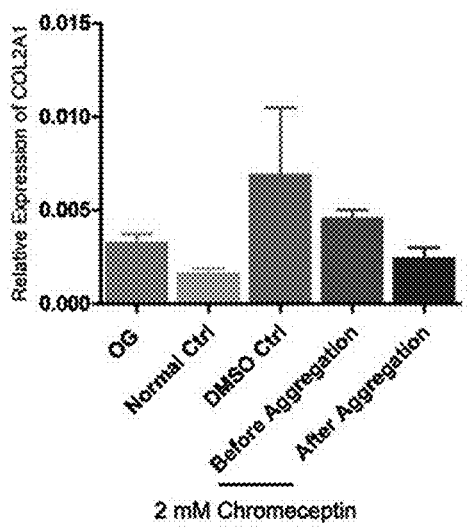
Figure 23:
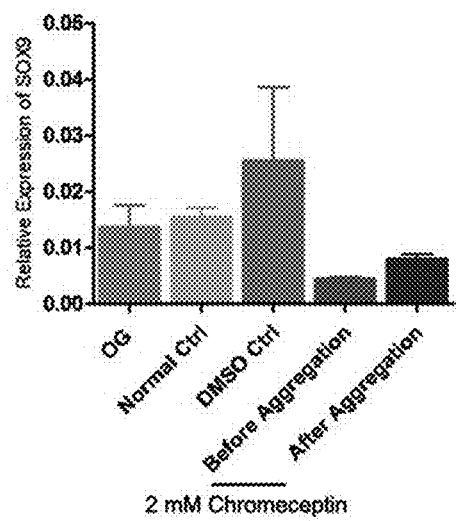
Figure 23:
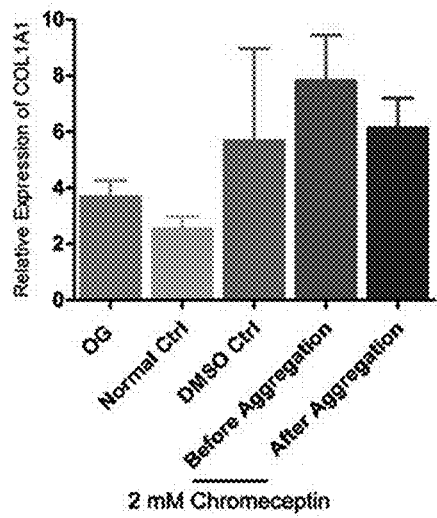
Figure 23:
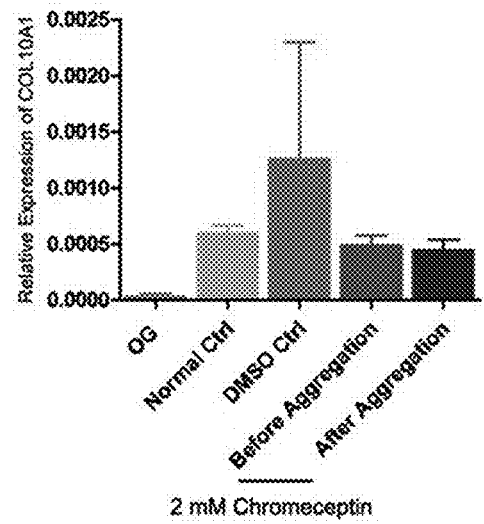

As a result, as illustrated in FIGS. 23A-23B, it was identified that as differentiation into a chondrogenic pellet is induced with treatment with chromeceptin, the expression level of SOX9, a chondrocyte marker, is significantly increased in a case of being at a later stage (after aggregation) of formation of the chondrogenic pellet as compared with a case of being an initial stage (before aggregation) of formation of the chondrogenic pellet.

The invention claimed is:

1. A method for producing chondrocytes obtained by differentiation induction from stem cells, comprising:
   i) culturing induced pluripotent stem cells (iPSCs) to obtain embryoid bodies, wherein the induced pluripotent stem cells of step i) are obtained by reprogramming cord blood mononuclear cells;
   ii) performing adherent culture of the embryoid bodies obtained in step i), to obtain outgrowth cells (OG cells);
   iii) performing centrifugation of the OG cells obtained in step ii) so that the OG cells are isolated by sizes, and selecting light OG cells;
   iv) inducing differentiation of the light OG cells selected in step iii) into chondrocytes; and
   v) obtaining the chondrocytes produced by differentiation induction in step iv),
   wherein the centrifugation and selection in step iii) is performed through the following steps a) to c):
   a) centrifuging a medium containing the OG cells at 300 rpm to 800 rpm for 3 to 10 seconds, to classify precipitated cells as heavy OG cells;
   b) centrifuging the supernatant after the centrifugation in step a) at 800 rpm to 1,200 rpm for 3 to 10 seconds, to classify precipitated cells as medium OG cells; and
   c) centrifuging the supernatant after the centrifugation in step b) at 1,200 rpm to 2,000 rpm for 3 to 10 seconds, to classify precipitated cells as the light OG cells, and
   wherein the light OG cells exhibit higher expression level of SOX9 and lower expression level of COL10 than the heavy OG cells and the medium OG cells.

2. The method according to claim 1,
   wherein the adherent culture in step ii) is performed by culturing the OG cells on a gelatin-coated plate.

3. The method according to claim 1,
   wherein the inducing differentiation in step iv) is performed in a medium containing human bone morphogenetic protein 2 and human transforming growth factor beta 3.

4. The method according to claim 3,
   wherein the medium is additionally supplemented with an IGF2 inhibitor.

* * * * *

SEQUENCE LISTING

```
<160> NUMBER OF SEQ ID NOS: 2

<210> SEQ ID NO 1
<211> LENGTH: 1119
<212> TYPE: DNA
<213> ORGANISM: Homo sapiens
```

<400> SEQUENCE: 1

```
ctcgttcccg agcttggtcg gaggaagttt gcggccgcgt caagcggaag gcccagtagt    60
cagcctagcg acgaggtcct ttctgaattc gagcttcggc tcctgtccat gtttggactt   120
aaacagcgac ctacgcccag ccgggatgcc gttgtaccgc cctatatgct cgatctttat   180
cgaagacatt ccggtcagcc aggatcaccg gctccagatc atagacttga gcgcgctgcc   240
tcccgggcaa acactgtgcg atcctttcac catgaggaat cactggaaga attgccagaa   300
acttcaggta agactacgag acgattcttt tttaatctct catccattcc tacagaagaa   360
ttcattacgt ctgccgagct tcaggtattc agagaacaga tgcaagatgc tttggggaat   420
aacagcagct ttcaccatcg catcaacata tacgagataa tcaaacccgc aacagccaac   480
agcaaatttc ccgtaacgcg attgctggat acgcgacttg tgaaccaaaa cgctagcaga   540
tgggaatcat tcgatgtgac gcccgcggtc atgagatgga ccgctcaggg ccacgcgaat   600
cacggctttg ttgtagaggt ggcacatctt gaagagaagc aaggtgtcag caaaagacat   660
gtacgaataa gtcgatcact ccatcaagat gaacactcat ggagccaaat aagacctctc   720
cttgtgacat tcgggcatga cggaaagggt caccctcttc acaaaaggga gaagcgccag   780
gcgaagcata acagcggaa acgccttaag tcaagttgca acgccatcc tttgtacgtc   840
gatttctccg atgttggatg gaatgattgg atcgtagctc ctcctggata ccatgccttc   900
tattgccatg gcgagtgccc gttccctctt gcggatcatc tcaacagtac caatcatgca   960
atcgtgcaaa cccttgtaaa cagcgtcaac tccaaaattc ccaaggcttg ttgcgttcct  1020
actgagctga gcgccataag tatgctgtac ctcgatgaaa atgaaaaagt tgtcctgaag  1080
aattatcaag atatggtggt agaaggttgt ggatgtagg                         1119
```

<210> SEQ ID NO 2
<211> LENGTH: 1167
<212> TYPE: DNA
<213> ORGANISM: Homo sapiens

<400> SEQUENCE: 2

```
ttgtccacct gtactacttt ggattttggt cacataaaaa aaaaacgggt cgaggcaatc    60
cgagggcaaa ttctcagcaa actgaggctt acatcacccc ccgaaccgac cgttatgacc   120
cacgtaccat atcaggtctt ggctctgtat aactctactc gcgaactgct tgaggagatg   180
catggggaaa gagaggaggg ttgtacccaa gagaataccg aaagcgagta ctatgctaag   240
gagattcata aattcgatat gattcagggt ctggcagagc acaacgagct ggcagtgtgt   300
ccaaaaggaa tcacctcaaa ggtgtttcgc ttcaatgtat ccagcgtcga aaagaatcgc   360
accaacctct tccgagcgga gtttaggggtt cttcgggtac caaaccctag ctcaaagcga   420
aatgagcaac gcattgagtt gttccagata cttaggccgg atgaacacat tgcgaagcag   480
aggtatatag gtggtaaaaa cctcccgact cggggtactg cggagtggct ctcatttgat   540
gtcaccgaca cagtacgcga atggcttctg cgaagagaga gcaatcttgg acttgaaatc   600
agtatccact gtccttgtca taccttccaa ccgaatggag atatactgga gaacatccac   660
gaggtaatgg aaattaagtt taaggcgtg acaacgaag atgatcacgg tcggggtgat   720
ctgggacgac tgaagaaaca aaaagaccac cataacccgc atctgatcct tatgatgatc   780
cccccgcata gactcgacaa cccaggtcaa ggcgggcaga gaaagaaaag agctctggat   840
actaactact gttttaggaa tctggaagaa aactgctgcg tacgacccctt gtatattgat   900
```

-continued

```
tttagacaag acctcggttg gaaatgggtc cacgaaccaa agggatacta tgccaatttc    960
tgtagcggcc cttgtcccta cttgaggagt gccgacacta cacattctac tgtgctcggt   1020
ttgtataaca ccttgaaccc agaagctagt gcatctccct gctgcgttcc ccaggatctc   1080
gaacccctca ctattttgta ttacgttggt cggacaccaa aagtcgaaca actttcaaac   1140
atggtcgtga agtcctgtaa gtgcagc                                       1167
```